United States Patent
Embrey et al.

(10) Patent No.: US 10,221,186 B2
(45) Date of Patent: *Mar. 5, 2019

(54) SPIROCYCLIC HETEROCYCLIC COMPOUNDS USEFUL AS HIV INTEGRASE INHIBITORS

(71) Applicant: Merck Sharp & Dohme Corp., Rahway, NJ (US)

(72) Inventors: Mark W. Embrey, Harleysville, PA (US); Thomas H. Graham, Quingy, MA (US); Izzat T. Raheem, Doylestown, PA (US); John D. Schreier, Harleysville, PA (US); Sherman T. Waddell, Westfield, NJ (US); John S. Wai, Harleysville, PA (US); Lihong Hu, Shanghai (CN); Xuanjia Peng, Shanghai (CN)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/533,169

(22) PCT Filed: Dec. 4, 2015

(86) PCT No.: PCT/US2015/063850
§ 371 (c)(1),
(2) Date: Jun. 5, 2017

(87) PCT Pub. No.: WO2016/094197
PCT Pub. Date: Jun. 16, 2016

(65) Prior Publication Data
US 2017/0334924 A1    Nov. 23, 2017

(30) Foreign Application Priority Data
Dec. 9, 2014 (WO) ................ PCT/CN2014/093335

(51) Int. Cl.
| A61K 31/499 | (2006.01) |
| A61K 31/675 | (2006.01) |
| A61K 31/683 | (2006.01) |
| C07F 9/6561 | (2006.01) |
| C07D 487/20 | (2006.01) |
| C07D 491/20 | (2006.01) |
| A61K 45/06 | (2006.01) |
| A61P 31/18 | (2006.01) |

(52) U.S. Cl.
CPC .......... *C07D 491/20* (2013.01); *A61K 31/499* (2013.01); *A61K 31/675* (2013.01); *A61K 31/683* (2013.01); *A61K 45/06* (2013.01); *A61P 31/18* (2018.01); *C07D 487/20* (2013.01); *C07F 9/6561* (2013.01)

(58) Field of Classification Search
CPC .. A61K 31/499; A61K 31/675; A61K 31/683; C07F 9/6561; C07D 487/20; C07D 491/20
USPC ................. 514/249; 544/230, 231
See application file for complete search history.

(56) References Cited

U.S. PATENT DOCUMENTS

| 7,856,788 | B2 | 12/2010 | Thompson |
| 8,865,907 | B2 | 10/2014 | Sumino et al. |
| 2006/0052361 | A1 | 3/2006 | Miyazaki et al. |
| 2008/0015187 | A1 | 1/2008 | Wai et al. |
| 2012/0108564 | A1 | 5/2012 | Miyazaki et al. |
| 2014/0221356 | A1 | 8/2014 | Jin et al. |
| 2014/0221378 | A1 | 8/2014 | Miyazaki et al. |

FOREIGN PATENT DOCUMENTS

| CN | 101146540 A | 3/2008 |
| CN | 102858771 A | 1/2013 |
| WO | 2015095258 A1 | 6/2016 |
| WO | 2016094198 A1 | 6/2016 |

OTHER PUBLICATIONS

International Search Report and Written Opinion for PCT/US2015/063850, dated Apr. 13, 2016, 10 pages.
International Search Report and Written Opinion for PCT/CN2014/093335, dated May 30, 2016, 14 pages.
Supplementary European Search Report for 15868594.1, dated Jun. 11, 2018.

*Primary Examiner* — Brenda L Coleman
(74) *Attorney, Agent, or Firm* — Nicole M. Beeler; John C. Todaro

(57) ABSTRACT

The present invention relates to Spirocyclic Heterocycle Compounds of Formula (I): and pharmaceutically acceptable salts thereof, wherein A, B, X, Y, $R^1$, $R^2$ and $R^4$ are as defined herein. The present invention also relates to compositions comprising at least one Spirocyclic Heterocycle Compound, and methods of using the Spirocyclic Heterocycle Compounds for treating or preventing HIV infection in a subject.

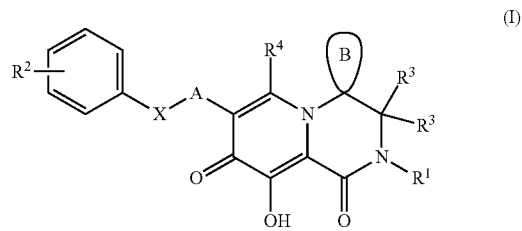

(I)

13 Claims, No Drawings

SPIROCYCLIC HETEROCYCLIC COMPOUNDS USEFUL AS HIV INTEGRASE INHIBITORS

CROSS REFERENCE TO RELATED APPLICATIONS

This application is a U.S. National Phase application under 35 U.S.C. § 371 of PCT Application No. PCT/US2015/063850 filed Dec. 4, 2015, which claims priority from PCT Application No. PCT/CN14/093335 filed Dec. 9, 2014.

FIELD OF THE INVENTION

The present invention relates to Spirocyclic Heterocycle Compounds, compositions comprising at least one Spirocyclic Heterocycle Compound, and methods of using the Spirocyclic Heterocycle Compounds for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Tohours, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

SUMMARY OF THE INVENTION

In one aspect, the present invention provides Compounds of Formula (I):

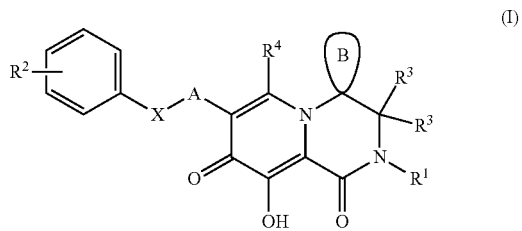

or a pharmaceutically acceptable salt thereof,
wherein:
A is —NHC(O)— or 5- or 6-membered monocyclic heteroaryl;
B is a 3 to 8-membered heterocycloalkyl, which can be optionally substituted with one or more groups, each independently selected from $R^5$;
X is $C_1$-$C_4$ alkylene;
$R^1$ is selected from $C_1$-$C_6$ alkyl, $C_3$-$C_7$ cycloalkyl, $C_1$-$C_6$ haloalkyl, $C_1$-$C_6$ hydroxyalkyl, —($C_1$-$C_4$ alkylene)-O—($C_1$-$C_6$ alkyl), —($C_1$-$C_4$ alkylene)-S—($C_1$-$C_6$ alkyl), —($C_1$-$C_4$ alkylene)-$SO_2$—($C_1$-$C_6$ alkyl), —N($C_1$-$C_6$ alkyl)$_2$, —($C_1$-$C_4$ alkylene)-N($C_1$-$C_6$ alkyl)$_2$, —($C_1$-$C_4$ alkylene)-P(O)(OR$^8$)$_2$, —($C_1$-$C_4$ alkylene)-R$^9$, phenyl, 3 to 8-membered monocyclic heterocycloalkyl and 5- or 6-membered monocyclic heteroaryl;
$R^2$ represents up to 3 optional substitutents, each independently selected from halo, $C_1$-$C_6$ alkyl, —O—($C_1$-$C_6$ alkyl) and $C_1$-$C_6$ haloalkyl;
each occurrence of $R^3$ is independently selected from H, $C_1$-$C_6$ alkyl, —OH, —O—($C_1$-$C_6$ alkyl), $C_1$-$C_6$ haloalkyl, $C_3$-$C_7$ cycloalkyl, —S—($C_1$-$C_6$ alkyl), —($C_1$-$C_4$ alkylene)$_m$-P(O)(OR$^8$)$_2$, —($C_1$-$C_4$ alkylene)$_m$-R$^9$, —NH$_2$, —NH($C_1$-$C_6$ alkyl) and —N($C_1$-$C_6$ alkyl)$_2$;
$R^4$ is selected from $C_1$-$C_6$ alkyl, $C_3$-$C_7$ cycloalkyl, —($C_1$-$C_4$ alkylene)-O—($C_1$-$C_6$ alkyl) and $C_1$-$C_6$ haloalkyl;
each occurrence of $R^5$ is independently selected from halo, $C_1$-$C_6$ alkyl, $C_1$-$C_6$ haloalkyl, 3 to 8-membered monocyclic heterocycloalkyl, 6 to 10-membered bicyclic heterocycloalkyl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —NH$_2$, —NH($C_1$-$C_6$ alkyl), —N($C_1$-$C_6$ alkyl)$_2$, —S(O)$_2$($C_1$-$C_6$ alkyl), —NHS(O)$_2$—($C_1$-$C_6$ alkyl), —S(O)$_2$NH—($C_1$-$C_6$ alkyl), —OC(O)—($C_1$-$C_6$haloalkyl), —($C_1$-$C_6$ alkylene)$_p$-C(O)O—($C_1$-$C_6$ alkyl), —($C_1$-$C_6$ alkylene)$_p$-C(O)—($C_1$-$C_6$ alkyl), —($C_1$-$C_6$ alkylene)$_p$-C(O)N(R$^6$)$_2$, $C_1$-$C_6$ hydroxyalkyl—($C_1$-$C_4$ alkylene)$_m$-P(O)(OR$^8$)$_2$, —($C_1$-$C_4$ alkylene)$_m$-R$^9$ and —CN;
each occurrence of $R^6$ is independently selected from H, $C_1$-$C_6$ alkyl, $C_3$-$C_7$ cycloalkyl, $C_1$-$C_6$ haloalkyl and —($C_1$-$C_6$ alkylene)$_p$—R$^7$; each occurrence of $R^7$ is independently selected from H, $C_1$-$C_6$ alkyl, —O—($C_1$-$C_6$ alkyl), $C_3$-$C_7$ cycloalkyl, 5- or 6-membered monocyclic heteroaryl and 3 to 8-membered monocyclic heterocycloalkyl;
each occurrence of $R^8$ is independently selected from H, $C_1$-$C_6$ alkyl and —($C_1$-$C_3$ alkylene)-O(C)O—($C_1$-$C_6$ alkyl);
each occurrence of $R^9$ is independently :

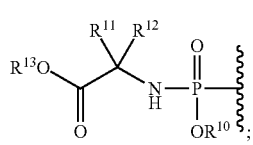

each occurrence of $R^{10}$ is independently selected from H, $C_6$-$C_{10}$ aryl, 5- or 6-membered monocyclic heteroaryl or 9- or 10-membered bicyclic heteroaryl;

each occurrence of $R^{11}$ is independently selected from H, $C_1$-$C_6$ alkyl, $C_3$-$C_7$ cycloalkyl, phenyl or benzyl;

each occurrence of e is independently selected from H, $C_1$-$C_6$ alkyl, $C_3$-$C_7$ cycloalkyl, phenyl or benzyl;

each occurrence of $R^{13}$ is independently $C_1$-$C_6$ alkyl;

each occurrence of m is independently 0 or 1.and each occurrence of p is independently 0 or 1.

The Compounds of Formula (I) (also referred to herein as the "Spirocyclic Heterocycle Compounds") and pharmaceutically acceptable salts thereof, can be useful, for example, for inhibiting HIV viral replication or replicon activity, and for treating or preventing HIV infection in a subject. Without being bound by any specific theory, it is believed that the Spirocyclic Heterocycle Compounds inhibit HIV viral replication by inhibiting HIV Integrase.

Accordingly, the present invention provides methods for treating or preventing HIV infection in a subject, comprising administering to the subject an effective amount of at least one Spirocyclic Heterocycle Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes to Spirocyclic Heterocycle Compounds, compositions comprising at least one Spirocyclic Heterocycle Compound, and methods of using the Spirocyclic Heterocycle Compounds for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Spirocyclic Heterocycle Compound and/or an additional therapeutic agent, or a composition thereof that is effective in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C (O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "C$_1$-C$_4$ alkylene" refers to an alkylene group having from 1 to 4 carbon atoms. The term "C$_1$-C$_6$ alkylene" refers to an alkylene group having from 1 to 6 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═CHCH$_2$—, —CH$_2$CH═CH—, —CH$_2$CH═CHCH$_2$—, —CH═CHCH$_2$CH$_2$—, —CH$_2$CH$_2$CH═CH— and —CH(CH$_3$)CH═CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "C$_2$-C$_6$ alkylene" refers to an alkenylene group having from 2 to 6 carbon atoms. The term "C$_3$-C$_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

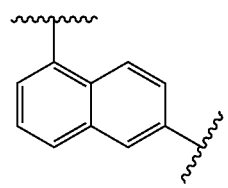

is understood to represent both:

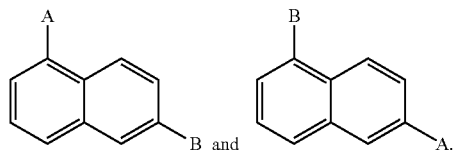

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

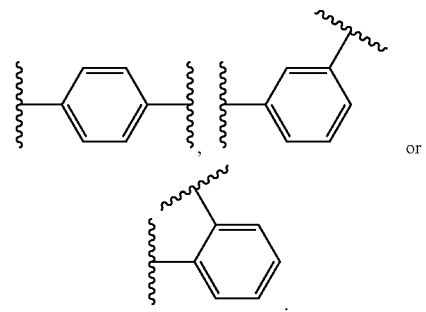

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

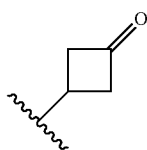

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In one embodiment, a heterocycloalkyl group is monocyclic and has from about 3 to about 8 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

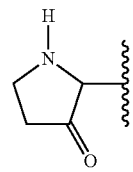

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "3 to 8-membered monocyclic heterocycloalkyl" refers to a monocyclic heterocycloalkyl group having from 3 to 8 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

Examples of "ring system substituents," include, but are not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)- aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

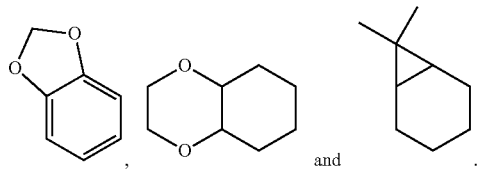

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, R$^1$, R$^7$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Spirocyclic Heterocycle Compound or a pharmaceutically acceptable salt of the compound. The transformation may occur by various mechanisms (e.g., by metabolic or chemical processes), such as, for example, through hydrolysis in blood. For example, if a Spirocyclic Heterocycle Compound or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$—C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-(C$_1$-C$_2$)alkylamino(C$_2$-C$_3$)alkyl (such as β-dimethylaminoethyl), carbamoyl-(C$_1$-C$_2$)alkyl, N,N-di(C$_1$-C$_2$)alkylcarbamoyl-(C$_1$-C$_2$)alkyl and piperidino-, pyrrolidino- or morpholino(C$_2$-C$_3$)alkyl, and the like.

Similarly, if a Spirocyclic Heterocycle Compound contains an alcohol functional group, a prodrug can be formed by the replacement of one or more of the hydrogen atoms of the alcohol groups with a group such as, for example, (C$_1$-C$_6$)alkanoyloxymethyl, 1-((C$_1$-C$_6$)alkanoyloxy)ethyl, 1-methyl-1((C$_1$-C$_6$)alkanoyloxy)ethyl, (C$_1$-C$_6$)alkoxycarbonyloxymethyl, N-(C$_1$-C$_6$)alkoxycarbonylaminomethyl, succinoyl, (C$_1$-C$_6$)alkanoyl, α-amino(C$_1$-C$_4$)alkyl, α-amino(C$_1$-C$_4$)alkylene-aryl, arylacyl and a-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Spirocyclic Heterocycle Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently (C$_1$-C$_{10}$)alkyl, (C$_3$-C$_7$) cycloalkyl, benzyl, a natural α-aminoacyl, —C(OH)C(O)OY$^1$ wherein Y$^1$ is H, (C$_1$-C$_6$) alkyl or benzyl, —C(OY$^2$)Y$^3$ wherein Y$^2$ is (C$_1$-C$_4$) alkyl and Y$^3$ is (C$_1$-C$_6$)alkyl; carboxy (C$_1$-C$_6$)alkyl; amino(C$_1$-C$_4$)alkyl or mono-N— or di-N,N-(C$_1$-C$_6$)alkylaminoalkyl; —C(Y$^4$)Y$^5$ wherein Y$^4$ is H or methyl and Y$^5$ is mono-N— or di-N,N—(C$_1$-C$_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted withours, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol. One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.* , 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Spirocyclic Heterocycle Compounds can form salts which are also within the scope of this invention. Reference to a Spirocyclic Heterocycle Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Spirocyclic Heterocycle Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Spirocyclic Heterocycle Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Spirocyclic Heterocycle Compounds may be atropisomers (e.g., substituted biaryls) and are considered as part of this invention. Enantiomers can also be directly separated using chiral chromatographic techniques.

It is also possible that the Spirocyclic Heterocycle Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Spirocyclic Heterocycle Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Spirocyclic Heterocycle Compounds are useful in human and veterinary medicine for treating or preventing HIV infection in a subject. In one embodiment, the Spirocyclic Heterocycle Compounds can be inhibitors of HIV viral replication. In a specific embodiment, the Spirocyclic Heterocycle Compounds are inhibitors of HIV-1. Accordingly, the Spirocyclic Heterocycle Compounds are useful for treating HIV infections and AIDS. In accordance with the invention, the Spirocyclic Heterocycle Compounds can be administered to a subject in need of treatment or prevention of HIV infection.

Accordingly, in one embodiment, the invention provides methods for treating HIV infection in a subject comprising administering to the subject an effective amount of at least one Spirocyclic Heterocycle Compound or a pharmaceutically acceptable salt thereof. In a specific embodiment, the present invention provides methods for treating AIDS in a subject comprising administering to the subject an effective amount of at least one Spirocyclic Heterocycle Compound or a pharmaceutically acceptable salt thereof.

The following abbreviations are used below and have the following meanings: Ac is acetyl or —C(O)CH$_3$, Bu is butyl; Boc$_2$O is di-tert-butyl dicarbonate, DCM is dichloromethane, Dess-Martin Periodinane is 1,1,1-triacetoxy-1,1-dihydro-1,2-benziodoxol-3(1H)-one, DIAD is diisopropyl azodicarboxylate, DIPEA is N,N-diisopropylethylamine, DMF is N,N-dimethylformamide, EtOAc is ethyl acetate, EtOH is ethanol, HATU is 1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin-1-ylmethylene]-N-methylmethanaminium hexafluorophosphate N-oxide, HPLC is high-pressure liquid chromatography, LCMS is liquid chromatography-mass spectrometry, LiHMDS is lithum hexamethyldisilazane, MeOH is methanol, NBS is N-bromosuccinimide, NHS is normal human serum, NMR is nuclear magnetic resonance spectroscopy, Pd/C is palladium on carbon, Pd(Ph$_3$P)$_4$ is tetrakis (triphenylphosphine) palladium(0), PyClu is 1-(chloro-1-pyrrolidinylmethylene)pyrrolidinium hexafluorophosphate, PySO$_3$ is sulfur trioxide-pyridine complex, TLC is thin-layer chromatography and THF is tetrahydrofuran.

The Compounds of Formula (I)

The present invention provides Spirocyclic Heterocycle Compounds of Formula

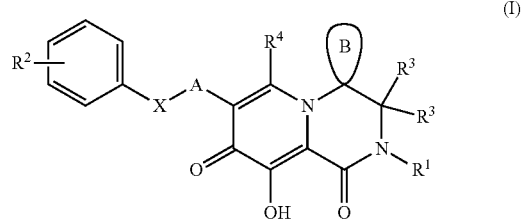

(I)

and pharmaceutically acceptable salts thereof, wherein A, B, X, R$^1$, R$^2$, R$^3$ and R$^4$ are defined above for the Compounds of Formula (I).

In one embodiment, X is —CH$_2$—.

In another embodiment, X is —CH(CH$_3$)—.

In one embodiment, the compounds of formula (I) have the formula (Ia):

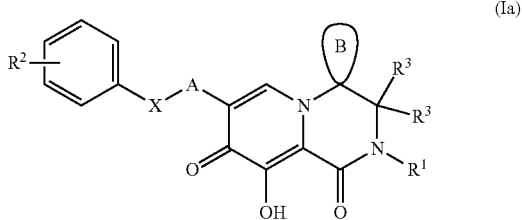

(Ia)

or a pharmaceutically acceptable salt thereof,
wherein:
A is: —NHC(O)— or thiadiazolyl;
B is 4 to 7-membered monocyclic heterocycloalkyl;
R$^1$ is selected from C$_1$-C$_6$ alkyl, —N(C$_1$-C$_6$ alkyl)$_2$, C$_1$-C$_6$ hydroxyalkyl and —(C$_1$-C$_4$ alkylene)-O—(C$_1$-C$_6$ alkyl);
R$^2$ represents up to 2 optional substituents, each independently selected from halo; and
each occurrence of R$^3$ is independently H or C$_1$-C$_6$ alkoxy.

In one embodiment, for the compounds of formula (I) or (Ia), A is —NHC(O)—.

In another embodiment, for the compounds of formula (I) or (Ia), A is 5- or 6-membered monocyclic heterocycloalkyl.

In another embodiment, for the compounds of formula (I) or (Ia), A is a 5-membered monocyclic heterocycloalkyl.

In yet another embodiment, for the compounds of formula (I) or (Ia), A is thiadiazolyl.

In another embodiment, for the compounds of formula (I) or (Ia), A is:

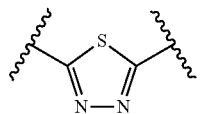

In one embodiment, for the compounds of formula (I) or (Ia), B is a 4-membered monocyclic heterocycloalkyl group.

In another embodiment, for the compounds of formula (I) or (Ia), B is a 5-membered monocyclic heterocycloalkyl group.

In another embodiment, for the compounds of formula (I) or (Ia), B is a 6-membered monocyclic heterocycloalkyl group.

In one embodiment, for the compounds of formula (I) or (Ia), B is selected from:

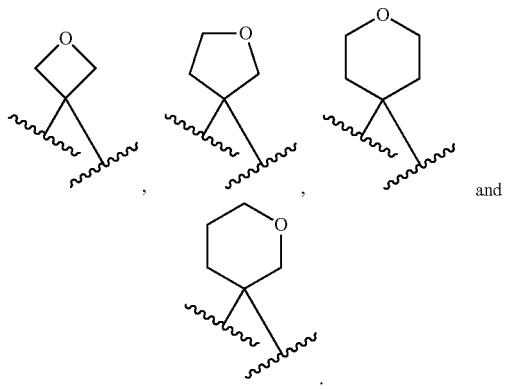

In one embodiment, for the compounds of formula (I) or (Ia), $R^1$ is $C_1$-$C_6$ alkyl.

In another embodiment, for the compounds of formula (I) or (Ia), $R^1$ is —($C_1$-$C_4$ alkylene)-O—($C_1$-$C_6$ alkyl).

In another embodiment, for the compounds of formula (I) or (Ia), $R^1$ is —N($C_1$-$C_6$ alkyl)$_2$.

In another embodiment, for the compounds of formula (I) or (Ia), $R^1$ is selected from methyl, ethyl, —N(CH$_3$)$_2$, —CH$_2$OCH$_3$, —CH$_2$CH$_2$OCH$_3$, —CH$_2$CH$_2$CH$_2$OCH$_3$ and —CH$_2$CH$_2$OCH$_2$CH$_3$.

In one embodiment, for the compounds of formula (I) or (Ia), each occurrence of $R^2$ is halo.

In another embodiment, for the compounds of formula (I) or (Ia), $R^2$ represents up to 3 substituent groups, each independently selected from F and Cl.

In another embodiment, for the compounds of formula (I) or (Ia), $R^2$ represents 2 fluoro groups.

In another embodiment, for the compounds of formula (I) or (Ia), $R^2$ represents 2 fluoro groups, consisting of one fluoro group in the ortho position and the second fluoro group in the para position on the phenyl ring to which they are each attached.

In one embodiment, for the compounds of formula (I) or (Ia), $R^2$ and the phenyl group to which $R^2$ is attached is selected from:

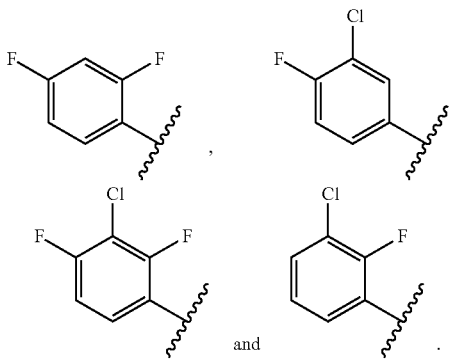

In one embodiment, for the compounds of formula (I) or (Ia), at least one occurrence of $R^3$ is H.

In another embodiment, for the compounds of formula (I) or (Ia), each occurrence of $R^3$ is H.

In another embodiment, for the compounds of formula (I) or (Ia), each occurrence of $R^3$ is other than H.

In one embodiment, for the compounds of formula (I) or (Ia), one occurrence of $R^3$ is H and the other occurrence of $R^3$ is H or —O—($C_1$-$C_6$ alkyl).

In another embodiment, for the compounds of formula (I) or (Ia), one occurrence of $R^3$ is H and the other of $R^3$ is H or methoxy.

In another embodiment, for the compounds of formula (I) or (Ia), one occurrence of $R^3$ is H and the other occurrence of $R^3$ is —O—($C_1$-$C_6$ alkyl).

In still another embodiment, for the compounds of formula (I) or (Ia), one occurrence of $R^3$ is H and the other occurrence of $R^3$ is methoxy.

In one embodiment, for the compounds of formula (I) or (Ia), $R^1$ is $C_1$-$C_6$ alkyl or —($C_1$-$C_4$ alkylene)-O—($C_1$-$C_6$ alkyl); one occurrence of $R^3$ is H; and the other occurrence of $R^3$ is H or —O—($C_1$-$C_6$ alkyl).

In another embodiment, for the compounds of formula (I) or (Ia), $R^1$ is selected from methyl, ethyl, —N(CH$_3$)$_2$, —CH$_2$OCH$_3$, —CH$_2$CH$_2$OCH$_3$, —CH$_2$CH$_2$CH$_2$OCH$_3$ and —CH$_2$CH$_2$OCH$_2$CH$_3$; one occurrence of $R^3$ is H; and the other occurrence of $R^3$ is methoxy.

In one embodiment, for the compounds of formula (I) or (Ia), $R^1$ is $C_1$-$C_6$ alkyl or —($C_1$-$C_4$ alkylene)-O—($C_1$-$C_6$ alkyl); $R^2$ represents up to 3 substituent groups, each independently selected from F and Cl; one occurrence of $R^3$ is H; and the other occurrence of $R^3$ is H or —O—($C_1$-$C_6$ alkyl); A is —NHC(O)—; and B is selected from:

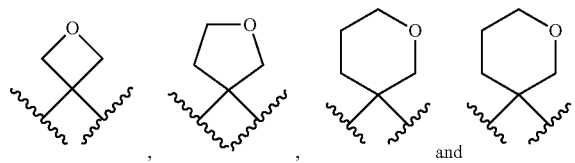

In another embodiment, for the compounds of formula (I) or (Ia), $R^1$ is selected from methyl, ethyl, —N(CH$_3$)$_2$, —CH$_2$OCH$_3$, —CH$_2$CH$_2$OCH$_3$, —CH$_2$CH$_2$CH$_2$OCH$_3$ and —CH$_2$CH$_2$OCH$_2$CH$_3$; one occurrence of $R^3$ is H; and the other occurrence of $R^3$ is methoxy; A is —NHC(O)—; and B is selected from:

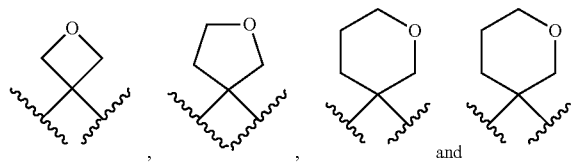

In one embodiment, variables A, B, X, $R^1$, $R^2$, $R^3$ and $R^4$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraphours, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments. The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-58 as set forth in the table below, and pharmaceutically acceptable salts thereof An embodiment of the invention includes a compound selected from compounds 1-58.

| Compound Number | Structure |
|---|---|
| 1 | 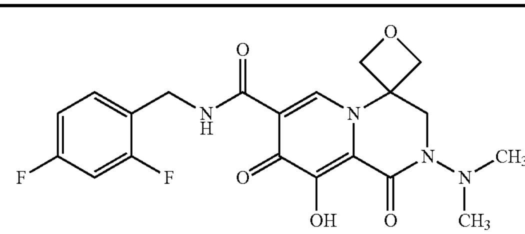 |

-continued
| Compound Number | Structure |
|---|---|
| 2 | 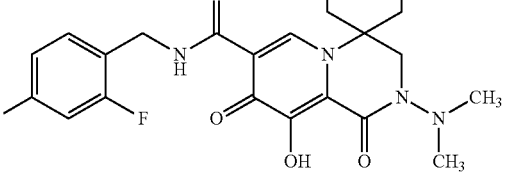 |
| 3 | 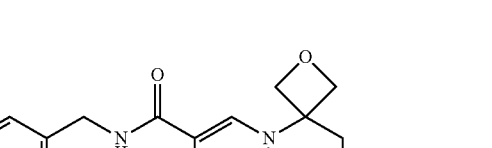 |
| 4 | 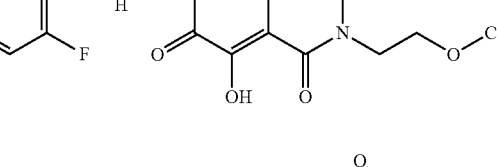 |
| 5 | 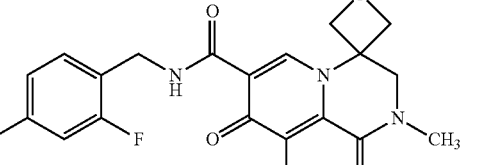 |
| 6 | 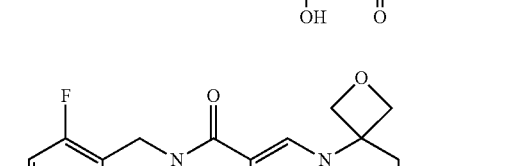 |
| 7 | 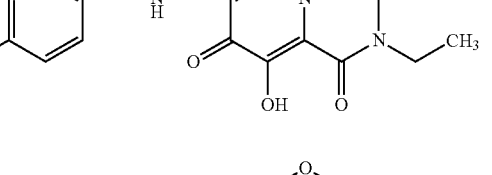 |

-continued
| Compound Number | Structure |
|---|---|
| 8 | 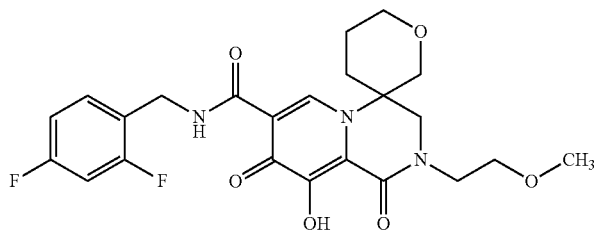<br>Enantiomer A |
| 9 | 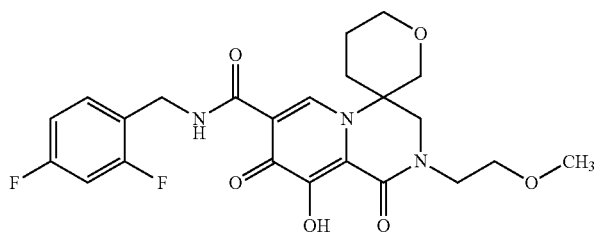<br>Enantiomer B |
| 10 | 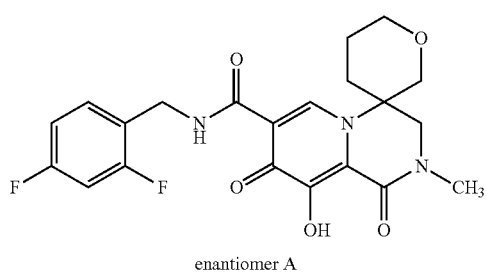 [SMILES: CN1CC2(CCCOC2)n2cc(C(=O)NCc3ccc(F)cc3F)c(=O)c(O)c2C1=O]<br>enantiomer A |
| 11 | 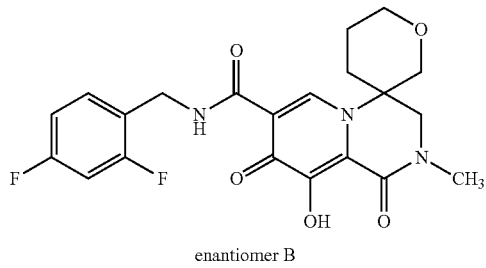 [SMILES: CN1CC2(CCCOC2)n2cc(C(=O)NCc3ccc(F)cc3F)c(=O)c(O)c2C1=O]<br>enantiomer B |
| 12 | 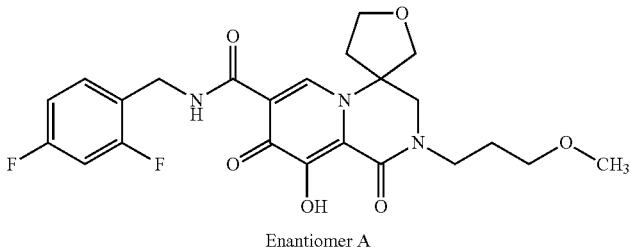 [SMILES: COCCCN1CC2(CCOC2)n2cc(C(=O)NCc3ccc(F)cc3F)c(=O)c(O)c2C1=O]<br>Enantiomer A |

-continued
| Compound Number | Structure |
|---|---|
| 13 | 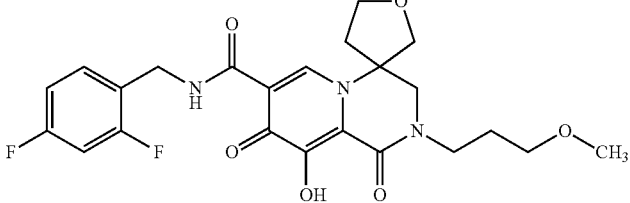<br>Enantiomer B |
| 14 | 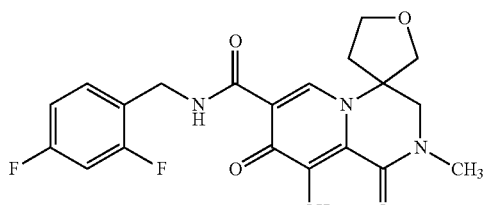<br>enantiomer A |
| 15 | 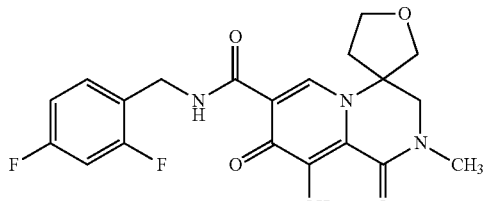<br>enantiomer B |
| 16 | 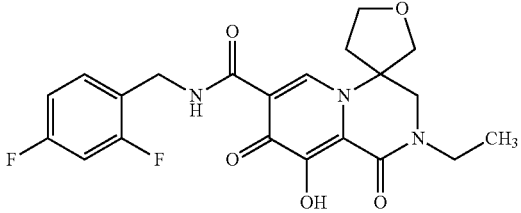<br>enantiomer A |
| 17 | 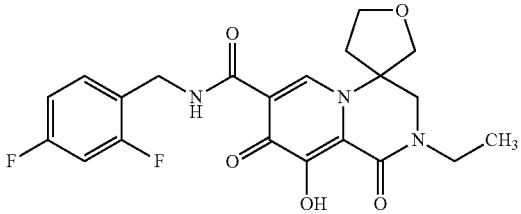<br>enantiomer B |
| 18 | 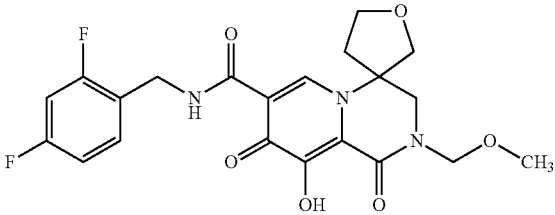<br>enantiomer A |

-continued
| Compound Number | Structure |
|---|---|
| 19 | 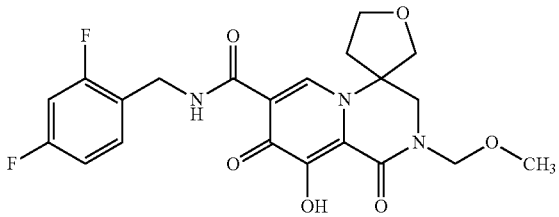
enantiomer B |
| 20 | 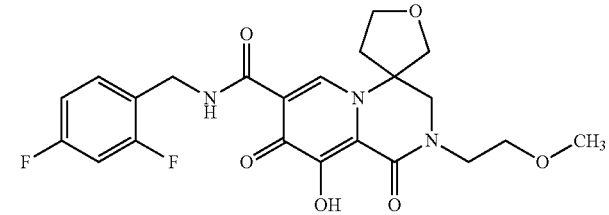
enantiomer A |
| 21 | 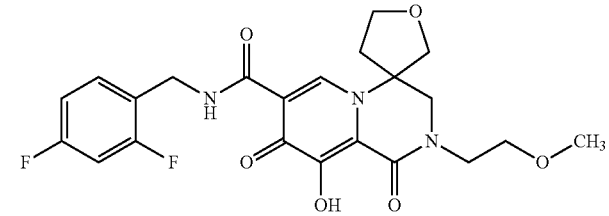
enantiomer B |
| 22 | 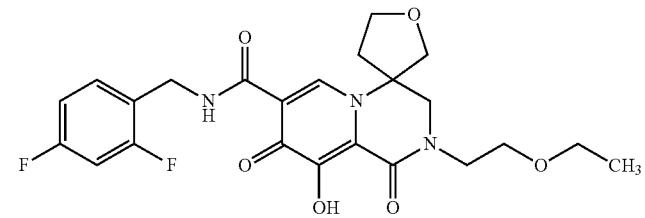
enantiomer A |
| 23 | 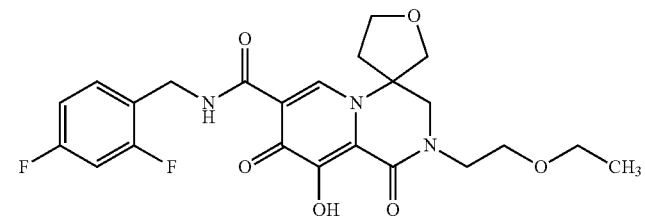
enantiomer B |
| 24 | 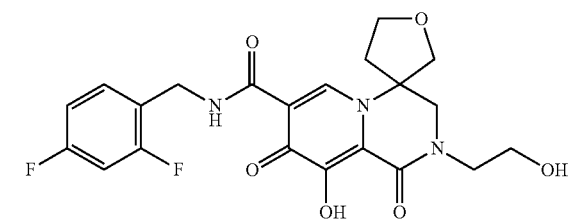 [SMILES: O=C(NCc1ccc(F)cc1F)c1cn2c(c(O)c1=O)C(=O)N(CCO)CC21CCOC1] |

-continued
| Compound Number | Structure |
|---|---|
| 25 | 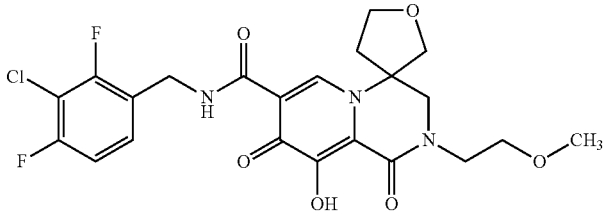<br>enantiomer A |
| 26 | 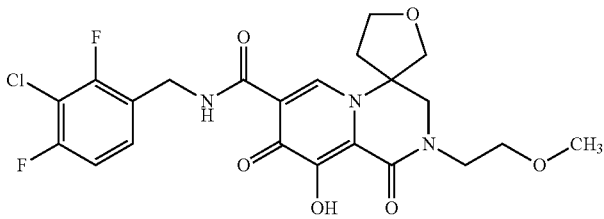<br>enantiomer B |
| 27 | 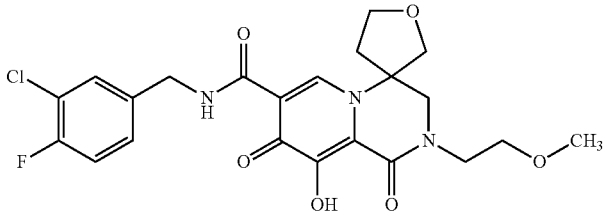<br>enantiomer A |
| 28 | 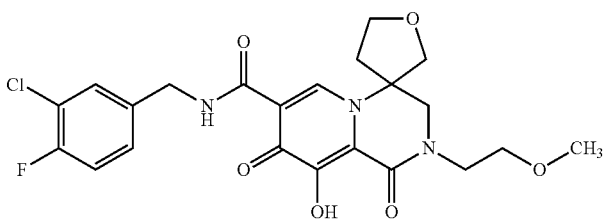<br>enantiomer B |
| 29 | 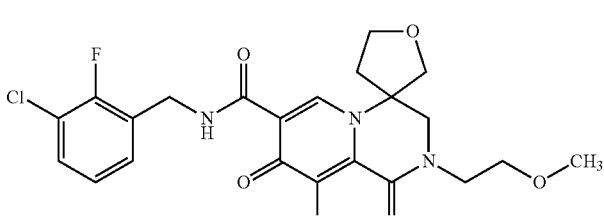<br>enantiomer A |
| 30 | 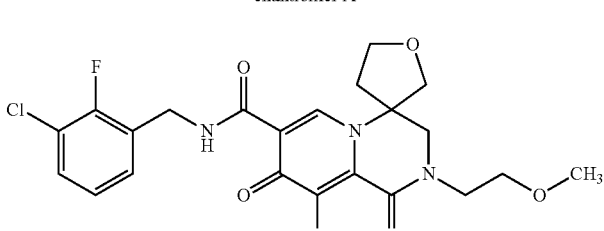<br>enantiomer B |

-continued
| Compound Number | Structure |
|---|---|
| 31 | 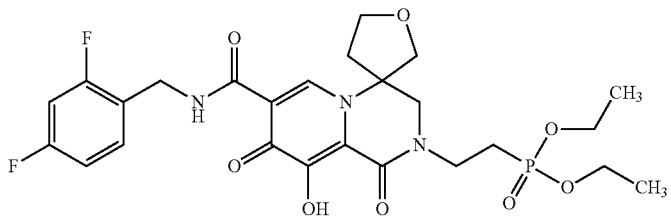 [SMILES: CCOP(=O)(CCN1CC2(CCOC2)n2cc(C(=O)NCc3ccc(F)cc3F)c(=O)c(O)c2C1=O)OCC] |
| 32 | 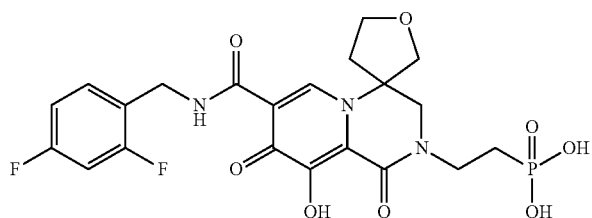 [SMILES: O=C(NCc1ccc(F)cc1F)c1cn2c(c(O)c1=O)C(=O)N(CCP(=O)(O)O)CC21CCOC1] |
| 33 | 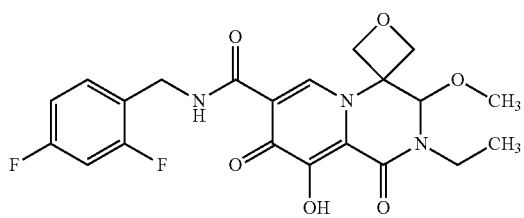<br>Enantiomer A |
| 34 | 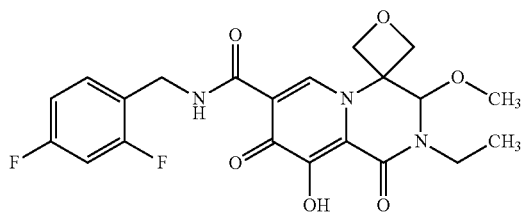<br>Enantiomer B |
| 35 | 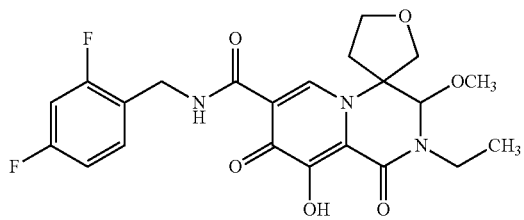<br>Diastereomer B, racemic |
| 36 | 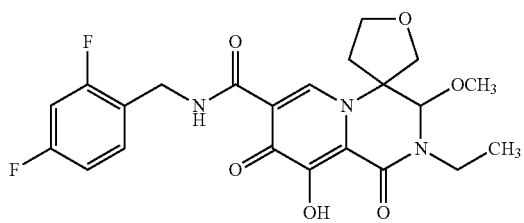<br>Diastereomer A, Enantiomer A |

-continued
| Compound Number | Structure |
|---|---|
| 37 | 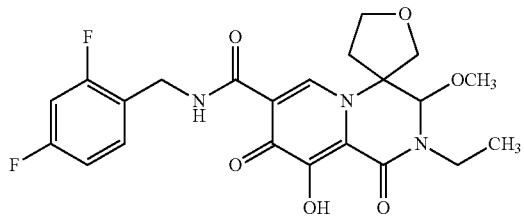<br>Diastereomer A, Enantiomer A |
| 38 | 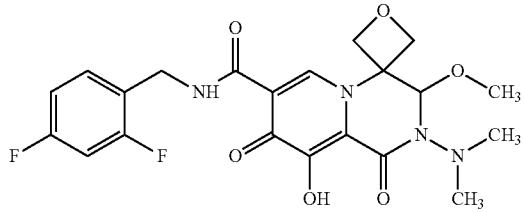 [SMILES: COC1N(N(C)C)C(=O)c2c(O)c(=O)c(C(=O)NCc3ccc(F)cc3F)cn2C12COC2] |
| 39 | 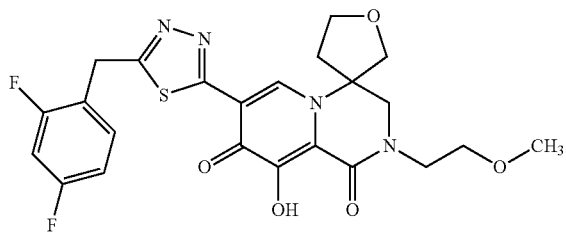<br>Enantiomer A |
| 40 | 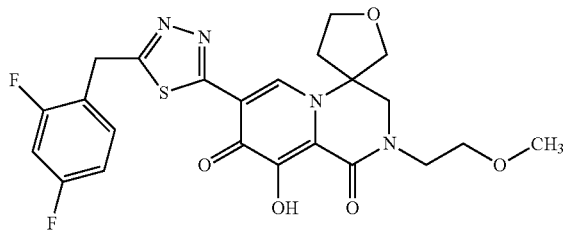<br>Enantiomer B |
| 45 | 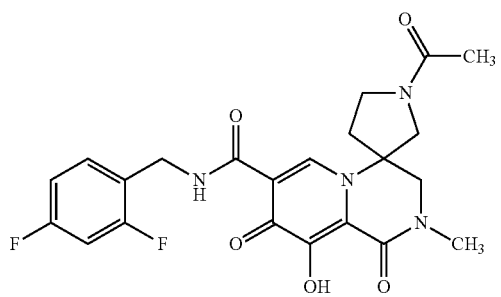<br>Enantiomer A |

-continued
| Compound Number | Structure |
|---|---|
| 46 | 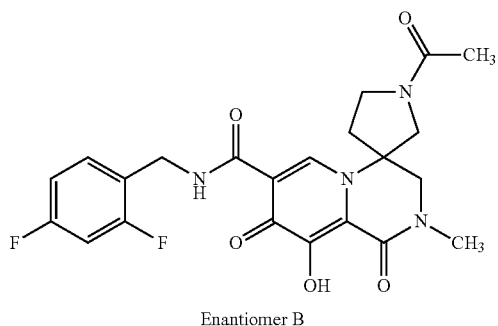 [SMILES: CC(=O)N1CCC2(CN(C)C(=O)c3c(O)c(=O)c(C(=O)NCc4ccc(F)cc4F)cn32)C1]<br>Enantiomer B |
| 47 | 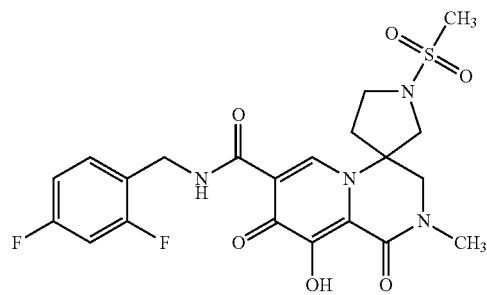<br>Enantiomer A |
| 48 | 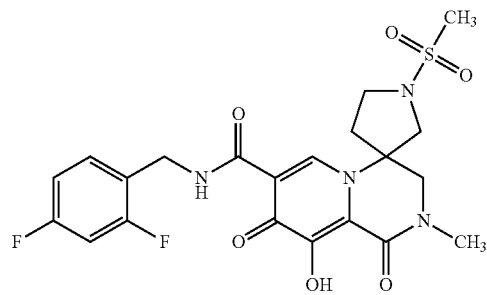<br>Enantiomer B |
| 49 | 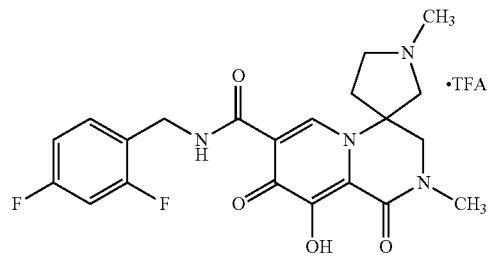<br>Enantiomer A |

| Compound Number | Structure |
|---|---|
| 50 | 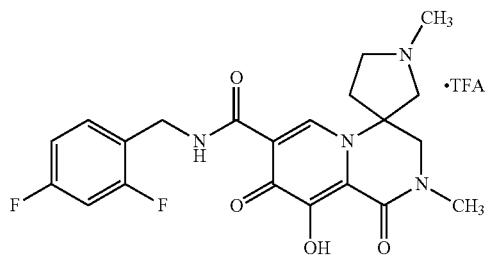<br>Enantiomer B |
| 51 | 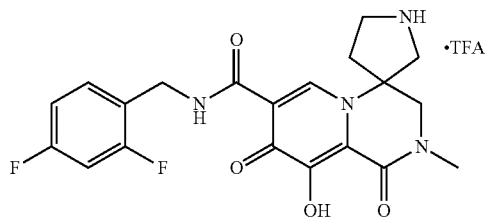<br>Enantiomer A |
| 52 | 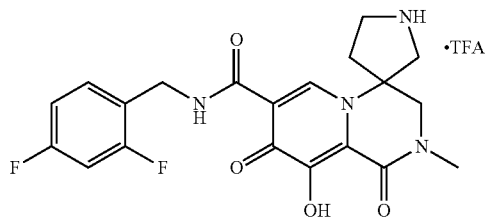<br>Enantiomer B |
| 53 | 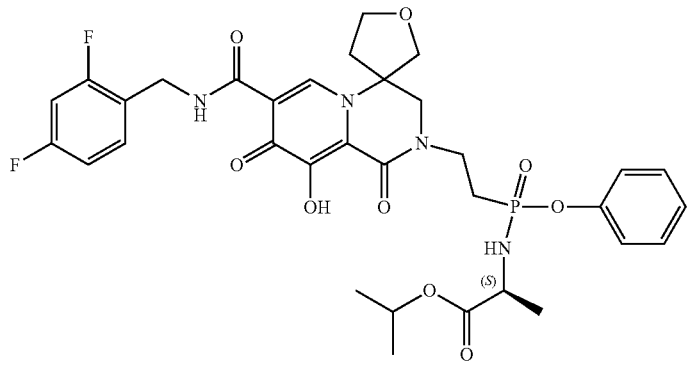<br>mixture of 4 diastereomers |

| Compound Number | Structure |
|---|---|
| 54 | 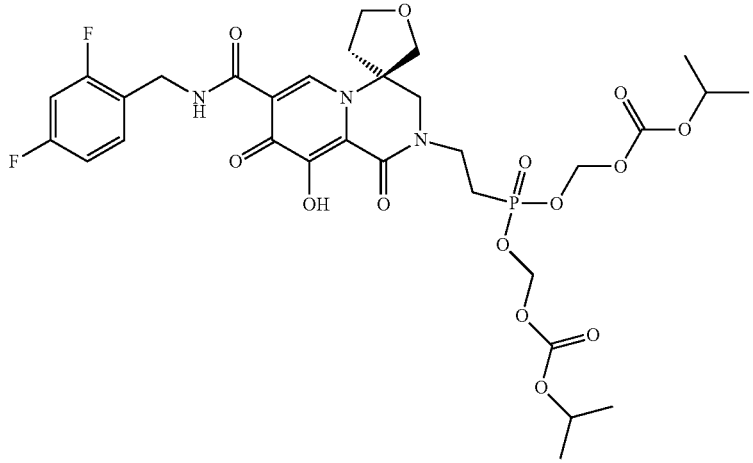<br>Enantiomer A |
| 55 | 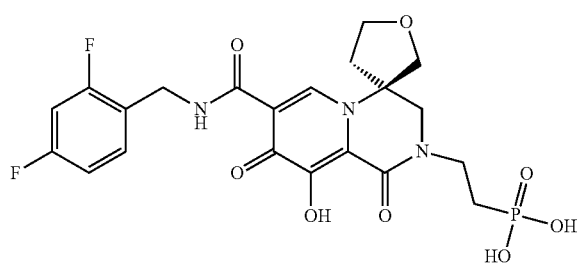<br>Enantiomer A |
| 56 | 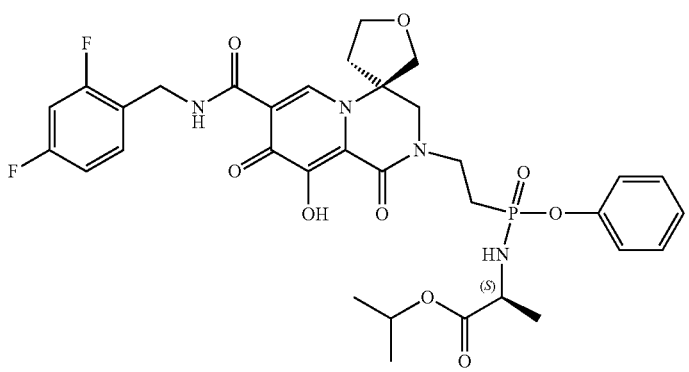<br>Enantiomer A, epimers at P, mixture of 2 stereoisomers |
| 57 | 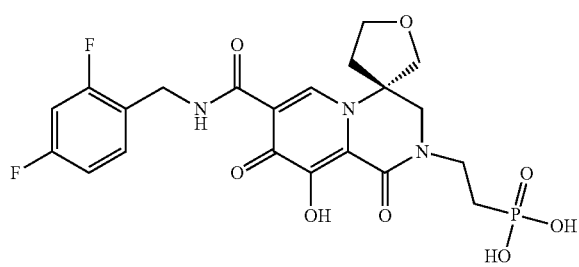<br>Enantiomer B |

| Compound Number | Structure |
|---|---|
| 58 | 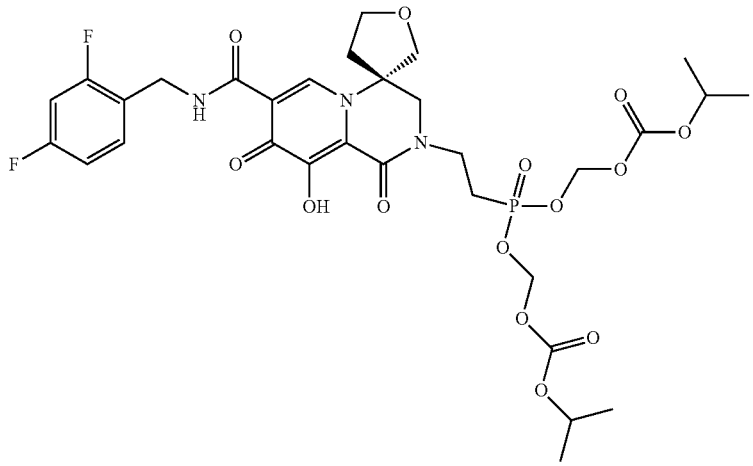<br>Enantiomer B |

Treatment or Prevention of HIV Infection

The Spirocyclic Heterocycle Compounds are useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Spirocyclic Heterocycle Compounds are useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Spirocyclic Heterocycle Compound or a pharmaceutically acceptable salt thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Spirocyclic Heterocycle Compounds are also useful in the preparation and execution of screening assays for antiviral compounds. For example the Spirocyclic Heterocycle Compounds are useful for identifying resistant HIV cell lines harboring mutations, which are excellent screening tools for more powerful antiviral compounds. Furthermore, the Spirocyclic Heterocycle Compounds are useful in establishing or determining the binding site of other antivirals to the HIV Integrase.

The compositions and combinations of the present invention can be useful for treating a subject suffering from infection related to any HIV genotype.

Combination Therapy

In another embodiment, the present methods for treating or preventing HIV infection can further comprise the administration of one or more additional therapeutic agents which are not Spirocyclic Heterocycle Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Spirocyclic Heterocycle Compound (which may include two or more different Spirocyclic Heterocycle Compounds), or a pharmaceutically acceptable salt thereof, and (ii) at least one additional therapeutic agent that is other than a Spirocyclic Heterocycle Compound, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Spirocyclic Heterocycle Compound and an additional therapeutic agent may be present in fixed amounts (dosage amounts) in a single dosage unit (e.g., a capsule, a tablet and the like).

In one embodiment, the at least one Spirocyclic Heterocycle Compound is administered during a time when the additional therapeutic agent(s) exert their prophylactic or therapeutic effect, or vice versa.

In another embodiment, the at least one Spirocyclic Heterocycle Compound and the additional therapeutic agent(s) are administered in doses commonly employed when such agents are used as monotherapy for treating a viral infection.

In another embodiment, the at least one Spirocyclic Heterocycle Compound and the additional therapeutic agent(s) are administered in doses lower than the doses commonly employed when such agents are used as monotherapy for treating a viral infection.

In still another embodiment, the at least one Spirocyclic Heterocycle Compound and the additional therapeutic agent(s) act synergistically and are administered in doses lower than the doses commonly employed when such agents are used as monotherapy for treating a viral infection.

In one embodiment, the at least one Spirocyclic Heterocycle Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HIV infection.

In another embodiment, the viral infection is AIDS.

The at least one Spirocyclic Heterocycle Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Spirocyclic Heterocycle Compound and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |

TABLE A-continued

| Name | Type |
|---|---|
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | InI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, dolutegravir, darunavir, atazanavir, emtricitabine, tenofovir, elvitegravir, rilpivirine and lopinavir.

In another embodiment, the compound of formula (I) is used in combination with a single anti-HIV drug which is raltegravir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In yet another embodiment, the compound of formula (I) is used in combination with a single anti-HIV drug which is dolutegravir.

In another embodiment, the compound of formula (I) is used in combination with a single anti-HIV drug which is elvitegravir.

In one embodiment, the compound of formula (I) is used in combination with two anti-HIV drugs which are lamivudine and abacavir.

In another embodiment, the compound of formula (I) is used in combination with two anti-HIV drugs which are darunavir and raltegravir.

In another embodiment, the compound of formula (I) is used in combination with two anti-HIV drugs which are emtricitabine and tenofovir.

In still another embodiment, the compound of formula (I) is used in combination with two anti-HIV drugs which are atazanavir and raltegravir.

In another embodiment, the compound of formula (I) is used in combination with two anti-HIV drugs which are ritonavir and lopinavir.

In another embodiment, the compound of formula (I) is used in combination with two anti-HIV drugs which are lamivudine and raltegravir.

In one embodiment, the compound of formula (I) is used in combination with three anti-HIV drug which are abacavir, lamivudine and raltegravir.

In another embodiment, the compound of formula (I) is used in combination with three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV agents selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV agents selected from lamivudine, abacavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Spirocyclic Heterocycle Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Compositions and Administration

When administered to a subject, the Spirocyclic Heterocycle Compounds can be administered as a component of a composition that comprises a pharmaceutically acceptable carrier or vehicle. The present invention provides pharmaceutical compositions comprising an effective amount of at least one Spirocyclic Heterocycle Compound and a pharmaceutically acceptable carrier. In the pharmaceutical compositions and methods of the present invention, the active ingredients will typically be administered in admixture with suitable carrier materials suitably selected with respect to the intended form of administration, L e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starchours, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starchours, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starchours, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Spirocyclic Heterocycle Compounds are administered orally.

In another embodiment, the one or more Spirocyclic Heterocycle Compounds are administered intravenously.

In one embodiment, a pharmaceutical preparation comprising at least one Spirocyclic Heterocycle Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Spirocyclic Heterocycle Compound(s) by weight or volume. In various embodiments, the present compositions can contain, in one embodiment, from about 1% to about 70% or from about 5% to about 60% of the Spirocyclic Heterocycle Compound(s) by weight or volume.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general healthours, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Spirocyclic Heterocycle Compounds will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Spirocyclic Heterocycle Compound, or a pharmaceutically acceptable salt or prodrug of said compound and a pharmaceutically acceptable carrier, vehicle or diluent.

In another aspect the present invention provides a kit comprising an amount of at least one Spirocyclic Heterocycle Compound, or a pharmaceutically acceptable salt or prodrug of said compound and an amount of at least one additional therapeutic agent listed above, wherein the amounts of the two or more active ingredients result in a desired therapeutic effect. In one embodiment, the one or more Spirocyclic Heterocycle Compounds and the one or more additional therapeutic agents are provided in the same container. In one embodiment, the one or more Spirocyclic Heterocycle Compounds and the one or more additional therapeutic agents are provided in separate containers.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Scheme 1 below. Alternative synthetic pathways and analogous structures will be apparent to those skilled in the art of organic synthesis.

Scheme 1 describes methods useful for making the Compounds of Formula (I).

Scheme 1

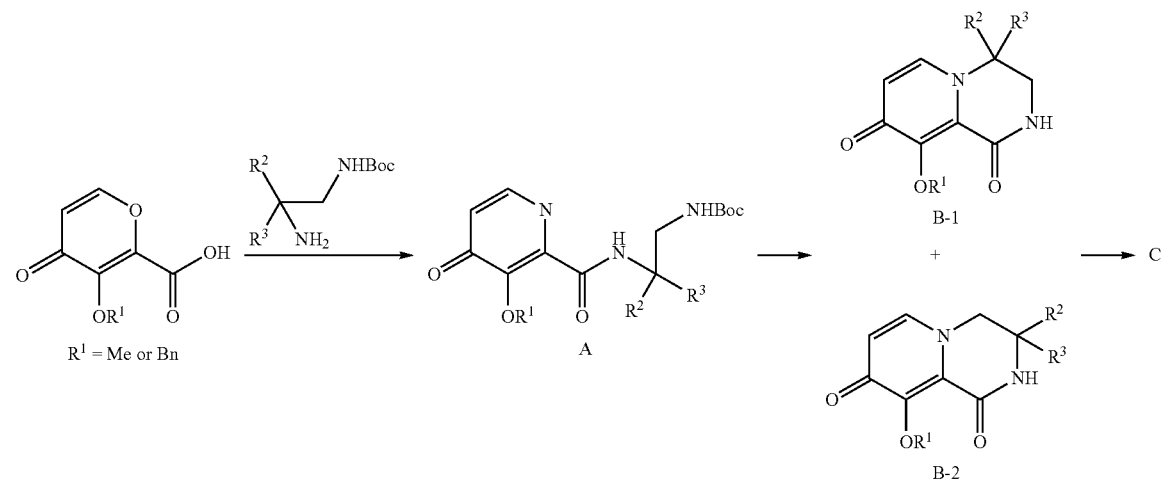

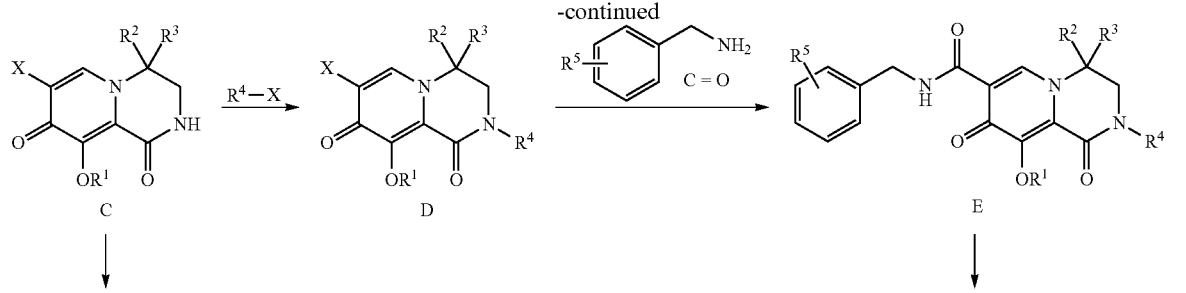

C → D → E

F

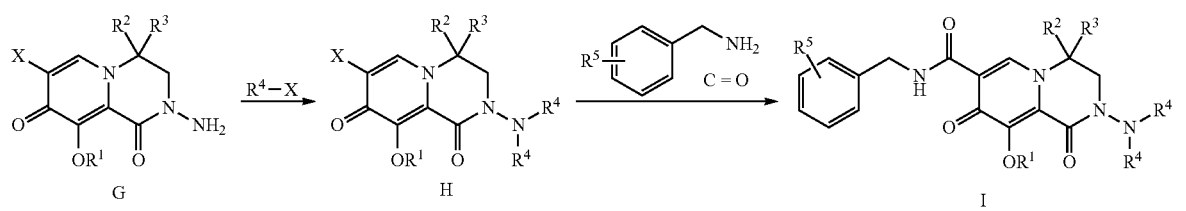

G → H → I

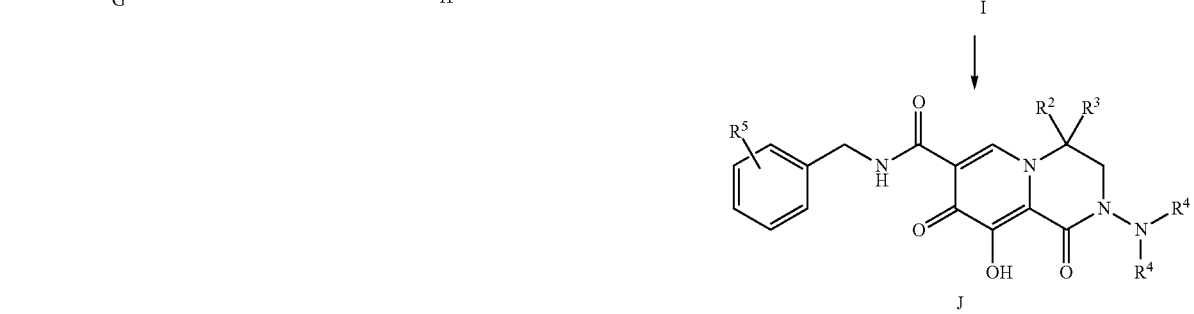

J

Compounds of Formula (I) can be prepared as shown in Scheme 1 from a 3-hydroxy-4-oxo-4H-pyran-2-carboxylic acid that is mono-protected as the 3-methoxy- or 3-benzyloxy ether ($R^1$=Me or Bn) and a suitably funtionalized 1,2-vicinal diamine which are converted to compound A by standard coupling techniques. Compound A is then deprotected and subjected to cyclization conditions to provide a mixture of structural isomers B-1 and B-2 that are separated by standard chromatography techniques. Halogen transfer to compound B-1 affords compound C (X=I or Br or Cl). Compound C is then alkylated to provide compound D which is then carbonylated with a transition metal catalyst system in the presence of a suitably functionalized amine and carbon monoxide to provide Compound E. Deprotection of Compound E affords final compound F.

An additional variation involves amino transfer to compound C which affords compound G. Alkylation of compound G affords compound H which is subjected to carbonylated with a transition metal catalyst system in the presence of a suitably functionalized amine and carbon monoxide to provide Compound I. Deprotection of Compound I affords final compound J.

Scheme 2

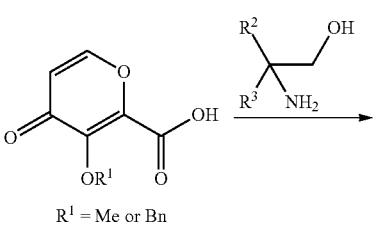

$R^1$ = Me or Bn

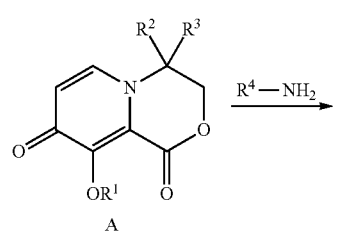

A

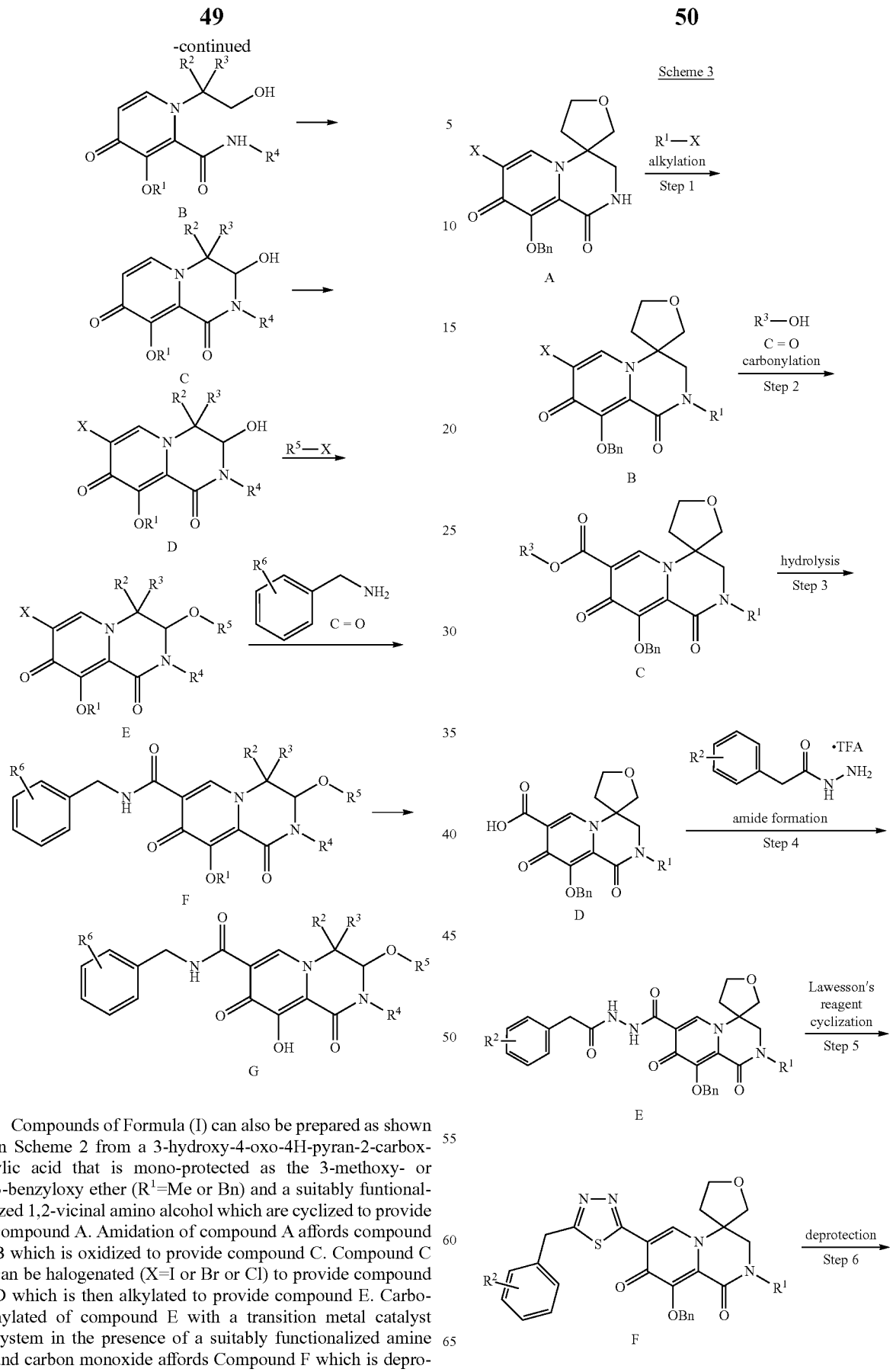

Compounds of Formula (I) can also be prepared as shown in Scheme 2 from a 3-hydroxy-4-oxo-4H-pyran-2-carboxylic acid that is mono-protected as the 3-methoxy- or 3-benzyloxy ether ($R^1$=Me or Bn) and a suitably funtionalized 1,2-vicinal amino alcohol which are cyclized to provide compound A. Amidation of compound A affords compound B which is oxidized to provide compound C. Compound C can be halogenated (X=I or Br or Cl) to provide compound D which is then alkylated to provide compound E. Carbonylated of compound E with a transition metal catalyst system in the presence of a suitably functionalized amine and carbon monoxide affords Compound F which is deprotected to provide final compound G.

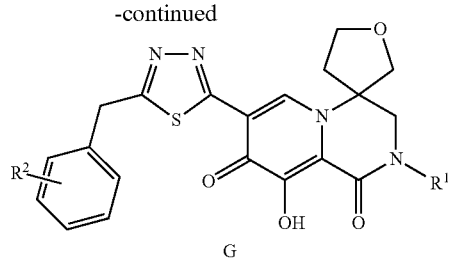

Compounds of Formula (I) can also be prepared as shown in Scheme 3 from a suitably functionalized compound A (X=I or Br or Cl). Alkylation of compound A affords compound B which is then carbonylated with a suitably functionalized alcohol and carbon monoxide in the presence of a transition metal catalyst system to provide compound C. Hydrolysis of compound C affords compound D which is coupled to a suitably functionalized acyl hydrazide under standard amide-formation conditions to provide compound E. A sulfur transfer reagent (e.g., Lawesson's reagent) effects the cyclization of compound E to provide compound F which is deprotected to provide compound G.

EXAMPLES

General Methods

The compounds described herein can be prepared according to the procedures of the following schemes and examples, using appropriate materials and are further exemplified by the following specific examples. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. Concentration refers to the removal of the volatile components at reduced pressure (e.g. rotary evaporation) unless otherwise noted. All temperatures are degrees Celsius unless otherwise noted. Mass spectra (MS) were measured by electrospray ion-mass spectroscopy (ESI) in positive ion detection mode and m/z refers to the [M+H]$^+$ ion unless otherwise noted. $^1$H NMR spectra were recorded at 400-500 MHz at ambient temperature unless otherwise noted. RP-HPLC refers to reverse phase HPLC on C18-functionalized preparative or semi-preparative columns with gradient elution using acetonitrile and water modified with trifluoroacetic acid as eluents and fractions were lyophylized or concentrated by rotary evaporation unless otherwise noted. Compounds described herein were synthesized as the racemates unless otherwise noted in the experimental procedures and compound tables. For stereoisomers, enantiomer A refers to the earlier eluting enantiomer and enantiomer B refers to the later eluting enantiomer at the point of chiral resolution and this nomenclature is maintained through the remainder of a synthetic sequence for a given enantiomeric series despite the possibility that subsequent intermediates and final compounds may have the same or opposite orders of elution.

Example 1

Preparation of Compound 1

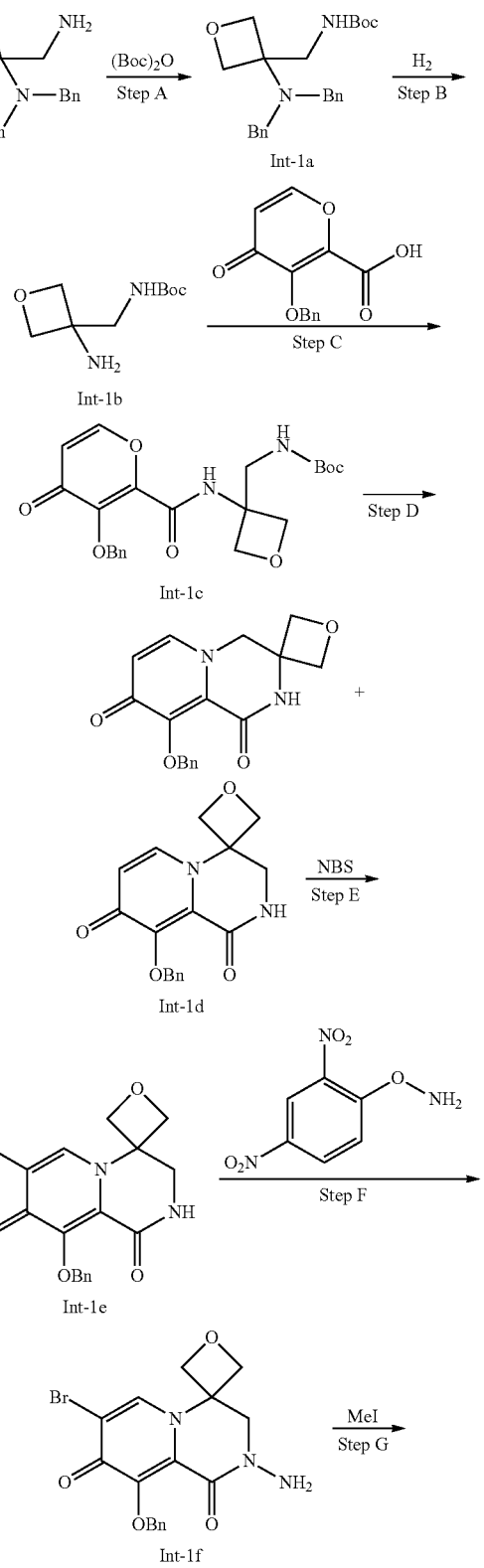

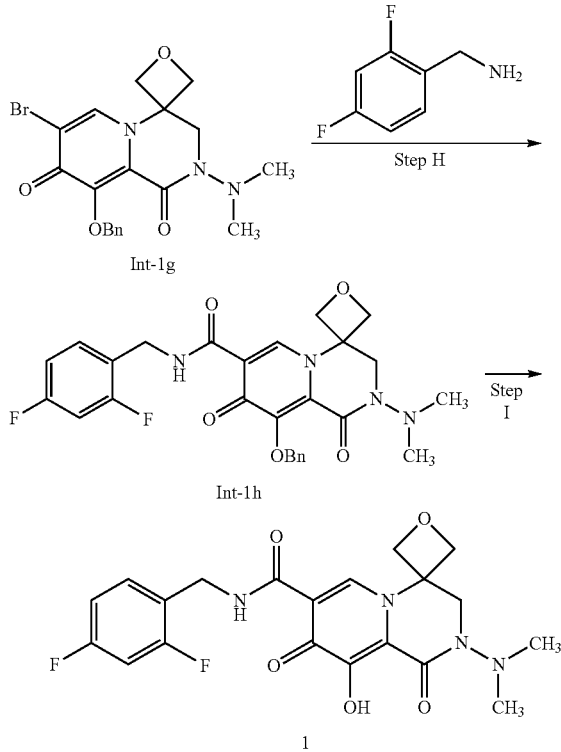

Step A—Synthesis of Intermediate Compound Int-1a

A solution of 3-(aminomethyl)-N,N-dibenzyloxetan-3-amine (5.00 g, 17.7 mmol) in THF (50 mL) was treated with aqueous solution of Na$_2$CO$_3$ (5.63 g, 53.1 mmol) in water (25 mL) and a solution of di-tert-butyl dicarbonate (4.64 g, 21.5 mmol) in THF (10 mL). The mixture was allowed to stir at 20° C. for 5 hours, diluted with water (100 mL) and extracted with dichloromethane (50 mL×3). The organic layer was dried over anhydrous sodium sulfate and filtered. The filtrate was concentrated in vacuo to provide Int-la that was used without further purification. $^1$H NMR (400 MHz, CDCl$_3$) δ 7.21-7.32 (m, 10H), 4.47 (d, J=6.0 Hz, 2H), 4.01 (d, J=6.4 Hz, 2H), 3.76 (d, J=6.0 Hz, 2H), 3.65 (s, 4H), 1.51 (s, 9H).

Step B—Synthesis of Intermediate Compound Int-1b

A solution of Int-1a (5200 mg, 13.59 mmol) in methanol (50 mL) was treated with 20% Pd(OH)$_2$/C (2000 mg, 2.85 mmol) and 0.5 mL trifluoroacetic acid. The mixture was stirred under H$_2$ (1 atm) at 15° C. for 16 hours and then filtered. The filtrate was concentrated in vacuo to provide crude Int-1b, which was used in the next step without further purification. $^1$H NMR (400 MHz, CDCl$_3$) δ 5.17 (s, 1H), 4.46 (d, J=6.0 Hz, 2H), 4.38 (d, J=6.8 Hz, 2H), 3.40-3.45 (m, 2H), 2.28 (s, 2H), 1.41 (s, 9H).

C—Synthesis of Intermediate Compound Int-1c

A solution of 3-(benzyloxy)-4-oxo-4H-pyran-2-carboxylic acid (2400 mg, 9.75 mmol) in N,N-dimethylformamide (30 mL) was treate with PyClu (4570 mg, 12.57 mmol), diisopropylamine (3.4 mL, 19.5 mmol) and Int-1b (2400 mg, 9.75 mmol). The mixture was allowed to stir at 15° C. for 16 hours, diluted with water (50 mL) and extracted with ethyl acetate (30 mL×3). The organic layers were washed with brine (100 mL), dried over anhydrous sodium sulfate, and then filtered. The filtrate was concentrated in vacuo and the resulting residue was purified using column chromatography (petroleum ether: ethyl acetate=1:1) to provide Int-1c. $^1$H NMR (400 MHz, CDCl$_3$) δ 8.11 (s, 1H), 7.81 (d, J=6.0 Hz, 1H), 7.41 (m, 5H), 6.49 (d, J=5.6 Hz, 1H), 5.47 (s, 2H), 4.85 (s, 1H), 4.42 (d, J=6.4 Hz, 2H), 4.25 (d, J=6.4 Hz, 2H), 3.64 (d, J=6.0 Hz, 2H), 1.41 (s, 9H). MS (+ESI) m/z: 431.1.

Step D—Synthesis of Intermediate Compound Int-1d

A solution of Int-1c (2400 mg, 5.58 mmol) in dichloromethane:trifluoroacetic acid=4:1(30 mL) was allowed to stir at 20° C. for 2 hours and then concentrated in vacuo. The crude residue was resolved in ethanol (60 mL), sealed in a microwave tube and irradiated (microwave) with stirring at 90° C. for 2 hours. The mixture was concentrated in vacuo and the resulting residue was purified using preparative TLC on silica gel (dichloromethane:methanol=10:1) to provide Int-1d. $^1$H NMR (400 MHz, CDCl$_3$) δ 7.56 (s, 1H), 7.43 (d, J=6.4 Hz, 2H), 7.21-7.30 (m, 3H), 6.46 (d, J=7.6 Hz, 1H), 5.28 (s, 2H), 4.59 (d, J=7.2 Hz, 2H), 4.36 (d, J=7.2 Hz, 2H), 4.22 (s, 2H). MS (+ESI) m/z: 313.2.

Step E—Synthesis of Intermediate Compound Int-1e

A solution of Int-1d (312 mg, 0.224 mmol) in dichloromethane (3 mL) was treated with N-bromosuccinimide (80 mg, 0.448 mmol) at 0° C. The mixture was allowed to stir at 20° C. for 1 hour and then purified using preparative TLC on silica gel (dichloromethane:methanol=10: 1) to provide Int-1e. $^1$H NMR (400 MHz, methanol-d4) δ 8.73 (s, 1H), 7.49 (d, J=6.4 Hz, 2H), 7.30 (d, J=7.6 Hz, 3H), 5.17 (s, 2H), 5.05 (d, J=8.0 Hz, 2H), 4.63 (d, J=8.4 Hz, 2H), 3.81 (s, 2H). MS (+ESI) m/z: 391.9, 392.9

Step F—Synthesis of Intermediate Compound Int-1f

A solution of Int-1e (105 mg, 0.268 mmol) in N,N-dimethylformamide (2 mL) was treated with cesium carbonate (525 mg, 1.610 mmol), stirred at 20° C. for 30 minutes and then treated with O-(2,4-dinitrophenyl)hydroxylamine (214 mg, 1.074 mmol). The mixture was allowed to stir at 20° C. for 16 hours and quenched with water (30 mL). The volatile components were removed by lyophilization resulting in a yellow solid that was slurried in dichloromethane (150 mL) and filtered. The filtrate was concentrated in vacuo and the resulting residue was purified using preparative TLC on silica gel (dichloromethane: methanol=10:1) to provide Int-1f. $^1$H NMR (400 MHz, methanol-d4) δ 8.70 (s, 1H), 7.52 (m, 2H), 7.32 (m, 3H), 5.17 (s, 2H), 5.05 (d, J=7.6 Hz, 2H), 4.66 (d, J=8.0 Hz, 2H), 4.13 (s, 2H).

Step G—Synthesis of Intermediate Compound Int-1g

A solution of Int-1f (150 mg, 0.334 mmol) in N,N-dimethylformamide (2 mL) was treated with K$_2$CO$_3$ (87 mg, 0.633 mmol) and iodomethane (0.16 mL, 2.53 mmol), stirred at 15° C. for 16 hours, diluted with water (10 mL) and extracted with ethyl acetate (15 mL×3). The combined organic layers were dried over anhydrous sodium sulfate, filtered and concentrated in vacuo. The resulting residue was purified using preparative TLC on silica gel (dichloromethane: methanol=15:1) to provide Int-1g. $^1$H NMR (400 MHz, methanol-d4) δ 8.72 (s, 1H), 7.53 (d, J=6.4 Hz, 2H), 7.27-7.36 (m, 3H), 5.18 (s, 2H), 5.04 (d, J=8.4 Hz, 2H), 4.68 (d, J=8.0 Hz, 2H), 4.10 (s, 2H), 2.73 (s, 6H). MS (+ESI) m/z: 434.0, 436.0.

Step H—Synthesis of Intermediate Compound Int-1h

A solution of Int-1g (12 mg, 0.028 mmol) in dimethylsulfoxide (0.5 mL) and methanol (2.0 mL) were treated with (2,4-difluorophenyl)methanamine (19.78 mg, 0.14 mmol), N,N-diisopropylethylamine (9 μL, 0.06 mmol) and Pd(Ph$_3$P)$_4$ (6.4 mg, 5.5 μmol). The mixture was allowed to stir at 80° C. for 2 hours, cooled to room temperature, diluted with water (10 mL) and extracted with ethyl acetate (15 mL×3). The combined organic layers were washed with 1M HCl (50 mL), dried over anhydrous sodium sulfate, filtered and concentrated in vacuo. The resulting residue was purified using preparative TLC on silica gel (ethyl acetate) to provide Int-1h $^1$H NMR (400 MHz, CDCl$_3$) δ 8.87 (s, 1H), 7.52 (d, J=7.2 Hz, 2H), 7.23-7.36 (m, 5H), 6.69-6.83 (m, 2H), 5.23 (s, 2H), 4.99 (d, J=8.0 Hz, 2H), 4.50-4.61 (m, 4H), 3.93 (s, 2H), 2.78 (s, 6H).

Step I—Synthesis of Compound 1

A solution of Int-1h (8 mg, 18 μmol) in N,N-dimethylformamide (1 mL) was treated with LiCl (2.4 mg, 0.06 mmol). The mixture was allowed to stir at 100° C. for 2 hours, cooled to room temperature, filtered and the filtrate was directly purified using RP-HPLC to provide Compound 1. $^1$H NMR (400 MHz, DMSO-d$_6$) δ 12.66 (s, 1H), 10.32 (s., 1H), 8.72 (s., 1H), 7.36-7.42 (m, 1H), 7.20-7.26 (m, 1H), 7.06 (d, J=10.0 Hz, 1H), 4.89 (d, J=8.0 Hz, 2H), 4.70 (d, J=8.0 Hz, 2H), 4.50-4.58 (m, 2H), 4.17 (s., 2H), 2.67 (s, 6H). MS (+ESI) m/z: 435.1.

The following compound of the present invention was made using the methods described above in Example 1 and substituting the appropriate reactants and reagents:

| Compound Number | Structure | Exact Mass [M + H]$^+$ |
| --- | --- | --- |
| 2 | 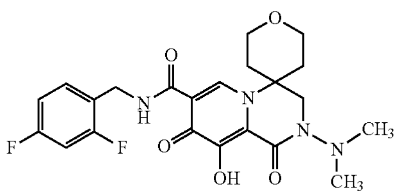 [SMILES: CN(C)N1CC2(CCOCC2)n2cc(C(=O)NCc3ccc(F)cc3F)c(=O)c(O)c2C1=O] | Calc'd 463.2, found 463.1 |

Example 2

Preparation of Compound 3

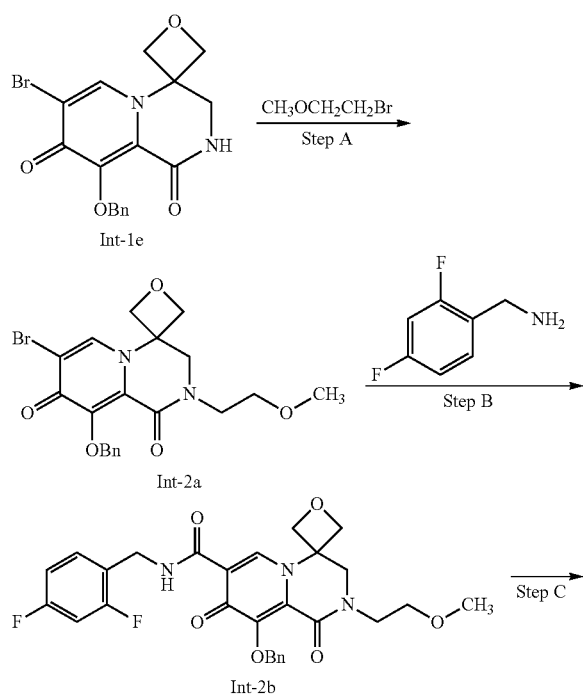

Step A—Synthesis of Intermediate Compound Int-2a

A solution of Int-1e (69 mg, 0.18 mmol) in N,N-dimethylformamide (2 mL) was added Cs$_2$CO$_3$ (172 mg, 0.53 mmol) and 1-bromo-2-methoxyethane (122 mg, 0.87 mmol). The mixture was allowed to stir at 15° C. for 6 hours, diluted with water (15 mL) and extracted with ethyl acetate (10 mL×3). The combined organic layers were washed with brine (50 mL), dried over anhydrous sodium sulfate, filtered and concentrated in vacuo. The resulting residue was purified using preparative TLC on silica gel (dichloromethane:methanol=10:1) to provide Int-2a. $^1$H NMR (400 MHz, CDCl$_3$) δ 8.17 (s, 1H), 8.01 (s, 1H), 7.61 (d, J=7.2 Hz, 2H), 7.29-7.42 (m, 3H), 5.12 (s, 2H), 4.69-4.81 (m, 4H), 4.05 (s, 2H), 3.51 (t, J=4.50 Hz, 2H), 3.38 (t, J=4.4 Hz, 2H), 3.31 (s, 3H). MS (+ESI) m/z: 449.0.

Step B—Synthesis of Intermediate Compound Int-2b

A solution of Int-2a (46 mg, 0.099 mmol) in dimethylsulfoxide (0.5 mL) and methanol (2.0 mL) was treated with (2,4-difluorophenyl)methanamine (112 mg, 0.50 mmol), N,N-diisopropylethylamine (0.05 mL, 0.30 mmol) and Pd(Ph$_3$P)$_4$ (24 mg, 0.020 mmol). The mixture was allowed to stir at 80° C. under carbon monoxide (1 atm) for 6 hours, diluted with water (10 mL) and extracted with ethyl acetate (10 mL×3). The combined organic layers were washed with 1M HCl (30 mL), dried over anhydrous sodium sulfate, filtered and concentrated in vacuo. The resulting residue was purified using preparative TLC on silica gel (dichloromethane:methanol=15:1) to provide Int-2b. $^1$H NMR (400 MHz, methanol-d4) δ 8.93 (s, 1H), 7.42-7.55 (m, 3H), 7.29 (bs, 3H), 6.87-7.01 (m, 2H), 5.12 (s, 2H), 4.95 (d, J=7.6 Hz, 2H), 4.69 (d, J=7.6 Hz, 2H), 4.63 (s, 1H), 4.04 (s, 2H), 3.55-3.70 (m, 4H), 3.34 (s, 3H), 3.29 (s, 2H). MS (+ESI) m/z: 540.2.

Step C—Synthesis of Compound 3

A solution of Int-2b (20 mg, 0.037 mmol) in N,N-dimethylformamide (2 mL) was treated with lithium chloride (16 mg, 0.37 mmol) at rt. The mixture was allowed to stir at 100° C. for 2 hours, cooled to room temperature, filtered and the filtrate was directly purified using RP-HPLC to provide Compound 3. $^1$H NMR (400 MHz, CDCl$_3$) δ 12.59 (s, 1H), 10.38 (s, 1H), 8.89 (s, 1H), 7.34-7.43 (m, 1H), 6.77-6.88 (m, 2H), 5.03 (d, J=7.6 Hz, 2H), 4.67 (d, J=7.2 Hz, 4H), 4.20 (s, 2H), 3.80 (t, J=4.4 Hz, 2H), 3.64-3.71 (m, 2H), 3.39 (s, 3H). MS (+ESI) m/z: 450.1.

The following compounds of the present invention were made using the methods described above in Example 2 and substituting the appropriate reactants and reagents:

| Compound Number | Structure | Exact Mass [M + H]+ |
|---|---|---|
| 4 | 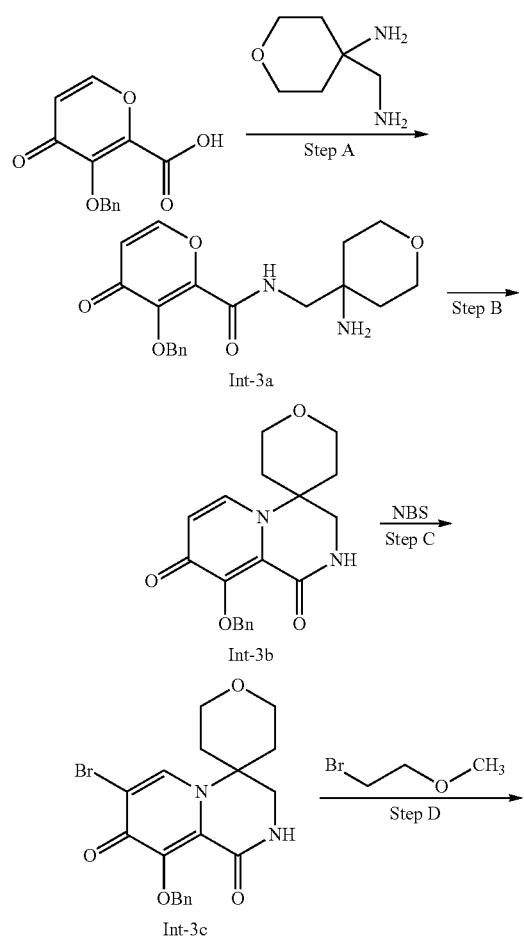 | Calc'd 406.1, found 406.3 |
| 5 | 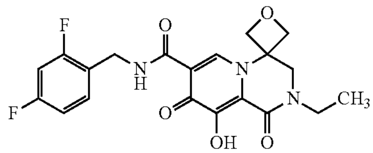 [SMILES: CCN1CC2(COC2)n2cc(C(=O)NCc3ccc(F)cc3F)c(=O)c(O)c2C1=O] | Calc'd 420.1, found 420.1 |

Example 3

Preparation of Compound 6

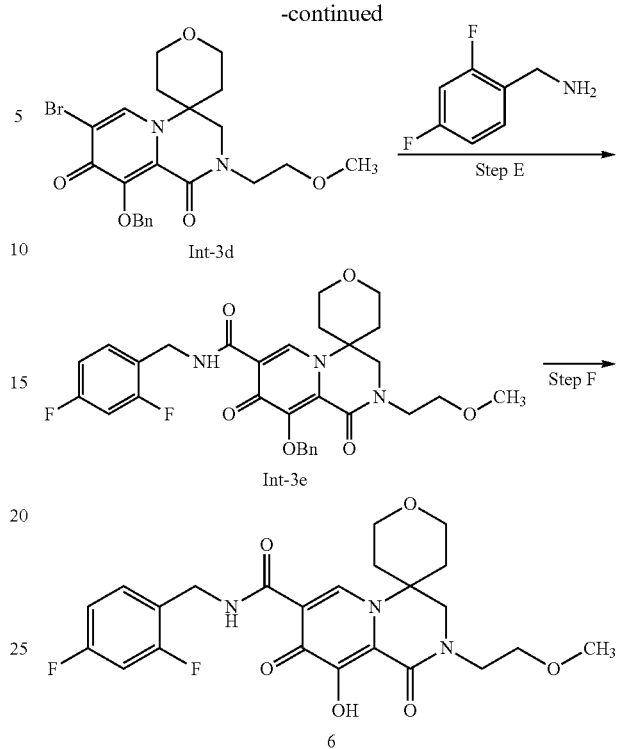

Step A—Synthesis of Intermediate Compound Int-3a

A solution of 3-(benzyloxy)-4-oxo-4H-pyran-2-carboxylic acid (1.1 g, 4.47 mmol), PyClu (1.783 g, 5.36 mmol), 4-(aminomethyl)tetrahydro-2H-pyran-4-amine (0.872 g, 6.70 mmol) and N,N-diisopropylethylamine (1.155 g, 8.94 mmol) in THF (20 mL) was allowed to stir at 15° C. for 3 hours. The mixture was quenched with water (30 mL) and extracted with ethyl acetate (50 mL×3). The combined organic layers were washed with brine (10 mL), dried over anhydrous sodium sulfate, filtered and concentrated in vacuo. The resulting residue was purified using column chromatography on silica gel (dichloromethane/methanol=10/1) to provide Int-3a: $^1$H NMR (400 MHz, CDCl$_3$) δ 8.15 (br, s, 1H), 7.83-7.84 (d, J=5.2 Hz, 1H), 7.37-7.43 (m, 5H), 6.48-6.49 (d, J=5.2 Hz, 1H), 5.45 (s, 2H), 3.61-3.64 (m, 4H), 3.22-3.24 (d, J=6 Hz, 2H), 1.63-1.80 (m, 2H), 1.45-1.51 (m, 2H).

Step B—Synthesis of Intermediate Compound Int-3b

A suspension of Int-3a and NaHCO$_3$ (293 mg, 3.49 mmol) in water (5 mL) was allowed to stir at 100° C. for 3 hours. The reaction mixture was cooled to room temperature and concentrated in vacuo. The resulting residue was purified using preparative TLC on silica gel (dichloromethane/methanol=10/1) to provide Int-3b. $^1$H NMR (400 MHz, methanol-d4) δ 7.68-7.70 (d, J=7.6 Hz, 1H), 7.24-7.34 (m, 5H), 6.51-6.53 (d, J=7.6 Hz, 1H), 5.29 (s, 2H), 4.07 (s, 2H), 3.56-3.66 (m, 4H), 1.52-1.56 (m, 2H), 1.22-1.26 (m, 2H).

Step C—Synthesis of Intermediate Compound Int-3c

A solution of Int-3b (90 mg, 0.21 mmol) in dichloromethane (5 mL) was treated with N-bromosuccinimide (52.3 mg, 0.294 mmol), stirred at 20° C. for 3 hours and concentrated at low temperature. The resulting residue was purified using preparative TLC on silica gel (dichloromethane/methanol=10/1) to provide Int-3c. $^1$H NMR (400 MHz, methanol-d4) δ 8.47 (s, 1H), 7.50-7.51 (m, 2H), 7.30-7.32 (m, 3H), 5.19 (s, 2H), 3.96-3.98 (m, 2H), 3.65-3.68 (m, 4H), 2.34-2.36 (m, 2H), 1.89-1.93 (m, 2H).

Step D—Synthesis of Intermediate Compound Int-3d

A solution of Int-3c (90 mg, 0.20 mmol) in N,N-dimethylformamide (4 mL) was treated with cesium carbonate (62.2 mg, 0.19 mmol) and 1-bromo-2-methoxyethane (19.9 mg, 0.14 mmol). The mixture was allowed to stir at 20° C. for 5 hours and concentrated in vacuo. The resulting residue was purified using preparative TLC on silica gel (dichloromethane/methanol=10/1) to provide Int-3d. $^1$H NMR (400 MHz, methanol-d4) δ 8.49 (s, 1H), 7.47-7.49 (m, 2H), 7.31-7.32 (m, 3H), 5.18 (s, 2H), 3.94-3.97 (m, 2H), 3.88 (s, 2H), 3.62-3.72 (m, 6H), 3.34 (s, 3H), 2.30-2.36 (m, 2H), 1.86-1.89 (m, 2H).

Step E—Synthesis of Intermediate Compound Int-3e

A solution of Int-3d (5 mg, 10 μmol), N,N-diisopropylethylamine (0.018 mL, 0.105 mmol), (2,4-difluorophenyl)methanamine (7.5 mg, 0.05 mmol), Pd(Ph$_3$P)$_4$ (6.0 mg, 5 μmol) in methanol (0.5 mL) and dimethylsulfoxide (1.5 mL) was allowed to stir at 80° C. under carbon monoxide (1 atm) for 16 hours. The mixture was cooled to room temperature, diluted with water (3 mL) and extracted with ethyl acetate (10 mL×3). The combined organic layers were washed with 1N aq HCl (3 mL), dried over anhydrous sodium sulfate, filtered and concentrated in vacuo. The resulting residue was purified using preparative TLC on silica gel (dichloromethane/methanol=20/1) to provide Int-3e. $^1$H NMR (400 MHz, methanol-d4) δ 8.77 (s, 1H), 7.30-7.49 (m, 6H), 6.89-7.00 (m, 2H), 5.17 (s, 2H), 4.63-4.65 (d, J=5.2 Hz, 2H), 3.87-3.93 (m, 2H), 3.75 (s, 3H), 3.61-3.70 (m, 6H), 3.34 (s, 3H), 2.25-2.32 (m, 2H), 1.91-2.00 (m, 2H). MS (+ESI) m/z: 568.2.

Step F—Synthesis of Compound 6

A solution of Int-3e (15 mg, 0.026 mmol) in N,N-dimethylformamide (3 mL) was treated with lithium chloride (11.2 mg, 0.26 mmol), stirred at 100° C. for 2 hours, filtered and the filtrate was directly purified using RP-HPLC to provide Compound 6. $^1$H NMR (400 MHz, methanol-d4) δ 8.63 (s, 1H), 7.33-7.35 (m, 1H), 6.82-6.89 (m, 2H), 4.54 (s, 2H), 3.96 (s, 2H), 3.82-3.88 (m, 2H), 3.57-3.72 (m, 6H), 3.25 (s, 3H), 2.16-2.21 (m, 2H), 1.87-2.94 (m, 2H). MS (+ESI) m/z: 478.2.

The following compound of the present invention was made using the methods described above in Example 3 and substituting the appropriate reactants and reagents:

| Compound Number | Structure | Exact Mass [M + H]$^+$ |
|---|---|---|
| 7 | 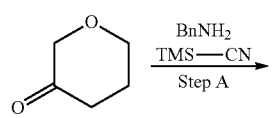 | Calc'd 434.2, found 434.0 |

Example 4

Preparation of Compounds 8 and 9

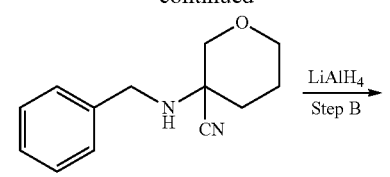
Int-4a

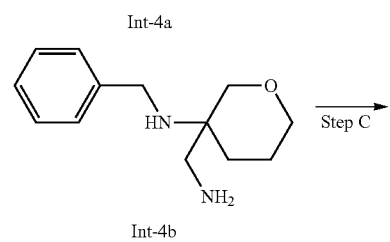
Int-4b

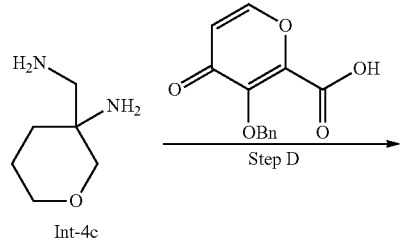
Int-4c

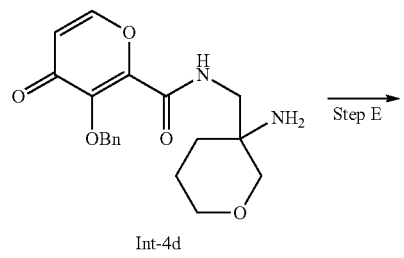
Int-4d

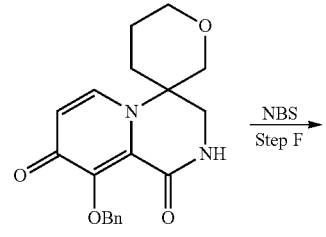
Int-4e

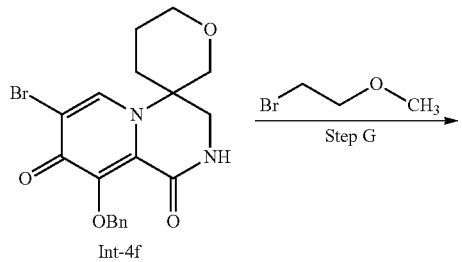
Int-4f

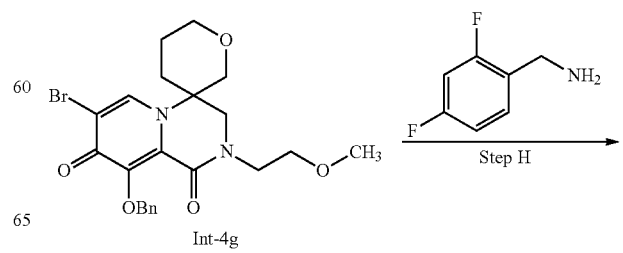
Int-4g

-continued

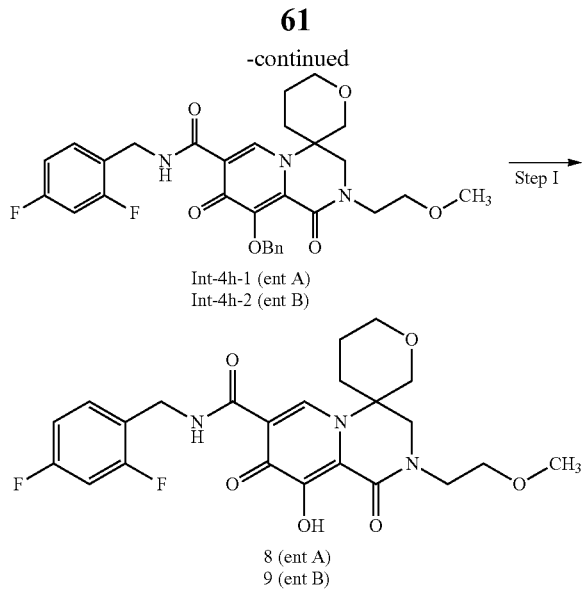

Int-4h-1 (ent A)
Int-4h-2 (ent B)

8 (ent A)
9 (ent B)

Step A—Synthesis of Intermediate Compound Int-4a

A mixture of dihydro-2H-pyran-3(4H)-one (256 mg, 3.19 mmol) and phenylmethanamine (302 mg, 2.81 mmol) was allowed to stir at 20° C. for 5 minutes, cooled 0° C. and treated dropwise with trimethylsilanecarbonitrile (305 mg, 3.07 mmol). After addition, the mixture was allowed to stir at 20° C. for 15 hours. The reaction mixture was directly purified using column chromatography on silica gel (petroleum ether:ethyl acetate=5:1) to provide Int-4a $^1$H NMR (400 MHz, CDCl$_3$) δ 7.27-7.43 (m, 5H), 4.03 (dd, J=1.6, 11.2 Hz, 1H), 3.92-4.00 (m, 2H), 3.83-3.91 (m, 1H), 3.45 (dt, J=2.2, 11.0 Hz, 1H), 3.36 (d, J=11.3 Hz, 1H), 2.21 (d, J=12.1 Hz, 1H), 1.89-2.02 (m, 1H), 1.72-1.83 (m, 2H).

Step B—Synthesis of Intermediate Compound Int-4b

A mixture of Int-4a (500 mg, 2.29 mmol) in THF (10 mL) at 0° C. was treated with lithium aluminum hydride (130 mg, 3.44 mmol). After addition, the mixture was allowed to stir at 0° C. for 2 hours, quenched by water (2 mL), filtered and the filtrate was concentrated in vacuo to provide Int-4b that was used without further purification. $^1$H NMR (400 MHz, CDCl$_3$) δ 7.30-7.40 (m, 5H), 3.72-3.84 (m, 2H), 3.64 (d, J=3.7 Hz, 2H), 3.46-3.55 (m, 1H), 3.38 (d, J=11.2 Hz, 1H), 2.69-2.77 (m, 1H), 2.53-2.64 (m, 1H), 1.78-1.87 (m, 1H), 1.66-1.74 (m, 2H), 1.42-1.51 (m, 1H).

Step C—Synthesis of Intermediate Compound Int-4c

A mixture of Int-4b (434 mg, 1.97 mmol), trifluoroacetic acid (0.15 mL, 1.97 mmol) and Pd(OH)$_2$ (138 mg, 0.197 mmol) in methanol (8 mL) was allowed to stir at 50° C. under H$_2$ (15 psi) for 36 hours and then filtered and the filtrate was concentrated in vacuo to provide Int-4c that was used without further purification. $^1$H NMR (400 MHz, CDCl$_3$) δ 3.63-3.89 (m, 2H), 3.55 (d, J=7.6 Hz, 1H), 3.31-3.46 (m, 2H), 2.75-2.92 (m, 1H), 1.49-1.80 (m, 4H).

Step D—Synthesis of Intermediate Compound Int-4d

A solution of Int-4c (248 mg, 1.91 mmol), N,N-diisopropylethylamine (0.50 ml, 2.87 mmol) and 3-(benzyloxy)-4-oxo-4H-pyran-2-carboxylic acid (235 mg, 0.954 mmol) in N,N-dimethylformamide (10 mL) was treated with ((6-chloro-1H-benzo[d][1,2,3]triazol-1-yl)oxy)tri(pyrrolidin-1-yl)phosphoniumhexafluoro-phosphate (V) (635 mg, 1.15 mmol) at 20° C., stirred at 20° C. for 4 hours and concentrated in vacuo. The resulting residue was purified using column chromatography on silica gel (dichloromethane: ethyl acetate=1:2 then dichloromethane:methanol:Et$_3$N=20: 1:0.4) to provide a crude Int-4d. $^1$H NMR (400 MHz, CDCl$_3$) δ 7.76-7.86 (m, 1H), 7.50 (d, J=7.2 Hz, 1H), 7.29-7.42 (m, 5H), 6.49 (d, J=7.6 Hz, 1H), 5.34-5.51 (m, 2H), 4.88-4.99 (m, 1H), 4.57-4.65 (m, 1H), 4.29-4.37 (m, 1H), 3.74 (d, J=12.0 Hz, 1H), 3.49 (d, J=6.4 Hz, 2H), 2.01-2.07 (m, 2H), 1.84-1.92 (m, 2H). MS (ESI) m/z: 359.2.

Step E—Synthesis of Intermediate Compound Int-4e

A mixture of Int-4d (235 mg, 0.656 mmol) and NaHCO$_3$ (55 mg, 0.656 mmol) in water (10 mL) was allowed to stir at 100° C. for 1 hour and then concentrated in vacuo. The resulting residue was purified using column chromatography on alumina (dichloromethane: methanol =50: 1) to provide crude Int-4e. $^1$H NMR (400 MHz, CDCl$_3$) δ 8.58 (s, 1H), 7.61 (d, J=7.2 Hz, 2H), 7.29-7.36 (m, 3H), 6.68 (br s, 1H), 5.39 (d, J=10.0 Hz, 1H), 5.21 (d, J=10.0 Hz, 1H), 3.95-4.05 (m, 2H), 3.71 (d, J=12.8 Hz, 1H), 3.43-3.51 (m, 2H), 3.15 (dd, J=5.6, 13.2 Hz, 1H), 2.30 (d, J=13.2 Hz, 1H), 1.79-1.83 (m, 3H). MS (ESI) m/z: 341.1.

Step F—Synthesis of Intermediate Compound Int-4f

A mixture of Int-4e (94 mg, 0.275 mmol) and N-bromosuccinimide (147 mg, 0.826 mmol) in dichloromethane (4 mL) was allowed to stir at 25° C. for 3 hours and then concentrated in vacuo. The resulting residue was purified using RP-HPLC to provide Int-4f. $^1$H NMR (400 MHz, CDCl$_3$) δ 8.56 (s, 1H), 7.61 (d, J=7.0 Hz, 2H), 7.28-7.38 (m, 3H), 6.46 (br s, 1H), 5.40 (d, J=9.9 Hz, 1H), 5.21 (d, J=9.9 Hz, 1H), 4.01 (d, J=12.3 Hz, 2H), 3.62-3.73 (m, 2H), 3.50 (d, J=13.5 Hz, 1H), 3.07-3.15 (m, 1H), 2.31 (d, J=12.3 Hz, 1H), 1.75-1.86 (m, 3H). MS (ESI) m/z: 419.1, 421.1.

Step G—Synthesis of Intermediate Compound Int-4g

A mixture of Int-4f (50 mg, 0.120 mmol), 1-bromo-2-methoxyethane (84 mg, 0.596 mmol) and cesium carbonate (165 mg, 0.358 mmol) in N,N-dimethylformamide (3 mL) was allowed to stir at 25° C. for 16 hours, filtered and the filtrate was concentrated to provide Int-4g. $^1$H NMR (400 MHz, CDCl$_3$) δ 8.58 (s, 1H), 7.66 (d, J=7.0 Hz, 2H), 7.28-7.37 (m, 3H), 5.41 (d, J=9.8 Hz, 1H), 5.18 (d, J=9.8 Hz, 1H), 4.02 (d, J=13.8 Hz, 2H), 3.54-3.76 (m, 7H), 3.34 (s, 4H), 2.25 (d, J=13.8 Hz, 1H), 1.84-1.91 (m, 1H), 1.72-1.79 (m, 2H). MS (ESI) m/z: 477.0, 479.0.

Step H—Synthesis of Intermediate Compound Int-4h-1 and Int-4h-2

A solution of Int-4g (50 mg, 0.105 mmol) in dimethylsulfoxide (5 mL) was treated with (2,4-difluorophenyl) methanamine (30.0 mg, 0.21 mmol), N,N-diisopropylethylamine (40.6 mg, 0.31 mmol) and Pd(Ph$_3$P)$_4$ (60.5 mg, 0.05 mmol). The reaction was stirred under carbon monoxide (1 atm) at 96° C. for 4 hours, cooled to room temperature, filtered and the filtrate was concentrated, The resulting residue was purified using RP-HPLC to provide the intended product as the racemate. $^1$H NMR (400 MHz, CDCl$_3$) δ 10.68 (t, J=5.2 Hz, 1H), 9.09 (s, 1H), 7.57 (d, J=7.0 Hz, 2H), 7.28-7.42 (m, 4H), 6.82 (d, J=8.8 Hz, 2H), 5.20-5.33 (m, 2H), 4.65 (d, J=5.8 Hz, 2H), 3.90-3.95 (m, 1H), 3.85 (br s, 1H), 3.79 (d, J=12.3 Hz, 2H), 3.74 (d, J=6.4 Hz, 1H), 3.63-3.71 (m, 3H), 3.55-3.60 (m, 1H), 3.49 (d, J=13.8 Hz, 1H), 3.35 (s, 3H), 2.28-2.36 (m, 1H), 1.88-1.98 (m, 1H), 1.79 (br s, 2H). MS (ESI) m/z: 568.1. Separation by chiral SFC (Chiralcel OJ-H 250×4.6 mm I.D., 5um; gradient elution with 5% to 40% methanol (0.05% diethylamine) in SC—CO$_2$; 2.35 mL/min; 220 nm) provided the earlier eluting Int-4h-1 and the later eluting Int-4h-2.

Step I—Synthesis of Compound 8 and Compound 9

A mixture of Int-4h-1 (15 mg, 0.035 mmol) and lithium chloride (29.9 mg, 0.705 mmol) in N,N-dimethylformamide (1 mL) was allowed to stir at 80° C. for 3 hours, cooled to room temperature and directly purified using RP-HPLC to provide Compound 8. ¹H NMR (400 MHz, CDCl₃) δ 10.52 (br s, 1H), 8.92 (s, 1H), 7.31-7.42 (m, 1H), 6.74-6.88 (m, 2H), 4.65 (br s, 2H), 3.79-3.95 (m, 5H), 3.58-3.79 (m, 5H), 3.36 (s, 3H), 2.35 (ddd, J=4.6, 8.2, 13.0 Hz, 2H), 1.98 (dd, J=6.6, 12.7 Hz, 2H). MS (ESI) m/z: 478.1.

A similar procedure was used to convert Int-4h-2 to Compound 9. ¹H NMR (400 MHz, CDCl₃) δ 10.48 (br s, 1H), 8.90 (s, 1H), 7.32-7.43 (m, 1H), 6.72-6.88 (m, 2H), 4.64 (br s, 2H), 3.79-3.94 (m, 5H), 3.60-3.77 (m, 5H), 3.36 (s, 3H), 2.34 (ddd, J=4.6, 8.2, 13.2 Hz, 2H), 1.98 (dd, J=6.4 Hz, 2H). MS (ESI) m/z: 478.1.

The following compounds of the present invention were made using the methods described above in Example 4 and substituting the appropriate reactants and reagents:

Chiral resolution was accomplished after Step H in Example 4 with SFC (ChiralPak OJ, 5 μm, 250×30 mm I.D. 80:20 SC—CO₂/ethanol(with 0.1% NH₃H₂O), 60 mL/min, 220 nm). Enantiomer A refers to the earlier eluting enantiomer and enantiomer B refers to the later eluting enantiomer.

| Compound Number | Structure | Exact Mass [M + H]⁺ |
|---|---|---|
| 10 | enantiomer A | Calc'd 434.2, found 434.2 |
| 11 | enantiomer B | Calc'd 434.2, found 434.2 |

Example 5

Preparation of Compounds 12 and 13

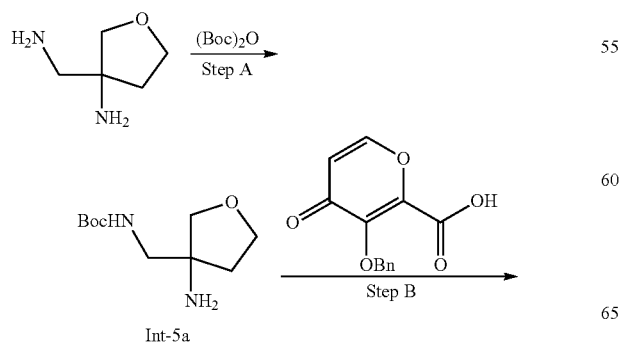

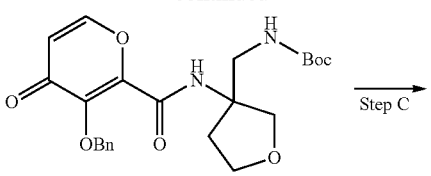
Int-5b

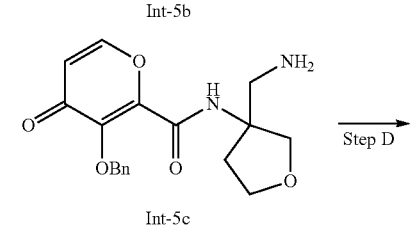
Int-5c

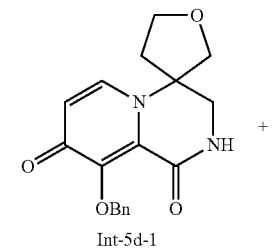
Int-5d-1

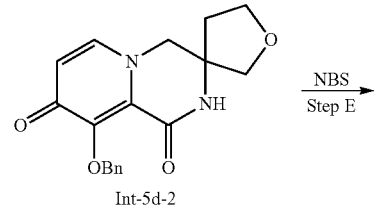
Int-5d-2

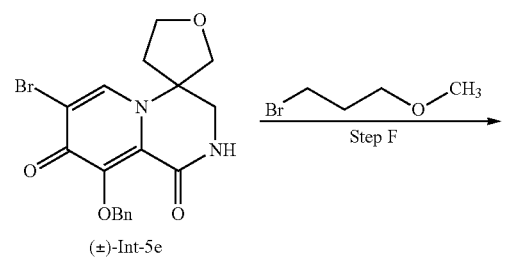
(±)-Int-5e

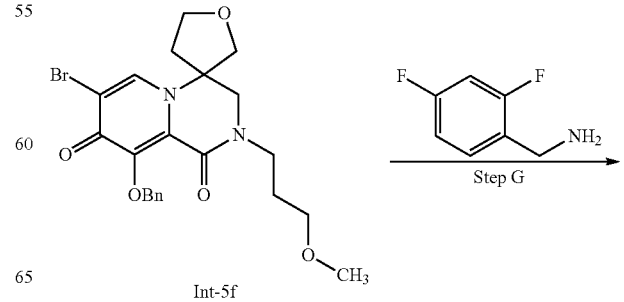
Int-5f

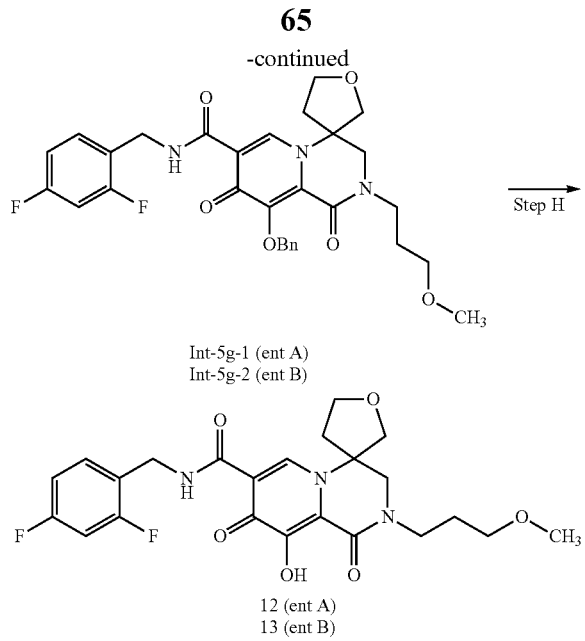

Int-5g-1 (ent A)
Int-5g-2 (ent B)

12 (ent A)
13 (ent B)

Step A—Synthesis of Intermediate Compound Int-5a

A solution of 3-(aminomethyl)tetrahydrofuran-3-amine (587.5 mg, 5.1 mmol) in methanol (10 mL) at 0° C. was treated with triethylamine (2.12 mL, 15.2 mmol) Boc$_2$O (1.41 mL, 6.07 mmol). The mixture was allowed to stir at 15° C. for 5 hours, treated with water (5 mL) and extracted with dichloromethane (10 mL×3). The combined organic layers were washed with brine (5 mL), dried over anhydrous sodium sulfate and concentrated in vacuo to provide Int-5a, which was used without further purification. $^1$H NMR (400 MHz, CDCl$_3$) δ 3.99-4.03 (m, 1H), 3.90-3.92 (m, 1H), 3.48-3.63 (m, 2H), 3.22-3.26 (m, 2H), 1.95-1.98 (m, 1H), 1.70-1.75 (m, 1H), 1.39 (s, 9H).

Step B—Synthesis of Intermediate Compound Int-5b

A solution of Int-5a (722 mg, 3.34 mmol) in N,N-dimethylformamide (10 mL) was treated with N,N-diisopropylethylamine (1.29 g, 10.0 mmol) and HATU (1.904 g, 5.01 mmol), stirred for several minutes and then treated with 3-(benzyloxy)-4-oxo-4H-pyran-2-carboxylic acid (657.55 mg, 2.67 mmol). The mixture was allowed to stir at 15° C. for 3 hours, diluted with water (5 mL), extracted with ethyl acetate (12 mL×5). The combined organic layers were washed with brine (8 mL), dried over anhydrous sodium sulfate, filtered, concentrated in vacuo and purified using chromatography on silica gel (petroleum ether:ethyl acetate=5:1 to 1:1) to provide Int-5b. $^1$H NMR (400 MHz, CDCl$_3$) δ 8.00 (s, 1H), 7.81 (d, J=5.6 Hz, 1H), 7.41 (d, J=10.0 Hz, 5H), 6.48 (d, J=5.2 Hz, 1H), 5.41-5.50 (m, 2H), 3.69-3.81 (m, 3H), 3.55-3.58 (m, 1H), 3.50 (d, J=4.2 Hz, 2H), 1.91 (s, 1H), 1.66 (s, 1H), 1.42 (s, 9H). MS (+ESI) m/z: 445.0 [M+H]$^+$, 389.0 [M-tBu]$^+$ Step C—Synthesis of Intermediate Compound Int-5c A solution of Int-5b (1.19 g, 2.67 mmol) in dichloromethane (20 mL) at 0° C. was treated with trifluoroacetic acid (4 mL). The mixture was allowed to stir at 15° C. for 2 hours and then concentrated in vacuo to provide Int-5c that was used in the next step without further purification. $^1$H NMR (400 MHz, CDCl$_3$) δ 8.51 (s, 1H), 7.96 (d, J=5.6 Hz, 1H), 7.71 (s, 2H), 7.44 (s, 5H), 6.81 (d, J=5.6 Hz, 1H), 5.44-5.55 (m, 2H), 3.88-3.93 (m, 3H), 3.70-3.79 (m, 3H), 3.34 (s, 2H), 1.98-2.05 (m, 1H), 1.64-1.70 (m, 1H).

Step D—Synthesis of Intermediate Compound Int-5d-1 and Intermediate Compound Int-5d-2

A solution of Int-5c (637.7 mg, 1.848 mmol) in ethanol (15 mL) was heated to reflux for 48 hours, cooled to room temperature and concentrated in vacuo. The resulting residue was purified using preparative TLC on silica gel (dichloromethane:methanol=10:1) to provide Int-5d-1 $^1$H NMR (400 MHz, CDCl$_3$) δ 7.53-7.60 (m, 2H), 7.34 (s, 1H), 7.25-7.31 (m, 3H), 6.52 (d, J=7.2 Hz, 1H), 5.35-5.41 (m, 2H), 4.11-4.18 (m, 2H), 3.95-3.97 (m, 1H), 3.62-3.64 (m, 1H), 3.48-3.51 (m, 1H), 3.22-3.26 (m, 1H), 2.27 (t, J=7.2 Hz, 2H) and Int-5d-2 $^1$H NMR (400 MHz, CDCl$_3$) δ 7.49-7.53 (m, 2H), 7.27-7.29 (m, 3H), 7.19 (d, J=7.2 Hz, 1H), 6.50 (d, J=7.2 Hz, 1H), 5.33-5.43 (m, 2H), 3.93 (s, 4H), 3.43-3.61 (m, 2H), 1.94 (t, J=8.0 Hz, 2H).

Step E—Synthesis of Intermediate Compound (±)-Int-5e

A solution of Int-5d-1 (88.65 mg, 0.271 mmol) in dichloromethane (6 mL) at 0° C. was treated with N-bromosuccinimide (120.8 mg, 0.678 mmol). The mixture was allowed to stir at 18° C. for 10 hours, quenched with aqueous sodium sulfite (3 mL), diluted with water (3 mL) and extracted with dichloromethane (5 mL×4). The combined organic layers were washed with brine (5 mL), dried over anhydrous sodium sulfate, filtered and concentrated in vacuo. The crude residue was purified using flash chromatography on silica gel (dichloromethane: methanol=15:1 to 10:1) to provide (±)-Int-5e. $^1$H NMR (400 MHz, methanol-d4) δ 8.24 (s, 1H), 7.52 (d, J=6.0 Hz, 2H), 7.31 (d, J=7.6 Hz, 3H), 5.14-5.25 (m, 2H), 4.32 (d, J=10.8 Hz, 1H), 4.16-4.19 (m, 1H), 3.99-4.01 (m, 1H), 3.78 (d, J=11.2 Hz, 1H), 3.60 (d, J=13.6 Hz, 1H), 3.47 (d, J=14.4 Hz, 1H), 2.38-2.64 (m, 2H). Chiral resolution to provide the separated enantiomers was accomplished with SFC (Chiralpak AD, 50% methanol in SC—CO$_2$; 220 nm) to provide the separated enantiomers Int-5e-1 (enantiomer A) and Int-5e-2 (enantiomer B).

Step F—Synthesis of Intermediate Compound Int-5f

A solution of (±)-Int-5e (62.9 mg, 0.155 mmol) in N,N-dimethylformamide (6 mL) was treated with cesium carbonate (151.9 mg, 0.466 mmol) and 1-bromo-3-methoxypropane (47.54 mg, 0.311 mmol). The mixture was allowed to stir at 50° C. for 4 hours, quenched with water (3 mL) and extracted with ethyl acetate (10 mL×3). The combined organic layers were washed with brine (10 mL×2), dried over anhydrous sodium sulfate, filtered and concentrated in vacuo. The resulting residue was purified using preparative TLC on silica gel (methanol:dichloromethane=1:20) to provide Int-5f. $^1$H NMR (400 MHz, methanol-d4) δ 8.18 (s, 1H), 7.49-7.50 (d, J=6 Hz, 2H), 7.26-7.31 (m, 3H), 5.11-5.21 (m, 2H), 4.24-4.27 (d, J=11.2 Hz, 1H), 4.10-4.16 (m, 1H), 3.95-4.01 (m, 1H), 3.74-3.78 (m, 2H), 3.59-3.63 (m, 2H), 3.45-3.53 (m, 1H), 3.42-3.44 (m, 2H), 3.28 (s, 3H), 2.32-2.40 (m, 2H), 1.83-1.86 (m, 2H). MS (ESI) m/z: 477.1, 479.1.

Step G—Synthesis of Intermediate Compound Int-5g-1 and Int-5g-2

A solution of Int-5f (60 mg, 0.126 mmol) in dimethylsulfoxide (1.5 mL) and methanol (4 mL) was treated with N,N-diisopropylethylamine (0.11 mL, 0.628 mmol), (2,4-difluorophenyl)methanamine (180 mg, 1.26 mmol) and Pd(Ph$_3$P)$_4$ (29.11 mg, 0.025 mmol). The mixture was allowed to stir at 90° C. for 16 hours under carbon monoxide (1 atm). The mixture was cooled to room temperature extracted by ethyl acetate (6 mL×3), washed with HCl (3 mL, 1M) and brine (5 mL), dried over anhydrous sodium sulfate, filtered, concentrated under reduced pressure. The crude product was purified using preparative TLC on silica gel (methanol: dichloromethane=1:20) to provide the crude racemate. MS (ESI) m/z: 568.1. Chiral resolution to provide the separated enantiomers was accomplished with SFC (Chiralpak AD-H 250×4.6 mm I.D., 5 um; 4% ethanol (0.05% diethylamine) in SC—CO$_2$; 2.35 mL/min; 220 nm) to provide earlier eluting Int-5g-1 $^1$H NMR (400 MHz, CDCl$_3$) δ 10.46-10.48 (m, 1H), 8.65 (s, 1H), 7.60-7.62 (d, J=7.2 Hz, 2H), 7.30-7.37 (m, 4H), 6.79-6.85 (m, 2H), 5.29-5.32 (m, 2H), 4.63-4.64 (d, J=5.6 Hz, 2H), 4.23-4.30 (m, 1H), 4.12-4.14 (d, J=10.8 Hz, 1H), 4.03-4.09 (m, 1H), 3.80-3.83 (d, J=10.8 Hz, 1H), 3.51-3.67 (m, 4H), 3.44-3.46 (m, 2H), 3.33 (s, 3H), 2.43-2.45 (m, 1H), 2.29-2.31 (m, 1H), 1.88-1.91 (m, 2H); and later eluting Int-5g-2 $^1$H NMR (400 MHz, CDCl$_3$) δ 10.46-10.48 (m, 1H), 8.65 (s, 1H), 7.60-7.62 (d, J=7.2 Hz, 2H), 7.30-7.37 (m, 4H), 6.79-6.85 (m, 2H), 5.29-5.32 (m, 2H), 4.63-4.64 (d, J=5.6 Hz, 2H), 4.23-4.30 (m, 1H), 4.12-4.14 (d, J=10.8 Hz, 1H), 4.03-4.09 (m, 1H), 3.80-3.83 (d, J=10.8 Hz, 1H), 3.51-3.67 (m, 4H), 3.44-3.46 (m, 2H), 3.33 (s, 3H), 2.43-2.45 (m, 1H), 2.29-2.31 (m, 1H), 1.88-1.91 (m, 2H).

Step H—Synthesis of Compound 12 and 13

A solution of Int-5g-1 (10 mg, 0.018 mmol) in N,N-dimethylformamide (1.5 mL) was treated with lithium chloride (0.747 mg, 0.018 mmol). The resulting solution was heated to 85° C. for 1.5 hours, cooled to room temperature and directly purified using RP-HPLC to provide Compound 12. $^1$H NMR (400 MHz, CDCl$_3$) δ 12.83 (s, 1H), 10.40 (s, 1H), 8.52 (s, 1H), 7.32-7.38 (m, 1H), 6.75-6.82 (m, 2H), 4.60-4.62 (d, J=5.2 Hz, 2H), 4.02-4.18 (m, 3H), 3.80-3.82 (d, J=10.4 Hz, 1H), 3.67-3.70 (d, J=10.8 Hz, 4H), 3.45-3.46 (d, J=5.2 Hz, 2H), 3.29 (s, 3H), 2.43-2.45 (m, 1H), 2.25-2.27 (m, 1H), 1.89-1.92 (m, 2H). MS (ESI) m/z: 478.2. A similar procedure was used to convert Int-5g-2 to Compound 13. $^1$H NMR (400 MHz, CDCl$_3$) δ 12.86 (br s, 1H), 10.39 (br s, 1H), 8.53 (s, 1H), 7.33-7.45 (m, 1H), 6.81 (q, J=9.5 Hz, 2H), 4.63 (d, J=4.7 Hz, 2H), 4.10-4.25 (m, 2H), 4.00-4.09 (m, 1H), 3.83 (d, J=10.6 Hz, 1H), 3.74 (s, 2H), 3.69 (t, J=6.7 Hz, 2H), 3.40-3.51 (m, 2H), 3.31 (s, 3H), 2.46 (td, J=6.7, 13.3 Hz, 1H), 2.20-2.36 (m, 1H), 1.86-2.00 (m, 2H). MS (ESI) m/z: 478.1

The following compounds of the present invention were made using the methods described above in Example 5 and substituting the appropriate reactants and reagents:

Chiral resolution was accomplished after Step G in Example 5 with SFC according to the conditions shown as footnotes to the following table.

| Compound Number | Structure | Exact Mass [M + H]$^+$ |
|---|---|---|
| 14$^a$ | 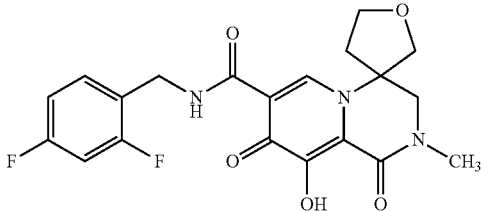<br>enantiomer A | Calc'd 420.1, found 420.2 |
| 15$^a$ | 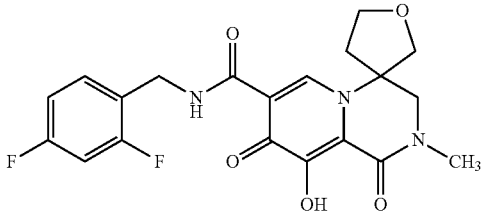<br>enantiomer B | Calc'd 420.1, found 420.2 |
| 16$^b$ | 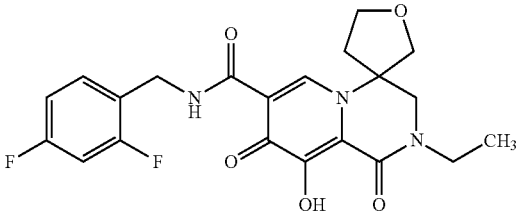<br>enantiomer A | Calc'd 434.2, found 434.2 |

-continued

| Compound Number | Structure | Exact Mass [M + H]⁺ |
|---|---|---|
| 17[b] | enantiomer B | Calc'd 434.2, found 434.2 |
| 18[c] | enantiomer A | Calc'd 450.1, found 450.3 |
| 19[c] | enantiomer B | Calc'd 450.1, found 450.3 |
| 20[d] | enantiomer A | Calc'd 464.2, found 464.1 |
| 21[d] | enantiomer B | Calc'd 464.2, found 464.1 |
| 22[e] | enantiomer A | Calc'd 478.2, found 478.2 |

-continued

| Compound Number | Structure | Exact Mass [M + H]⁺ |
|---|---|---|
| 23ᵉ | (2,4-difluorobenzyl carboxamide pyridopyrazine spiro-tetrahydrofuran, N-ethoxyethyl; enantiomer B) | Calc'd 478.2, found 478.2 |
| 24 | (2,4-difluorobenzyl carboxamide pyridopyrazine spiro-tetrahydrofuran, N-hydroxyethyl) | Calc'd 450.1, found 450.3 |
| 25ᶠ | (3-chloro-2,4-difluorobenzyl carboxamide pyridopyrazine spiro-tetrahydrofuran, N-methoxyethyl; enantiomer A) | Calc'd 498.1, found 498.3 |
| 26ᶠ | (3-chloro-2,4-difluorobenzyl carboxamide pyridopyrazine spiro-tetrahydrofuran, N-methoxyethyl; enantiomer B) | Calc'd 498.1, found 498.3 |
| 27ᶠ | (3-chloro-4-fluorobenzyl carboxamide pyridopyrazine spiro-tetrahydrofuran, N-methoxyethyl; enantiomer A) | Calc'd 480.1, found 480.3 |
| 28ᶠ | (3-chloro-4-fluorobenzyl carboxamide pyridopyrazine spiro-tetrahydrofuran, N-methoxyethyl; enantiomer B) | Calc'd 480.1, found 480.3 |

-continued

| Compound Number | Structure | Exact Mass [M + H]+ |
|---|---|---|
| 29[f] | enantiomer A | Calc'd 480.1, found 480.3 |
| 30[f] | enantiomer B | Calc'd 480.1, found 480.3 |
| 31 | 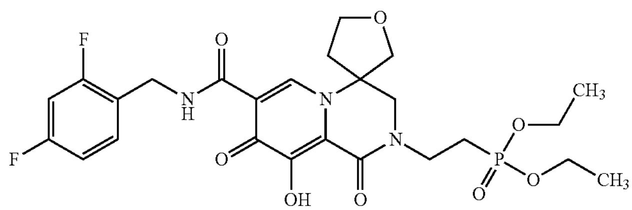 [SMILES: CCOP(=O)(CCN1CC2(CCOC2)n2cc(C(=O)NCc3ccc(F)cc3F)c(=O)c(O)c2C1=O)OCC] | Calc'd 570.2, found 570.5 |

[a]Chiralcel AD 250 × 30 mm, 10 um, 50% ethanol (0.1% NH₃H₂O) in SC—CO₂, 80 mL/min, 220 nm
[b]Chiralpak OJ 250 × 30 mm, 5 um 20% ethanol (0.1% NH₃H₂O) in SC—CO₂, 60 mL/min, 220 nm
[c]Chiralcel AD 250 × 30 mm, 10 um, 35% 2-propanol (0.1% diethylamine) in SC—CO₂, 80 mL/min, 220 nm
[d]Chiralpak AD 250 × 30 mm, 10 um, 30% 2-propanol (0.1% NH₃H₂O) in SC—CO₂, 80 mL/min, 220 nm
[e]Chiralpak AD 250 × 30 mm, 10 um, 50% ethanol (0.1% NH₃H₂O) in SC—CO₂, 80 mL/min, 220 nm
[f]Chiralpak AD-H 250 × 30 mm, 40% iPrOH (0.1% diethylamine) in SC—CO₂, 80 mL/min, 220 nm

Example 6

Preparation of Compound 32

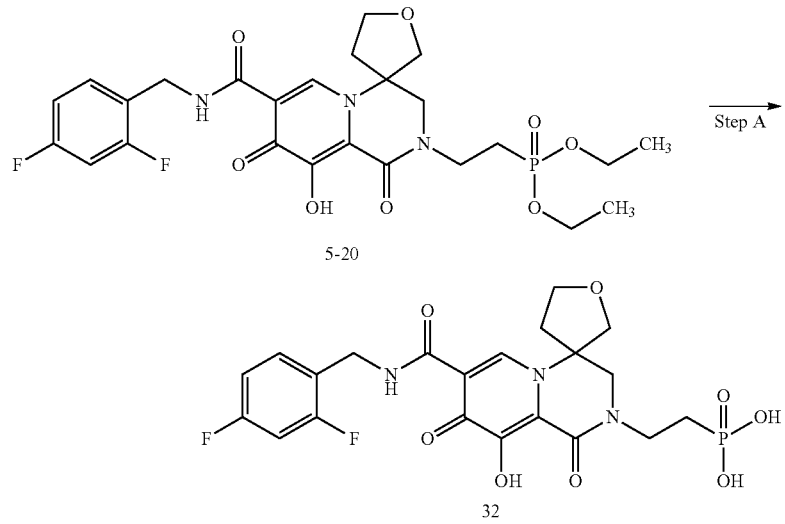

Step A—Synthesis of Compound 32

A solution of Compound 5-20 (15 mg, 0.023 mmol) in dichloromethane (1.0 mL) under an atmosphere of nitrogen gas was treated with bromotrimethylsilane (17.4 mg, 0.114 mmol). The mixture was allowed to stir for 2 hours at room temperature, treated with additional bromotrimethylsilane (17.4 mg, 0.114 mmol) and stirred for an additonal 16 hours.

The sample was loaded onto a plug of silica gel, and the plug was rinsed with 0.5% triethylamine in ethyl acetate followed by 1% HCl in ethyl acetate/ACN (1:1 v/v). The filtrate was concentrated in vacuo and purified using preparative RP-HPLC to provide Compound 32. MS (+ESI) m/z 514.4

Example 7

Preparation of Compounds 33 and 34

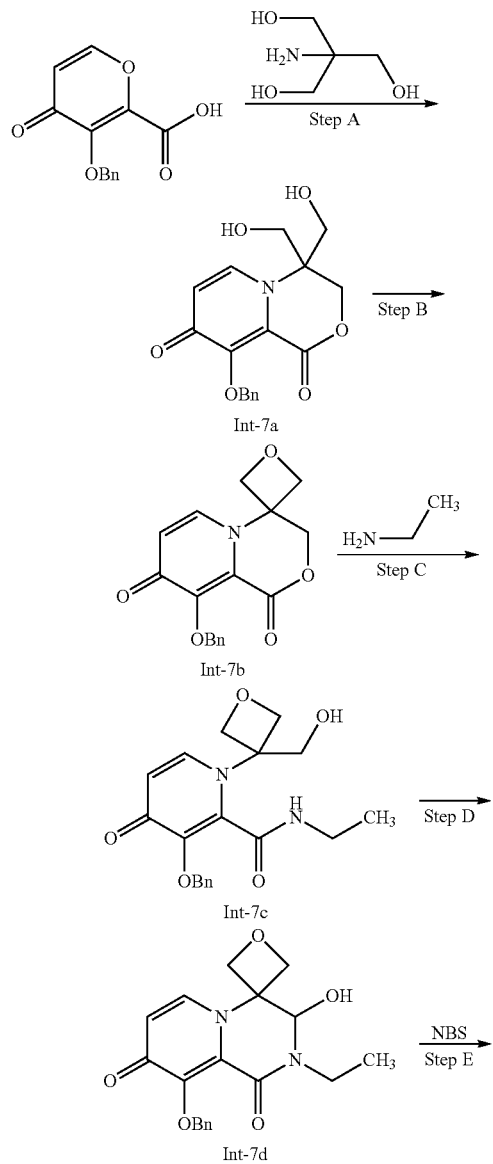

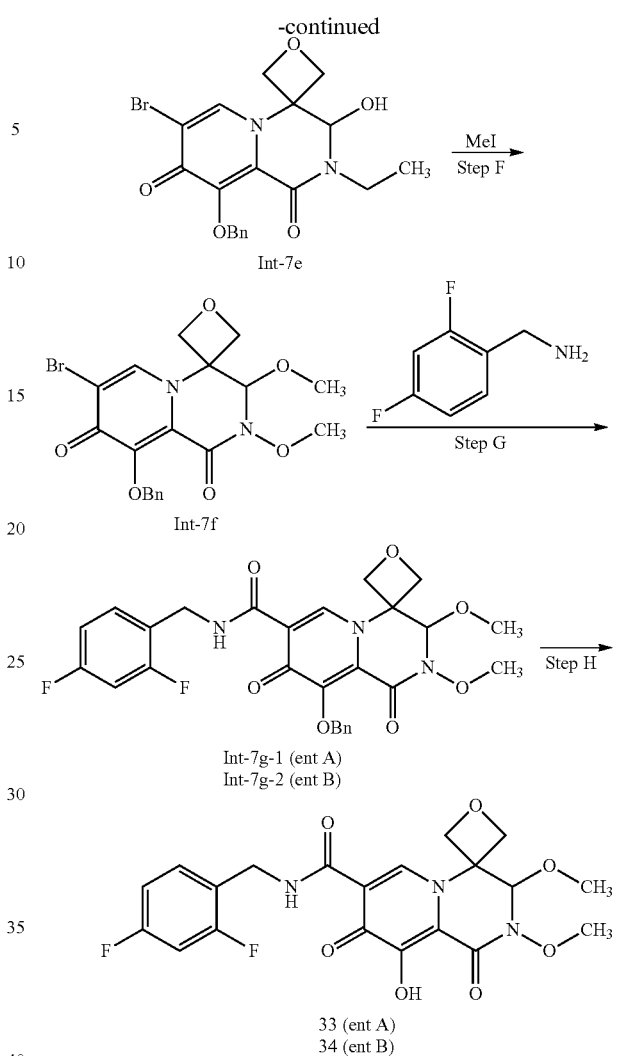

Step A—Synthesis of Intermediate Compound Int-7a

A solution of 3-(benzyloxy)-4-oxo-4H-pyran-2-carboxylic acid (1.50 g, 6.10 mmol) in ethanol (80 mL) was treated with 2-amino-2-(hydroxymethyl)propane-1,3-diol (5.90 g, 49 mmol) and the mixture was allowed to stir at 100° C. for 72 hours, cooled to room temperature, filtered and concentrated in vacuo. The resulting residue was purified using column chromatography on silica gel (dichloromethane: methanol=10:1) to provide Int-7a. $^1$H NMR (400 MHz, DMSO-$d_6$) δ 7.80 (d, J=8.0 Hz, 1H), 7.47 (d, J=7.2 Hz, 2H), 7.27-7.35 (m, 3H), 6.36 (d, J=8.0 Hz, 1H), 5.44 (t, J=4.8 Hz, 2H), 5.10 (s, 2H), 4.52 (s, 2H), 3.77-3.81 (m, 2H), 3.32-3.69 (m, 2H). MS (+ESI) m/z: 332.2

Step B—Synthesis of Intermediate Compound Int-7b

A mixture of Int-7a (620 mg, 1.87 mmol) and Ph$_3$P (981 mg, 3.74 mmol) in toluene (30 mL) was purged with nitrogen and treated with DIAD (0.725 mL, 3.7 mmol) via syringe. The resulting mixture was irradiated in a microwave reactor at 140° C. for 45 minutes, concentrated in vacuo and the crude residue was purified using column chromatography on silica gel (10:1 dichloromethane:methanol) to provide Int-7b. $^1$H NMR (400 MHz, CDCl$_3$) δ 7.82 (d, J=8.0 Hz, 1H), 7.53 (d, J=6.4 Hz, 2H), 7.31-7.35 (m, 3H), 6.58 (d, J=8.0 Hz, 1H), 5.36 (s, 2H), 4.91 (d, J=8.0 Hz, 2H), 4.70 (d, J=8.0 Hz, 2H), 4.63 (s, 2H).

Step C—Synthesis of Intermediate Compound Int-7c

A solution of Int-7b (100 mg, 0.319 mmol) in THF (2.5 mL) and methanol (0.5 mL) was treated with ethanamine (70% in water) (576 mg, 12.77 mmol) and heated at 65° C. in sealed tube for 1 hour, cooled to room temperature and concentrated in vacuo to provide the Int-7c. $^1$H NMR (400 MHz, DMSO-d$_6$) δ 8.70-8.80 (m, 1H), 7.26-7.35 (m, 5H), 7.13 (d, J=8.0 Hz, 1H), 6.24 (d, J=8.0 Hz, 1H), 5.48-5.52 (m, 1H), 5.02 (s, 2H), 4.84 (d, J=6.8 Hz, 2H), 4.28-4.32 (m, 2H), 4.04 (d, J=4.2 Hz, 2H), 3.05-3.15 (m, 2H), 0.96 (t, J=7.2 Hz, 3H). MS (+ESI) m/z: 359.1.

Step D—Synthesis of Intermediate Compound Int-7d

A stirred solution of Int-7c (100 mg, 0.279 mmol) in 1,2-dichloroethane (5 mL) was treated with Dess-Martin periodinane (237 mg, 0.56 mmol). The reaction mixture was allowed to stir at 18° C. for 16 hours, diluted with ethyl acetate (10 mL), filtered and concentrated in vacuo. The resulting residue was purified using preparative TLC on silica gel (dichloromethane:methanol=20:1) to provide Int-7d. $^1$H NMR (400 MHz, CDCl$_3$) δ 7.55 (d, J=6.8 Hz, 2H), 7.41 (d, J=8.0 Hz, 1H), 7.32-7.37 (m, 3H), 6.42 (d, J=8.0 Hz, 1H), 4.92 (d, J=9.2 Hz, 1H), 4.79 (d, J=8.8 Hz, 1H), 4.68 (d, J=8.8 Hz, 1H), 4.49-4.55 (m, 2H), 4.35 (d, J=8.0 Hz, 1H), 3.83-3.88 (m, 1H), 3.48-3.51 (m, 2H), 1.32 (t, J=6.8 Hz, 3H). MS (+ESI) m/z: 357.1.

Step E—Synthesis of Intermediate Compound Int-7e

A solution of Int-7d (80 mg, 0.224 mmol) in dichloromethane (5 mL) was treated with NBS (80 mg, 0.449 mmol) at 0° C., stirred for 6 hours at 18° C. and then quenched with aqueous Na$_2$SO$_3$ (5 mL) and extracted with dichloromethane (10 mL×3). The combined organic layers were dried over anhydrous sodium sulfate and concentrated in vacuo. The resulting residue was purified using preparative TLC on silica gel (dichloromethane:ethyl acetate=1:1) to provide Int-7e. $^1$H NMR (400 MHz, CDCl$_3$) δ 7.62 (s, 1H), 7.52 (d, J=6.8 Hz, 2H), 7.28-7.38 (m, 3H), 5.28 (m, 1H), 4.76-4.83 (m, 2H), 4.55 (d, J=9.2 Hz, 1H), 4.50 (d, J=8.0 Hz, 1H), 4.30 (d, J=8.0 Hz, 1H), 4.14-4.29 (m, 1H), 3.68-3.78 (m, 2H), 1.39 (t, J=7.2 Hz, 3H).

Step F—Synthesis of Intermediate Compound Int-7f

A solution of Int-7e (60 mg, 0.138 mmol) in N,N-dimethylformamide (6 mL) at 0° C. was treated with NaH (22.05 mg, 0.55 mmol) and iodomethane (0.086 mL, 1.38 mmol). The reaction mixture was allowed to stir for 10 minutes at 18° C., quenched with water (10 mL) and extracted with dichloromethane (10 mL×3). The combined organic layers were dried over anhydrous sodium sulfate and concentrated in vacuo. The resulting residue was purified using preparative TLC in silica gel (dichloromethane:methanol=20:1) to provide Int-7f. $^1$H NMR (400 MHz, CDCl$_3$) δ 8.16 (s, 1H), 7.64 (d, J=7.2 Hz, 2H), 7.28-7.35 (m, 3H), 5.51 (d, J=10.0 Hz, 1H), 5.21 (d, J=8.8 Hz, 1H), 5.08 (d, J=10.0 Hz, 1H), 5.03 (s, 1H), 4.78 (d, J=8.8 Hz, 1H), 4.58-4.64 (m, 2H), 4.17-4.22 (m, 1H), 3.34 (s, 3H), 3.19-3.26 (m, 1H), 1.31 (t, J=7.2 Hz, 3H). MS (+ESI) m/z: 449.1, 451.1.

Step G—Synthesis of Intermediate Compound Int-7g-1 and Int-7g-2

A mixture of Int-7f (40 mg, 0.089 mmol), N,N-diisopropylethylamine (0.047 mL, 0.267 mmol) and (2,4-difluorophenyl)methanamine (63.7 mg, 0.445 mmol) in dimethylsulfoxide (1 mL) and methanol (4 mL) was treated with Pd(Ph$_3$P)$_4$ (51.4 mg, 0.045 mmol) under nitrogen. The mixture was allowed to stir at 80° C. for 3 hours under carbon monoxide (1 atm) and then concentrated in vacuo. The resulting residue was dissolved in ethyl acetate (10 mL), filtered and the filtrate was washed with 1N HCl (10 mL), dried over anhydrous sodium sulfate and concentrated in vacuo. The resulting residue was purified using preparative TLC on silica gel (ethyl acetate: dichloromethane=1.5:1) to provide the product racemate. Chiral resolution to provide the enantiomers was accomplished with SFC (Chiral Pak OJ, 5 μm, 250×30 mm, 75:25 SC—CO$_2$:methanol (with 0.1% NH$_3$H$_2$O), 60 mL/min, 220 nm) to provide earlier eluting Int-7g-1 $^1$H NMR (400 MHz, CDCl$_3$) δ 10.39 (s, 1H), 8.88 (s, 1H), 7.59 (d, J=6.8 Hz, 2H), 7.28-7.38 (m, 4H), 6.79-6.83 (m, 2H), 5.41-5.45 (m, 2H), 5.11 (d, J=10.0 Hz, 1H), 5.05 (s, 1H), 4.69 (d, J=8.8 Hz, 1H), 4.56-4.63 (m, 4H), 4.15-4.19 (m, 1H), 3.34 (s, 3H), 3.21-3.27 (m, 1H), 1.31 (t, J=7.2 Hz, 3H). MS (M+H)$^+$540.2 and later eluting Int-7g-2 $^1$H NMR (400 MHz, CDCl$_3$) δ 10.35 (s, 1H), 8.84 (s, 1H), 7.54 (d, J=6.8 Hz, 2H), 7.23-7.33 (m, 4H), 6.72-6.77 (m, 2H), 5.41-5.45 (m, 2H), 5.11 (d, J=10.0 Hz, 1H), 5.05 (s, 1H), 4.69 (d, J=8.8 Hz, 1H), 4.56-4.63 (m, 4H), 4.15-4.19 (m, 1H), 3.34 (s, 3H), 3.21-3.27 (m, 1H), 1.31 (t, J=7.2 Hz, 3H). MS (+ESI) m/z: 540.2

Step H—Synthesis of Compound 33

A solution of Int-7g-1 (15 mg, 0.027 mmol) and lithium chloride (12 mg, 0.278 mmol) in N,N-dimethylformamide (2 mL) was allowed to stir at 100° C. for 1 hour. The mixture was directly purified using RP-HPLC to provide Compound 33. $^1$H NMR (400 MHz, CDCl$_3$) δ 10.42 (s, 1H), 8.87 (s, 1H), 7.34-7.40 (m, 1H), 6.78-6.85 (m, 2H), 5.53 (d, J=8.8 Hz, 1H), 5.22 (s, 1H), 4.75 (d, J=8.8 Hz, 1H), 4.65 (d, J=5.6 Hz, 2H), 4.51-4.56 (m, 2H), 4.32-4.34 (m, 1H), 3.52 (s, 3H), 3.26-3.31 (m, 1H), 1.36 (t, J=7.2 Hz, 3H). MS (M+H)$^-$: 450.1.

Step I—Synthesis of Compound 34

A solution of Int-7g-2 (15 mg, 0.027 mmol) and lithium chloride (12 mg, 0.278 mmol) in N,N-dimethylformamide (2 mL) was allowed to stir at 100° C. for 1 hour. The mixture was directly purified using RP-HPLC to provide Compound 34. $^1$H NMR (400 MHz, CDCl$_3$) δ 10.41 (s, 1H), 8.87 (s, 1H), 7.34-7.40 (m, 1H), 6.78-6.85 (m, 2H), 5.53 (d, J=8.8 Hz, 1H), 5.22 (s, 1H), 4.75 (d, J=8.8 Hz, 1H), 4.65 (d, J=5.6 Hz, 2H), 4.51-4.56 (m, 2H), 4.32-4.34 (m, 1H), 3.52 (s, 3H), 3.26-3.31 (m, 1H), 1.36 (t, J=7.2 Hz, 3H). MS (+ESI) m/z: 450.1.

Example 8

Preparation of Compounds 35-37

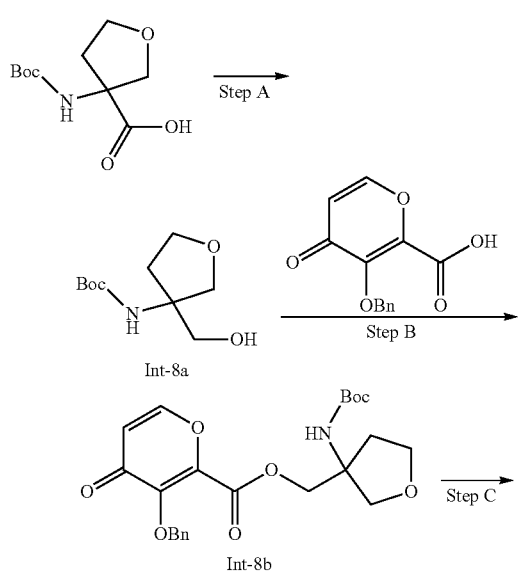

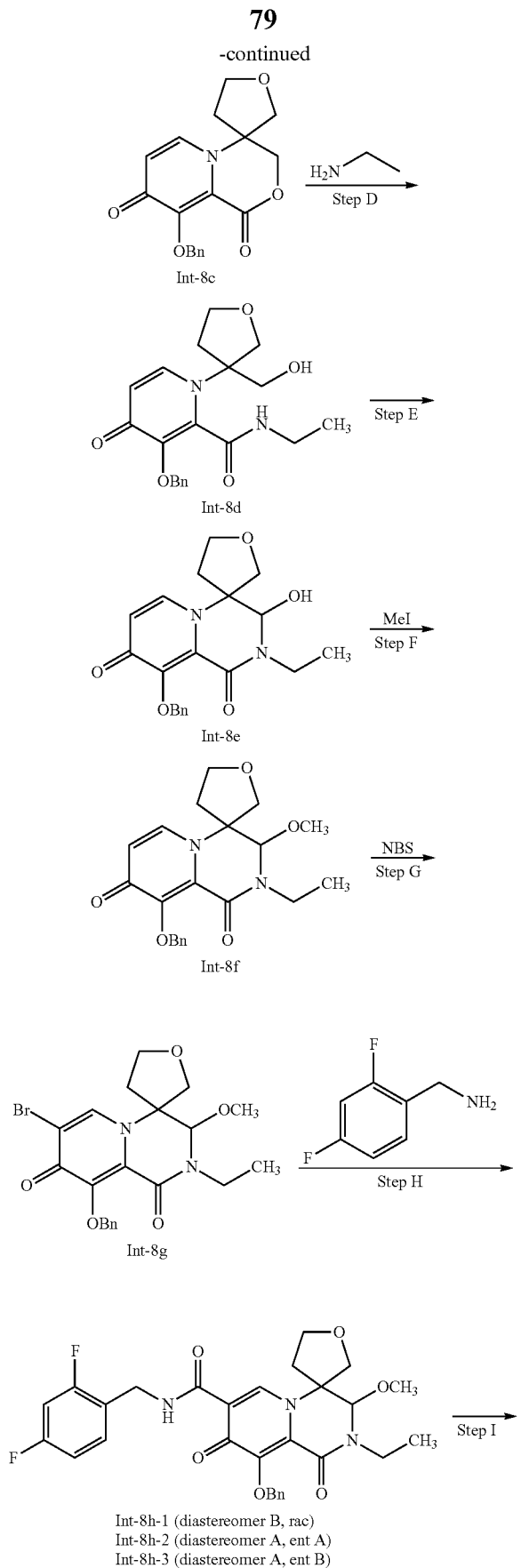

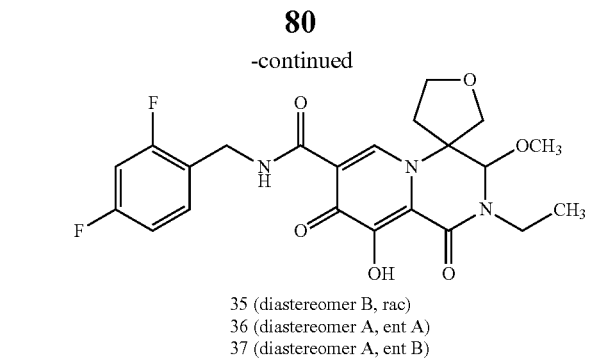

35 (diastereomer B, rac)
36 (diastereomer A, ent A)
37 (diastereomer A, ent B)

Step A—Synthesis of Intermediate Compound Int-8a

To a flame-dried flask under an atmosphere of nitrogen, 3-((tert-butoxycarbonyl)amino)tetrahydrofuran-3-carboxylic acid (5.0 g, 21.6 mmol) was dissolved in anhydrous THF (100 mL). This solution was cooled in an ice bath and LiAlH$_4$ (2M in THF, 22.7 mL, 45.4 mmol) was added dropwise to the stirred mixture at 0° C. The ice bath was removed and the reaction was allowed to stir at room temperature for 5 hours. The reaction was cooled in an ice bath and quenched with acetone (2 mL). After 10 minutes of stirring, it was treated sequentially with water (1.72 mL), 15% aq. NaOH (1.72 mL), followed by water (5.16 mL). The mixture was allowed to stir at room temperatureovernight. The solids were filtered away and rinsed with ethyl acetate. The filtrate was washed with brine (3×), dried over anhydrous sodium sulfate, filtered, and the filtrate was concentrated in vacuo to provide Int-8a. $^H$NMR (500 MHz, CDCl$_3$) δ 4.92 (s, 1H), 3.98-3.88 (m, 2H), 3.85-3.75 (m, 4H), 2.11-2.03 (m, 2H), 1.44 (s, 9H). MS (+ESI) m/z: 218.3.

Step B—Synthesis of Intermediate Compound Int-8b

A solution of Int-8a (860 mg, 3.96 mmol) and 3-(benzyloxy)-4-oxo-4H-pyran-2-carboxylic acid (750 mg, 3.05 mmol) and N,N-diisopropylethylamine (0.85 mL, 4.87 mmol) in dichloromethane (20 mL) was treated with HATU (1.27 g, 3.35 mmol). The mixture was allowed to stir at room temperature for 5 hours. The reaction was diluted with aqueous HCl and extracted with dichloromethane (3×). The combined organics were washed with aqueous sodium bicarbonate (1×), dried over sodium sulfate, filtered, and the filtrate was concentrated in vacuo. The resulting residue was purified using gradient elution on silica gel (50% to 100% ethyl acetate in hexanes) to provide Int-8b. MS (+ESI) m/z: 446.2.

Step C—Synthesis of Intermediate Compound Int-8c

To a solution of Int-8b (1.20 g, 2.69 mmol) in dichloromethane (40 mL) was added trifluoroacetic acid portionwise (6 mL). The mixture was allowed to stir at room temperature for 4 hours and then concentrated in vacuo. The resulting residue was dissolved in EtOH and then concentrated in vacuo. The resulting residue was dissolved in EtOH (200 mL) and heated at 60° C. for 16 hours, 80° C. for 24 hours and then 60° C. for an additional 18 hours. The reaction was concentrated in vacuo and the resulting residue was purified using RP-HPLC to provide Int-8c. $^1$H NMR (500 MHz, CDCl$_3$) δ 7.58-7.54 (m, 3H), 7.37-7.29 (m, 3H), 6.55 (d, J=7.8 Hz, 1H), 5.49 (d, J=10.5 Hz, 1H), 5.35 (d, J=10.3 Hz, 1H), 4.38 (d, J=12.0 Hz, 1H), 4.29 (d, J=12.0 Hz, 1H), 4.22-4.16 (m, 2H), 4.06-4.01 (m, 1H), 3.75 (d, J=11.0 Hz, 1H), 2.50-2.42 (m, 1H), 2.36-2.28 (m, 1H). MS (+ESI) m/z: 328.3.

Step D—Synthesis of Intermediate Compound Int-8d

To a solution of Int-8c (100 mg, 0.31 mmol) in dichloromethane (20 mL) was added ethylamine (70% in water, 1 mL, 12.6 mmol). The vessel was sealed and heated at 65° C. for 2 hours and then concentrated in vacuo. The resulting residue was dissolved in 1:1 acetonitrile and toluene and then concentrated in vacuo to provide Int-8d that was used without further purification. MS (+ESI) m/z: 373.4.

Step E—Synthesis of Intermediate Compound Int-8e

To a solution of Int-8d (100 mg, 0.27 mmol) in dichloromethane (20 mL) was added Dess-Martin periodinane (159 mg, 0.38 mmol) and allowed to stir at room temperature for 90 minutes. The reaction was diluted with aqueous sodium bicarbonate, stirred for 20 minutes and then extracted with dichloromethane (4×). The combined organic layers were dried over sodium sulfate, filtered, and concentrated in vacuo. The resulting residue was dissolved in a 1:1 mixture of acetonitrile and toluene and then concentrated in vacuo to provide Int-8e which was used without further purification. MS (+ESI) m/z: 371.4.

Step F—Synthesis of Intermediate Compound Int-8f

A solution of Int-8e (107 mg, 0.29 mmol) in anhydrous N,N-dimethylformamide (15 mL), under an atmosphere of nitrogen, was treated with sodium hydride (29 mg, 1.16 mmol). The reaction was allowed to stir for 5 minutes at room temperature and then methyl iodide (90 uL, 1.44 mmol) was added. After 30 minutes, the reaction was recharged with sodium hydride (10 mg, 0.42 mmol) and methyl iodide (200 uL, 3.20 mmol). After 30 minutes, the reaction was recharged again with sodium hydride (5 mg, 0.21 mmol) and methyl iodide (100 uL, 1.60 mmol). After 20 minutes, the reaction was cooled in an ice bath, neutralized with aqueous HCl (1N), diluted with brine, and extracted with dichloromethane (4×). The combined organics were dried over sodium sulfate, filtered, and the filtrate was concentrated in vacuo to provide Int-8f which was used without further purification. MS (+ESI) m/z: 385.3.

Step G—Synthesis of Intermediate Compound Int-8g

To a mixture of Int-8f (100 mg, 0.26 mmol) in dichloromethane (10 mL) was added NBS (69 mg, 0.39 mmol). The reaction was allowed to stir at room temperaturein the dark, periodically recharged three times with NBS (25 mg, 0.14 mmol). After 6 hours total, the reaction was diluted with aqueous sodium carbonate (2M) and extracted with dichloromethane (3×). The combined organics layers were dried over sodium sulfate, filtered, and concentrated in vacuo. The resulting residue was purified using column chromatography on silica gel (0-5% MeOH in ethyl acetate) to provide Int-8g. MS (+ESI) m/z: 463.2, 465.2.

Step H—Synthesis of Intermediate Compounds Int-8h-1, Int-8h-2, and Int-8h-3

To a solution of Int-8g (33 mg, 0.071 mmol) in N,N-dimethylformamide (1 mL) was added N-cyclohexyl-N-methylcyclohexanamine (0.05 mL, 0.24 mmol) and (2,4-difluorophenyl) methanamine (60 mg, 0.42 mmol). A stream of CO (g) was bubbled through the solution, bis(tri-t-butylphosphine)palladium(0) (36 mg, 0.071 mmol) was added. The reaction was heated at 90° C. for 3 hours under CO (1 atm). The reaction was filtered, washed with dichloromethane, diluted with aqueous HCl, and extracted with dichloromethane (3×). The combined organic layers were dried over anhydrous sodium sulfate, filtered, and the filtrate was concentrated in vacuo. The resulting residue was purified using gradient elution on silica gel (40-100% ethyl acetate in hexane) to provide the earlier eluting diastereomer A and the later eluting diastereomer B as Int-8h-1 (diastereomer B). The enantiomers of diastereomer A were separated using chiral preparative SFC (2×25 cm Chiralpak AS, 25% iPrOH with 0.1% DEA modifier/75% $CO_2$, 50 mL/min, 220 nM) to provide earlier eluting Int-8h-2 (diastereomer A, enantiomer A) and later eluting Int-8h-3 (diastereomer A, enantiomer B). Int-8h-1 (diastereomer B):$^1$H NMR (500 MHz, $CDCl_3$) δ 10.47 (t, J=5.9 Hz, 1H), 8.47 (s, 1H), 7.63 (d, J=6.8 Hz, 2H), 7.46-7.29 (m, 4H), 6.85-6.78 (m, 2H), 5.46 (d, J=10.0 Hz, 1H), 5.15 (d, J=10.0 Hz, 1H), 4.67 (dd, J=15.1, 5.9 Hz, 1H), 4.59 (dd, J=15.1, 5.9 Hz, 1H), 4.46 (s, 1H), 4.36-4.31 (m, 1H), 4.21-4.13 (m, 2H), 3.83 (d, J=10.0 Hz, 1H), 3.74 (d, J=9.8 Hz, 1H), 3.32 (s, 3H), 3.22-3.14 (m, 1H), 2.78-2.71 (m, 1H), 2.49-2.42 (m, 1H), 1.29 (t, J=7.1 Hz, 3H). MS (+ESI) m/z: 554.2. Int-8h-2/ Int-8h-3 (diastereomer A): $^1$H NMR (500 MHz, $CDCl_3$) δ 10.47 (t, J=5.9 Hz, 1H), 8.76 (s, 1H), 7.63 (d, J=6.8 Hz, 2H), 7.42-7.28 (m, 4H), 6.85-6.77 (m, 2H), 5.47 (d, J=10.0 Hz, 1H), 5.15 (d, J=10.0 Hz, 1H), 4.67 (dd, J=15.1, 6.1 Hz, 1H), 4.58 (dd, J=15.1, 6.1 Hz, 1H), 4.48 (d, J=12.2 Hz, 1H), 4.42 (s, 1H), 4.22-4.15 (m, 2H), 4.09-4.04 (m, 1H), 3.86 (d, J=12.2 Hz, 1H), 3.27 (s, 3H), 3.26-3.18 (m, 1H), 2.34-2.27 (m, 1H), 2.13-2.07 (m, 1H), 1.33 (t, J=7.1 Hz, 3H), MS (+ESI) m/z: 554.3.

Step I—Synthesis of Compound 35

To a solution of Int-8h-1 (diastereomer B) (7.7 mg, 0.014 mmol) in N,N-dimethylformamide (1.2 mL) was added lithium chloride (11 mg, 0.26 mmol) and the reaction was heated at 100° C. for 5 hours. The reaction was diluted with water and directly purified using RP-HPLC to provide Compound 35. $^1$H NMR (499 MHz, DMSO-$d_6$): δ 12.46 (s, 1H), 10.27 (t, J=5.9 Hz, 1H), 8.20 (s, 1H), 7.43-7.38 (m, 1H), 7.26-7.21 (m, 1H), 7.08-7.04 (m, 1H), 5.28 (s, 1H), 4.54 (d J=5.9 Hz, 2H), 4.13-4.06 (m, 2H), 4.04-3.97 (m, 1H), 3.79 (d, J=9.8 Hz, 1H), 3.71 (d, J=9.8 Hz, 1H), 3.44 (s, 3H), 3.33-3.25 (m, 1H), 2.71-2.60 (m, 2H), 1.20 (t, J=7.1 Hz, 3H). MS (+ESI) m/z: 464.2.

Step J—Synthesis of Compound 36 and 37

To a degassed solution of Int-8h-3 (diastereomer A, enantiomer 2) (8 mg, 0.014 mmol) in methanol (5 mL) was added 10% Pd on carbon (8 mg) The reaction was stirred under hydrogen (1 atm) for an hour at room temperature, filtered, and the filtrate was concentrated in vacuo. The resulting residue was purified using RP-HPLC to provide Compound 36. $^1$H NMR (499 MHz, DMSO-$d_6$): δ 12.29 (s, 1H), 10.30 (t, J=5.9 Hz, 1H), 8.47 (s, 1H), 7.43-7.38 (m, 1H), 7.26-7.21 (m, 1H), 7.08-7.04 (m, 1H), 5.26 (s, 1H), 4.53 (d J=5.9 Hz, 2H), 4.43 (d, J=11.7 Hz, 1H), 4.18-4.11 (m, 1H), 4.00-3.91 (m, 3H), 3.38 (s, 3H), 3.33-3.25 (m, 1H), 2.38-2.32 (m, 1H), 2.13-2.08 (m, 1H), 1.25 (t, J=7.0 Hz, 3H). MS (+ESI) m/z: 464.2. A similar procedure was used to convert Int-8h-2 to Compound 37. MS (+ESI) m/z: 464.2.

Example 9

Preparation of Compound 38

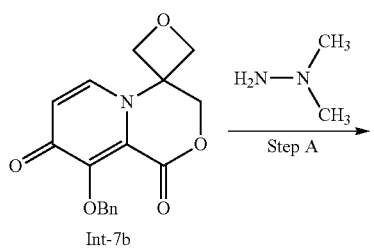

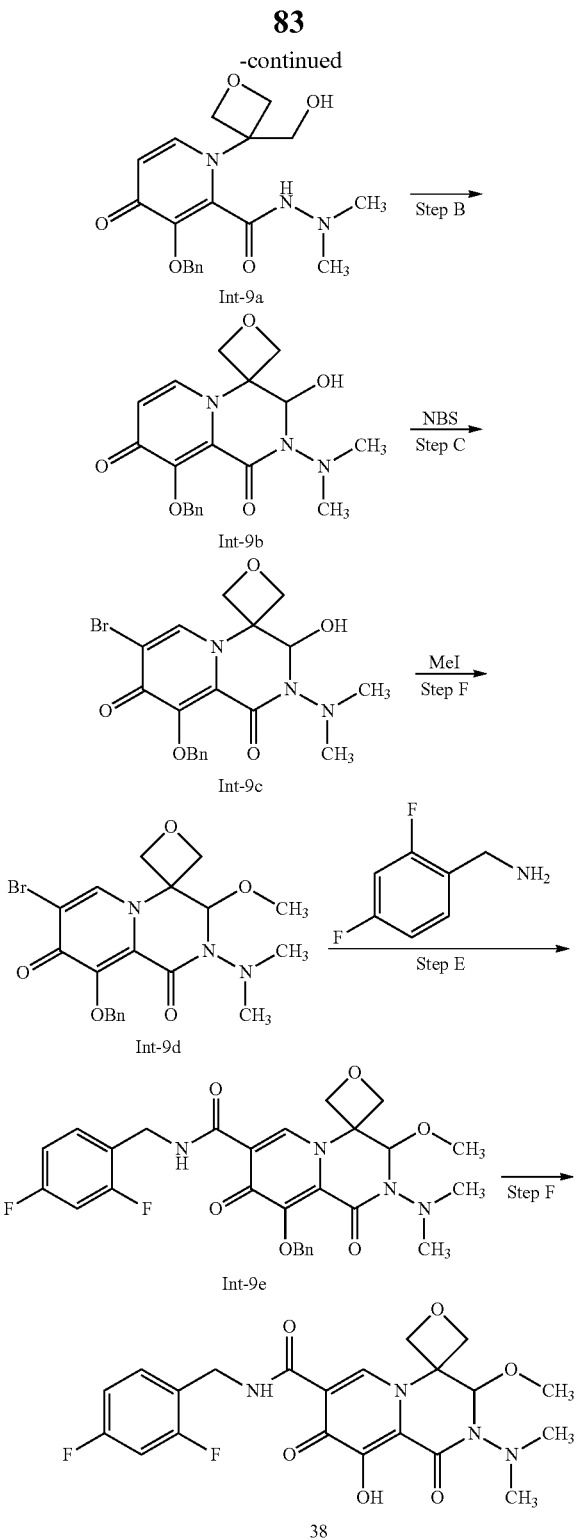

Step A—Synthesis of Intermediate Compound Int-9a

A solution of 1,1-dimethylhydrazine (178 mg, 2.97 mmol) in $CH_2Cl_2$ (10 mL) under an atmosphere of nitrogen gas was treated with trimethylaluminum (1.48 mL, 2.97 mmol). The mixture was allowed to stir at 18° C. for 20 minutes and was then treated with a solution of Int-7b (310 mg, 1 mmol) in dichloromethane (5 mL). The mixture was allowed to stir at 18° C. for 16 hours, quenched with water (5 drops), diluted with dichloromethane (10 mL) and filtered. The filtrate was dried over anhydrous sodium sulfate and concentrated in vacuo. The crude residue was purified using preparative TLC on silica gel (dichloromethane:methanol=10:1) to provide Int-9a. $^1$H NMR (400 MHz, $CDCl_3$) δ 7.30-7.35 (m, 2H), 7.24-7.28 (m, 3H), 6.90 (d, J=8.0 Hz, 1H), 6.24 (d, J=8.0 Hz, 1H), 4.92-4.98 (m, 4H), 4.46 (d, J=4.4 Hz, 2H), 4.32 (s, 2H), 2.40 (s, 6H).

Step B—Synthesis of Intermediate Compound Int-9b

A solution of Int-9a in dichloromethane (10 mL) was treated with dimethylsulfoxide (0.51 mL, 7.14 mmol), N,N-diisopropylethylamine (0.84 mL, 4.64 mmol) and $PySO_3$ (682 mg, 4.29 mmol) at 5° C. The mixture was allowed to stir at 25° C. for 16 hours and then concentrated in vacuo. The resulting residue was purified using preparative TLC on silica gel (dichloromethane:methanol=10:1) to provide Int-9b. $^1$H NMR (400 MHz, $CDCl_3$) δ 7.50-7.56 (m, 2H), 7.42 (d, J=7.2 Hz, 1H), 7.25-7.31 (m, 3H), 6.44 (d, J=8.0 Hz, 1H), 5.51 (s, 1H), 5.04 (d, J=10.0 Hz, 1H), 4.86 (d, J=9.2 Hz, 1H), 4.72 (d, J=9.2 Hz, 1H), 4.54-4.57 (m, 2H), 4.38 (d, J=6.8 Hz, 1H), 2.96 (s, 6H). MS (+ESI) m/z: 372.1

Step C—Synthesis of Intermediate Compound Int-9c

A solution of Int-9b (60 mg, 0.16 mmol) in dichloromethane (8 mL) was treated with N-bromosuccinimide (57.6 mg, 0.32 mmol) at 0° C. The mixture was allowed to stir at 25° C. for 2 hours, concentrated in vacuo and the resulting residue was purified using preparative TLC on silica gel (dichloromethane:methanol=10:1) to provide Int-9c. $^1$H NMR (400 MHz, $CDCl_3$) δ 7.78 (s, 1H), 7.53 (d, J=6.8 Hz, 2H), 7.30-7.36 (m, 3H), 5.44 (s, 1H), 5.02 (d, J=9.2 Hz, 1H), 4.87 (d, J=8.8 Hz, 1H), 4.55-4.64 (m, 3H), 4.39 (d, J=7.2 Hz, 1H), 2.98 (s, 6H). MS (+ESI) m/z: 448.1, 450.1

Step D—Synthesis of Intermediate Compound Int-9d

A solution of Int-9c (40 mg, 0.088 mmol) in N,N-dimethylformamide (3 mL) at 0° C. was treated with NaH (10.7 mg, 0.27 mmol) and iodomethane (0.05 mL, 0.888 mmol). The reaction mixture was allowed to stir at 25° C. for 1 hour, quenched with water (10 mL) and the mixture was extracted with dichloromethane (10 mL×4). The combined organic layers were dried over anhydrous sodium sulfate, concentrated in vacuo and the resulting residue was purified using preparative TLC on silica gel (dichloromethane:ethyl acetate=1:1) to provide Int-9d. $^1$H NMR (400 MHz, $CDCl_3$) δ 8.04 (s, 1H), 7.50 (d, J=6.4 Hz, 2H), 7.22-7.28 (m, 3H), 5.45 (d, J=6.4 Hz, 1H), 5.06-5.13 (m, 2H), 5.03 (s, 1H), 4.69 (d, J=8.8 Hz, 1H), 4.62 (d, J=8.0 Hz, 1H), 4.51 (d, J=6.8 Hz, 1H), 3.40 (s, 3H), 2.90 (s, 6H). MS (+ESI) m/z: 464.0, 466.0

Step E—Synthesis of Intermediate Compound Int-9e

A mixture of Int-9d (10 mg, 0.022 mmol), N,N-diisopropylethylamine (0.011 mL, 0.065 mmol) and (2,4-difluorophenyl)methanamine (15.4 mg, 0.11 mmol) in dimethylsulfoxide (1 mL) and methanol (4 mL) was added $Pd(Ph_3P)_4$ (12.4 mg, 10.8 μmol) under $N_2$. The mixture was allowed to stir at 90° C. for 2 hours under carbon monoxide (1 atm) cooled to room temperature and concentrated in vacuo. The resulting residue was dissolved in ethyl acetate, filtered and concentrated in vacuo. The resulting residue was purified using preparative TLC on silica gel (ethyl acetate:petroleum ether=1.5:1) to provide Int-9e. $^1$H NMR (400 MHz, $CDCl_3$) δ 10.33 (s, 1H), 8.77 (s, 1H), 7.46 (d, J=6.8 Hz, 2H), 7.11-7.31 (m, 4H), 6.73-6.78 (m, 2H), 5.33-5.41 (m, 2H), 5.06-5.12 (m, 2H), 4.50-4.63 (m, 5H), 3.61 (s, 3H), 2.90 (s, 6H). MS (+ESI) m/z: 555.2

Step F—Synthesis of Compound 38

A solution of Int-9e (5 mg, 9 μmol) and lithium chloride (0.4 mg, 9 μmol) in N,N-dimethylformamide (2 mL) was allowed to stir at 100° C. for 1 hour, cooled to room temperature and concentrated in vacuo. The resulting residue was purified using RP-HPLC to provide Compound 38. ¹H NMR (400 MHz, CDCl₃) δ 10.31 (s, 1H), 8.79 (s, 1H), 7.33-7.37 (m, 1H), 6.78-6.82 (m, 2H), 5.48 (d, J=8.8 Hz, 1H), 5.26 (s, 1H), 4.70 (d, J=8.0 Hz, 1H), 4.64 (d, J=6.0 Hz, 2H), 4.56 (d, J=6.8 Hz, 1H), 4.44 (d, J=7.2 Hz, 1H), 3.71 (s, 3H), 3.02 (s, 6H). MS (+ESI) m/z: 465.1

Example 10

Preparation of Compounds 39 and 40

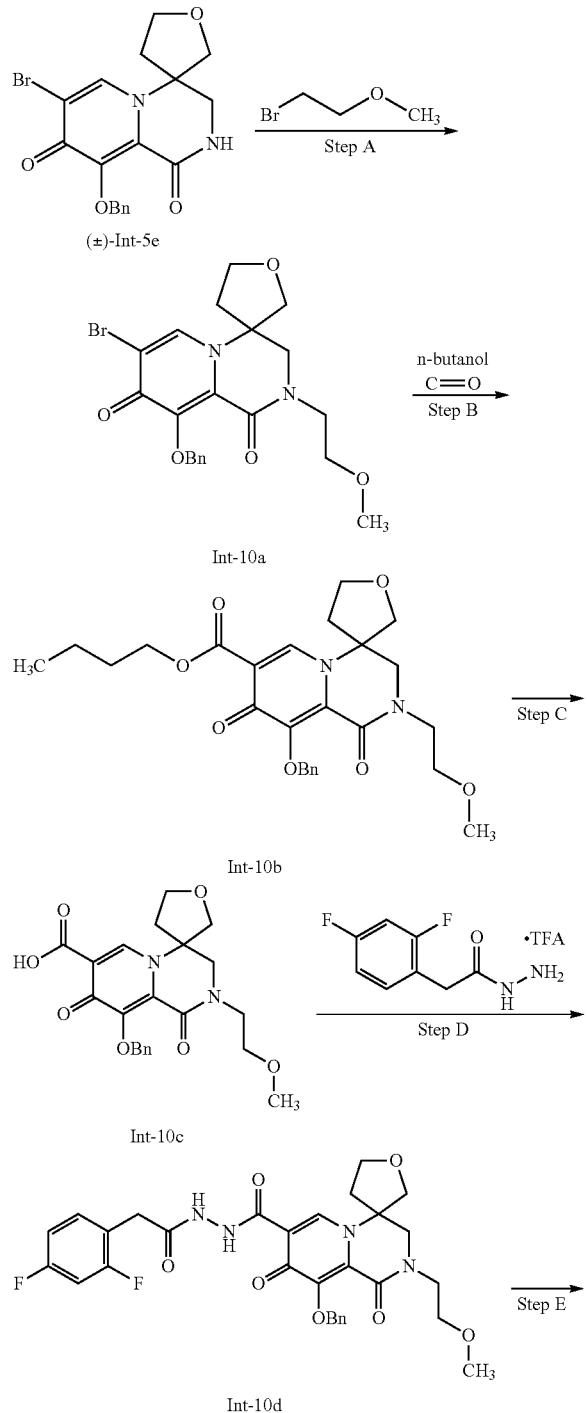

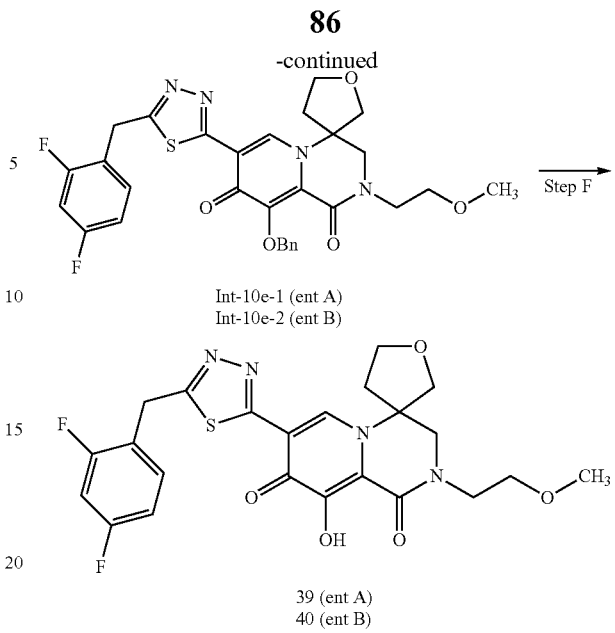

Int-10e-1 (ent A)
Int-10e-2 (ent B)

39 (ent A)
40 (ent B)

Step A—Synthesis of Intermediate Compound Int-10a

A solution of (±)-Int-5e (1.00 g, 2.47 mmol) in N,N-dimethylformamide under nitrogen at 0° C. was treated with a solution of LiHMDS (1M in THF, 2.71 mL, 2.71 mmol). The mixture was allowed to stir at 0° C. for 20 minutes and was then treated with 1-bromo-2-methoxyethane (0.371 mL, 3.95 mmol). The mixture was allowed to stir at room temperature for 16 hours, treated with 1N aqueous HCl until pH 3 and extracted with dichloromethane. The combined organic layers were dried over anhydrous sodium sulfate, filtered and concentrated in vacuo. The resulting residue was purified using column chromatography on silica gel (0-5% methanol/ ethyl acetate) to provide Int-10a. MS (+ESI) m/z: 463.3, 465.3.

Step B—Synthesis of Intermediate Compound Int-10b

A solution of Int-10a (315 mg, 0.680 mmol), butan-1-ol (0.622 ml, 6.80 mmol) and N-cyclohexyl-N-methylcyclohexanamine (0.288 ml, 1.36 mmol) in N,N-dimethylformamide (6.80 mL) was sub-surface sparged with nitrogen gas for 3 minutes, treated with bis(tri-t-butylphosphine)palladium(0) (174 mg, 0.340 mmol) and sparging was continued for 1 minute The flask was sealed with a rubber septum, evacuated and backfilled with carbon monoxide. The mixture was stirred under carbon monoxide (1 atm) at 90° C. for 5.5 hours. The mixture was cooled to room temperature, filtered and the filtrate was directly purified using RP-HPLC to provide Int-10b. MS (+ESI) m/z: 485.4.

Step C—Synthesis of Intermediate Compound Int-10c

A solution of Int-10b (150 mg, 0.310 mmol) in THF (2 mL), methanol (0.5 mL), water (0.5 mL) was treated with lithium hydroxide hydrate (65.0 mg, 1.548 mmol) and allowed to stir at 40° C. for 40 minutes. The mixture was concentrated in vacuo and azeotropically dried with acetonitrile to provide Int-10c that was used without further purification. MS (+ESI) m/z: 429.3.

Step D—Synthesis of Intermediate Compound Int-10d

A mixture of Int-10c (133 mg, 0.310 mmol), 2-(2,4-difluorophenyl)acetohydrazide 2,2,2-trifluoroacetate (103 mg, 0.341 mmol) and HATU (130 mg, 0.341 mmol) in N,N-dimethylformamide (1.55 mL) was treated at room temperature with DIPEA (0.163 ml, 0.931 mmol). The mixture was allowed to stir for 10 minutes at room temperature and was then directly purified using RP-HPLC to provide Int-10d. MS (+ESI) m/z: 597.4.

Step E—Synthesis of Intermediate Compound Int-10e-1 and Intermediate Compound Int-10e-2

A solution of Int-10d (69.3 mg, 0.116 mmol) in THF (1.16 mL) was treated with Lawesson's reagent (56.4 mg, 0.139 mmol) and allowed to stir at 60° C. for 16 hours. The mixture was concentrated in vacuo and the resulting residue was purified using column chromatography on silica gel (0-5% MeOH in dichloromethane) to provide the product as the racemate. Separation of the enantiomers by chiral SFC (Chiralcel OJ-H; 30% isopropanol with 0.1% diethylamine in SC—CO$_2$; 80 mL/min; 254 nm) provided the earlier eluting Int-10e-1 (ent A) and the later eluting Int-10e-2 (ent B). MS (+ESI) m/z: 595.4.

Step E—Synthesis of Compound 39

A solution of Int-10e-1 (15 mg, 0.025 mmol) in dichloromethane (0.20 mL) was treated with trifluoroacetic acid (0.194 mL) and allowed to stir at room temperature for 25 minutes. The mixture was concentrated in vacuo and the resulting residue was purified using RP-HPLC to provide Compound 39. MS (+ESI) m/z: 505.3. $^1$H NMR (500 MHz, CDCl$_3$): δ 8.78 (1H, s), 7.37 (1H, q, J=7.5 Hz), 6.85-6.90 (2H, m), 4.51 (2H, s), 4.31 (1H, d, J=10.9 Hz), 4.26 (1H, q, J=8.2 Hz), 4.09 (1H, q, J=7.5 Hz), 4.01 (1H, d, J=13.3 Hz), 3.91 (2H, t, J=12.4 Hz), 3.78-3.81 (2H, m), 3.69-3.71 (2H, m), 3.41 (3H, s), 2.43-2.49 (2H, m).

Step F—Synthesis of Compound 40

A solution of Int-10e-2 (12.1 mg, 0.020 mmol) in dichloromethane (0.157 mL) was treated with trifluoroacetic acid (0.157 mL) and allowed to stir at room temperature for 25 minutes. The mixture was concentrated in vacuo and the resulting residue was purified using RP-HPLC to provide Compound 40. MS (+ESI) m/z: 505.3. $^1$H NMR (500 MHz, CDCl$_3$): δ 8.78 (1H, s), 7.35-7.40 (1H, m), 6.86-6.91 (2H, m), 4.53 (2H, s), 4.33 (1H, d, J=11.1 Hz), 4.24-4.29 (1H, m), 4.06-4.11 (1H, m), 4.02 (1H, d, J=13.4 Hz), 3.91 (2H, t, J=12.6 Hz), 3.81 (2H, q, J=4.7 Hz), 3.69-3.71 (2H, m), 3.41 (3H, s), 2.45-2.48 (2H, m).

Example 11

Preparation of Intermediate Compounds 41 and 42

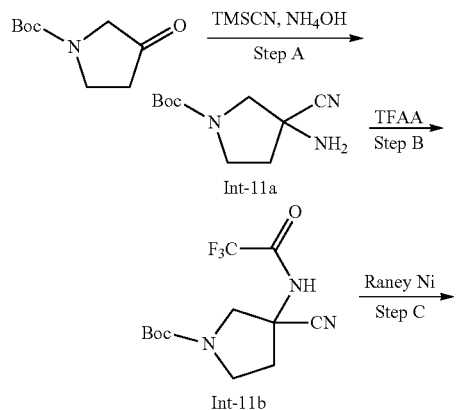

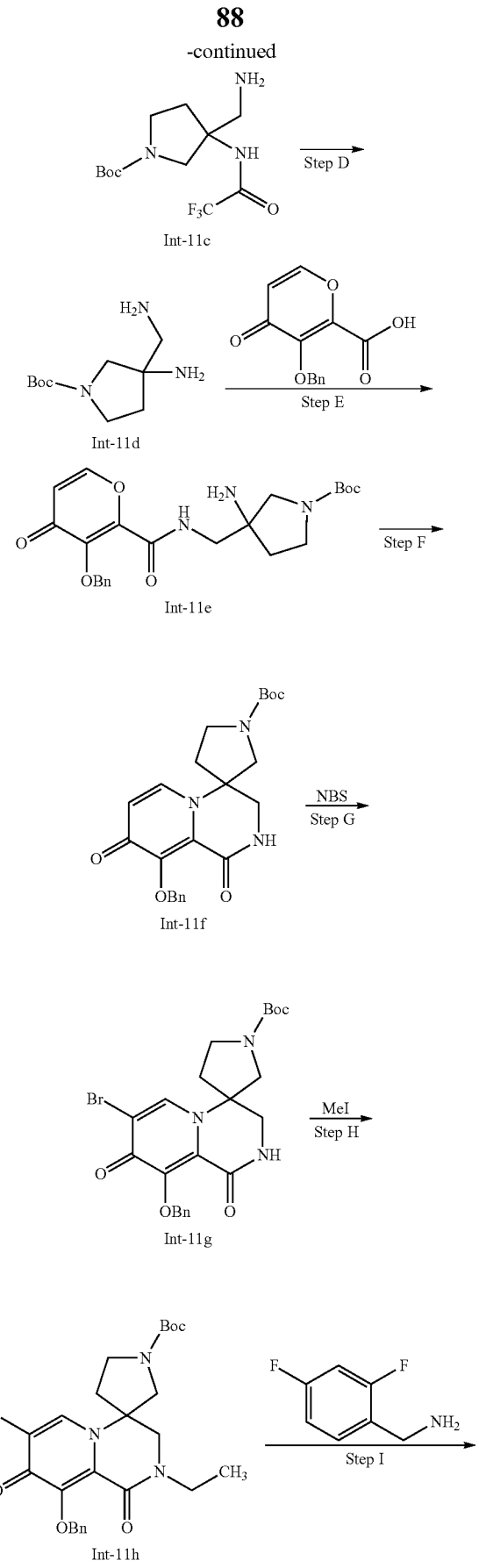

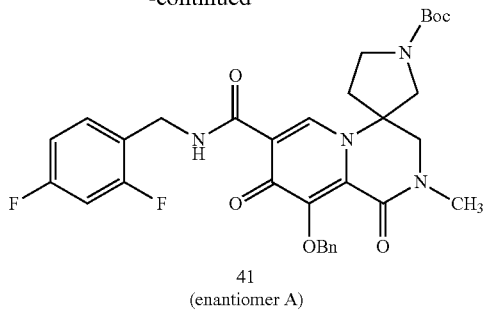

41
(enantiomer A)

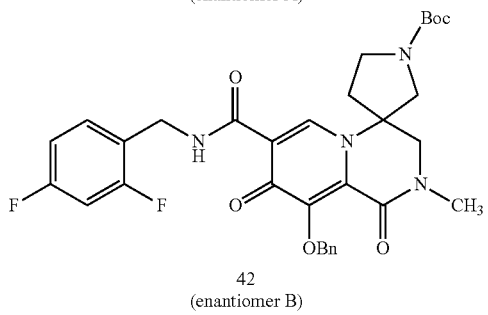

42
(enantiomer B)

Step A—Synthesis of Intermediate Compound Int-11a

A solution of compound tert-butyl 3-oxopyrrolidine-1-carboxylate (500 mg, 2.70 mmol) and ammonia in THF (2M, 3 mL) was stirred at 28° C. for 2 h, treated with trimethylsilanecarbonitrile (281 mg, 2.83 mmol) and stirred at 28° C. for 12 h. The mixture was concentrated to afford crude Int-11a which was used directly in the next step without further purification.

Step B—Synthesis of Intermediate Compound Int-11b

To a solution of compound Int-11a (500 mg, 2.367 mmol) and pyridine (1872 mg, 23.67 mmol) in tetrahydrofuran (10 mL) was added 2,2,2-trifluoroacetic anhydride (597 mg, 2.84 mmol) at 0° C. The mixture was stirred at 28° C. for 3 h, concentrated and the residue was purified by column chromatography on silica gel (25% to 50% ethyl acetate in petroleum ether) to afford Int-11b: $^1$H NMR (400 MHz, CDCl$_3$) δ 3.92-4.05 (m, 1H), 3.76-3.89 (m, 1H), 3.39-3.71 (m, 2H), 2.45-2.72 (m, 2H), 1.46 (s, 9H).

Step C—Synthesis of Intermediate Compound Int-11c

To a solution of compound Int-11b (400mg, 1.302 mmol) in ethanol (10 mL) was added Raney nickel (76 mg, 1.302 mmol) and the mixture was stirred under hydrogen (1 atm) at 28° C. for 2 h. The mixture was filtered and the filtrate was concentrated to afford crude Int-11c which was used directly in next step without further purification.

Step D—Synthesis of Intermediate Compound Int-11d

To a solution of compound Int-11c (100 mg, 0.321 mmol) in methanol (15 mL) was added an aqueous solution of KOH (2.8 mL, 14.00 mmol) at 25° C. The mixture was stirred at 80° C. for 5 h and then concentrated. The residue was dissolved in dichloromethane (20 mL), filtered and the filtrate was concentrated to afford crude Int-11d which was used in the next step without further purification. $^1$H NMR (400 MHz, CDCl$_3$) δ 3.34-3.54 (m, 2H), 3.07-3.31 (m, 2H), 2.68 (s, 2H), 2.57-2.79 (m, 1H), 1.74-1.86 (m, 1H), 1.58-1.70 (m, 1H), 1.43 (s, 9H).

Step E—Synthesis of Intermediate Compound Int-11e

To a solution of 3-(benzyloxy)-4-oxo-4H-pyran-2-carboxylic acid (1 g, 4.06 mmol) in N,N-dimethylformamide (20 mL) was added Int-11d (1.312 g, 6.09 mmol), N,N-diisopropylethylamine (2.128 mL, 12.18 mmol) and 7-azabenzotriazol-1-yloxytris(dimethylamino)phosphonium hexafluorophosphate (AOP) (2.160 g, 4.87 mmol) at 0° C. The mixture was stirred at 0° C. for 20 minutes, treated with water (50 mL) and extracted with ethyl acetate (50 mL×3). The organic phase was dried over anhydrous Na$_2$SO$_4$, filtered and the filtrate was concentrated. The residue was purified by preparative TLC on silica gel (5% methanol in dichloromethane) to afford Int-11e. $^1$H NMR (400 MHz, CDCl$_3$) 8.32 (s, 1H), 7.63-7.76 (m, 1H), 7.32 (s, 5H), 6.26-6.43 (m, 1H), 5.37 (s, 2H), 3.27-3.53 (m, 6H), 1.97-2.06 (m, 1H), 1.88 (s, 1H), 1.42 (s, 9H). MS (+ESI) m/z: 444.2.

Step F—Synthesis of Intermediate Compound Int-11f

To a solution of Int-11e (1 g, 2.255 mmol) in ethanol (80 mL) was added trifluoroacetic acid (0.035 mL, 0.451 mmol). The mixture was stirred at 80° C. for 3 days and then concentrated.

The residue was purified by column chromatography on silica gel (5% methanol in dichloromethane). Further purification by preparative TLC on silica gel (7% methanol in dichloromethane) afforded Int-11f. $^1$H NMR (400 MHz, CDCl$_3$) δ 7.73 (s, 1H), 7.52 (d, J=7.2 Hz, 2H), 7.16-7.29 (m, 4H), 6.43 (d, J=8.0 Hz, 1H), 5.27 (d, J=10.0 Hz, 1H), 5.13 (d, J=10.0 Hz, 1H), 3.51-3.72 (m, 2H), 3.27-3.40 (m, 3H), 3.10 (s, 1H), 2.17 (dd, J=6.4, 13.0 Hz, 1H), 1.95 (s, 1H), 1.32-1.50 (m, 9H). MS (+ESI) m/z: 426.2.

Step G—Synthesis of Intermediate Compound Int-11g

A solution of Int-11f (130 mg, 0.306 mmol) in dichloromethane (3 mL) was treated with NBS (109 mg, 0.611 mmol) at 0° C. The mixture was stirred at 25° C. for 3 hours, quenched with aqueous Na$_2$SO$_3$ (3 mL) and extracted with dichloromethane (10 mL×3). The combined organic portions were dried over Na$_2$SO$_4$, filtered and the filtrate was concentrated. The residue was purified by preparative TLC on silica gel (7% methanol in dichloromethane) to give Int-11g. $^1$H NMR (400 MHz, CDCl$_3$) δ 7.56-7.60 (m, 2H), 7.22-7.37 (m, 3H), 5.21-5.30 (m, 1H), 5.12 (d, J=9.6 Hz, 1H), 3.79 (d, J=12.8 Hz, 1H), 3.34-3.65 (m, 5H), 3.13-3.22 (m, 1H), 2.19-2.28 (m, 1H), 1.98-2.08 (m, 1H), 1.43-1.57 (m, 9H). MS (+ESI) m/z: 504.1.

Step H—Synthesis of Intermediate Compound Int-11h

A solution of Int-11g (200 mg, 0.397 mmol) in tetrahydrofuran (4 mL) was treated with a solution of LiHMDS in tetrahydrofuran (1M, 0.595 mL, 0.595 mmol) at -78° C. under nitrogen. The mixture was stirred at -78° C. for 30 minutes, treated with MeI (0.037 mL, 0.595 mmol), stirred at 0° C. for 1.5 hours and then quenched with water (10 mL). The mixture was extracted with ethyl acetate (10 mL×3) and the organic phase was dried over anhydrous Na$_2$SO$_4$, filtered and the filtrate was concentrated. The residue was purified by preparative TLC on silica gel (50% ethyl acetate in dichloromethane) to afford Int-11h. $^1$H NMR (400 MHz, CDCl$_3$) δ 7.64 (d, J=7.2 Hz, 2H), 7.54 (s, 1H), 7.27-7.39 (m, 3H), 5.21 (d, J=7.6 Hz, 1H), 5.08-5.15 (m, 1H), 3.87 (d, J=13.2 Hz, 1H), 3.59-3.67 (m, 1H), 3.44-3.52 (m, 3H), 3.29 (d, J=6.4 Hz, 1H), 2.71-2.95 (m, 3H), 2.29 (s, 1H), 2.11 (s, 1H), 1.49 (s, 9H). MS (+ESI) m/z: 520.1.

Step I—Synthesis of Compound 41 and 42

To a solution of Int-11h (100 mg, 0.193 mmol) in dimethylsulfoxide (5 mL) were added (2,4-difluorophenyl)methanamine (138 mg, 0.965 mmol), N,N-diisopropylethylamine (0.337 mL, 1.929 mmol) and Pd(Ph$_3$P)$_4$ (111 mg, 0.096 mmol). The mixture was stirred at 90° C. for 7 hours under carbon monoxide (1 atm), cooled to rt and filtered. The filtrate was diluted with water (10 mL) and extracted with ethyl acetate (10 mL×3). The organic layer was washed with 1 M HCl (10 mL) and brine (10 mL), dried over anhydrous Na₂SO₄, filtered and the filtrate was concentrated. The residue was concentrated and purified by preparative TLC on silica gel (50% ethyl acetate in dichloromethane) to give the product as the racemate. MS (+ESI) m/z: 609.3.

Resolution to the enantiomers was accomplished with SFC (AD, 3×25 cm, 55% ethanol with 0.1% ammonium hydroxide in SC—CO₂, 80 mL/min, 220 nm) to give compound 41 (enantiomer A) and compound 42 (enantiomer B).

Compound 41: ¹H NMR (400 MHz, CDCl₃) δ 10.42 (s, 1H), 8.50 (d, J=18.0 Hz, 1H), 7.61 (d, J=7.2 Hz, 2H), 7.26-7.45 (m, 4H), 6.73-6.87 (m, 2H), 5.28 (s, 2H), 4.63 (d, J=5.6 Hz, 2H), 3.46-3.68 (m, 6H), 3.14 (s, 3H), 2.44-2.54 (m, 1H), 2.19 (s, 1H), 1.48 (s, 9H)

Compound 42: ¹H NMR (400 MHz, CDCl₃) δ 10.41 (s, 1H), 8.48 (d, J=20.0 Hz, 1H), 7.60 (d, J=7.2 Hz, 2H), 7.25-7.42 (m, 4H), 6.75-6.86 (m, 2H), 5.26 (s, 2H), 4.62 (d, J=5.6 Hz, 2H), 3.49-3.82 (m, 6H), 3.12 (s, 3H), 2.41-2.51 (m, 1H), 2.17 (s, 1H), 1.48 (s, 9H)

Example 12

Preparation of Intermediate Compound 43

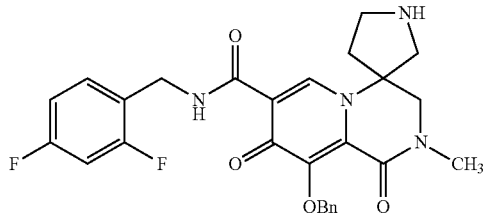 [SMILES: CN1CC2(CCNC2)n2cc(C(=O)NCc3ccc(F)cc3F)c(=O)c(OCc3ccccc3)c2C1=O]

To a solution of compound 41 (enantiomer A) (20 mg, 0.033 mmol) in ethyl acetate (1.8 mL) was added a solution of HCl in ethyl acetate (4 M, 0.6 mL) at 0° C. The mixture was stirred at 25° C. for 1.5 h and then concentrated. The residue was purified by preparative TLC on silica gel (7% methanol in dichloromethane) to afford compound 43. ¹H NMR (400 MHz, CDCl₃) δ 10.52 (s, 1H), 8.77 (s, 1H), 7.55-7.68 (m, 1H), 7.62 (d, J=7.2 Hz, 2H), 7.27-7.44 (m, 4H), 6.74-6.88 (m, 2H), 5.29 (s, 2H), 4.63 (d, J=5.6 Hz, 2H), 3.46-3.63 (m, 3H), 3.37 (d, J=12.0 Hz, 2H), 3.09-3.26 (m, 5H), 2.30 (dd, J=6.8, 13.6 Hz, 1H), 2.08-2.17 (m, 3H). MS (+ESI) m/z: 509.3.

Example 13

Preparation of Intermediate Compound 44

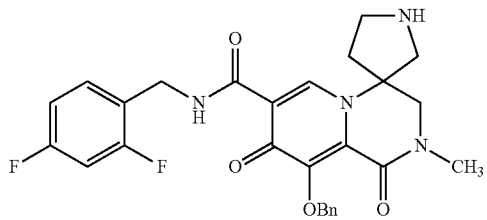 [SMILES: CN1CC2(CCNC2)n2cc(C(=O)NCc3ccc(F)cc3F)c(=O)c(OCc3ccccc3)c2C1=O]

To a solution of compound 42 (enantiomer B) (25 mg, 0.041 mmol) in ethyl acetate (0.9 mL) was added a solution of HCl in ethyl acetate (4 M, 0.3 mL) at 0° C. The mixture was stirred at 25° C. for 1.5 h and then concentrated. The residue was purified by preparative TLC on silica gel (7% methanol in dichloromethane) to afford compound 44. ¹H NMR (400 MHz, CDCl₃) δ 10.51 (brs, 1H), 8.76 (s, 1H), 7.62 (d, J=7.2 Hz, 2H), 7.27-7.43 (m, 4H), 6.76-6.85 (m, 2H), 5.24-5.31 (m, 2H), 4.62 (d, J=5.6 Hz, 2H), 3.46-3.64 (m, 2H), 3.32-3.41 (m, 2H), 3.10-3.25 (m, 5H), 2.29 (td, J=6.8, 13.6 Hz, 1H), 2.09-2.19 (m, 1H), 2.00-2.08 (m, 1H). MS (+ESI) m/z: 509.2.

Example 14

Preparation of Compound 45

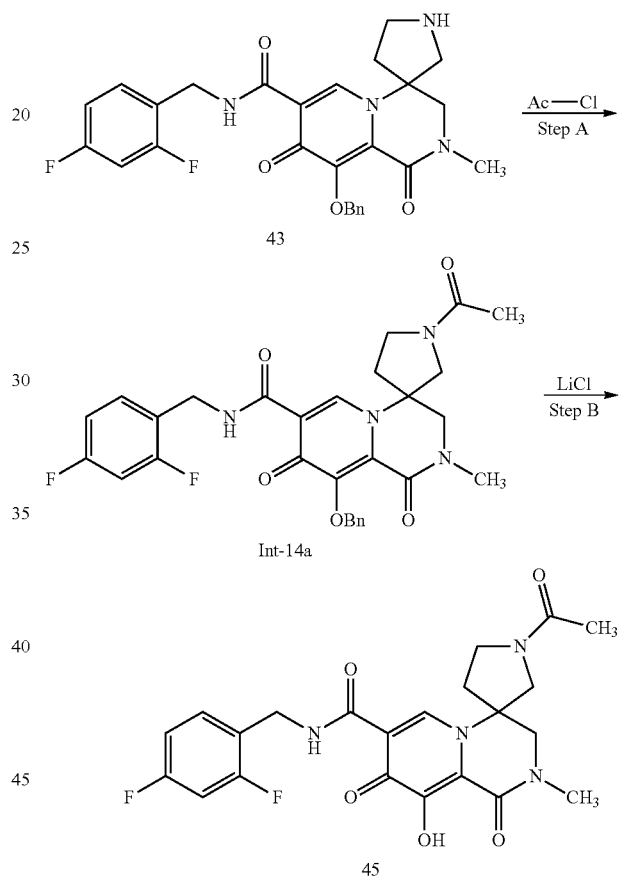

Step A—Synthesis of Intermediate Compound Int-14a

To a solution of compound 43 (15 mg, 0.029 mmol) in dichloromethane (0.5 mL) was added triethylamine (0.012 mL, 0.088 mmol) and acetyl chloride (2.78 mg, 0.035 mmol) at 0° C. The mixture was stirred at 25° C. for 5 minutes, quenched with methanol and concentrated. The residue was purified by preparative TLC on silica gel (7% methanol in dichloromethane) to afford Int-14a. ¹H NMR (400 MHz, CDCl₃) δ 10.31-10.45 (m, 1H), 8.38-8.54 (m, 1H), 7.61 (d, J=7.2 Hz, 2H), 7.29-7.42 (m, 4H), 6.75-6.88 (m, 2H), 5.24-5.33 (m, 2H), 4.63 (d, J=5.6 Hz, 2H), 4.06 (d, J=13.6 Hz, 1H), 3.53-3.82 (m, 5H), 3.12-3.20 (m, 3H), 2.55-2.63 (m, 1H), 2.33 (td, J=9.2, 14.09 Hz, 1H), 2.09-2.19 (m, 3H). MS (+ESI) m/z: 551.2.

Step B—Synthesis of Compound 45

A solution of Int-14a (10 mg, 0.018 mmol) and LiCl (30.8 mg, 0.727 mmol) in N,N-dimethylformamide (1 mL) was stirred at 80° C. for 1.5 hours. The mixture was cooled to rt and concentrated. The residue was purified by RP-HPLC to afford compound 45. ¹H NMR (400 MHz, CDCl₃) δ 12.80 (brs, 1H), 10.31-10.42 (m, 1H), 8.35-8.48 (m, 1H), 7.35 (d, J=7.2 Hz, 1H), 6.75-6.87 (m, 2H), 4.63 (d, J=4.4 Hz, 2H), 4.08 (d, J=10.4 Hz, 1H), 3.77 (s, 5H), 3.23 (s, 3H), 2.65 (s, 1H), 2.25 (s, 1H), 2.07-2.17 (m, 3H). MS (+ESI) m/z: 461.2.

Example 15

Preparation of Compound 46

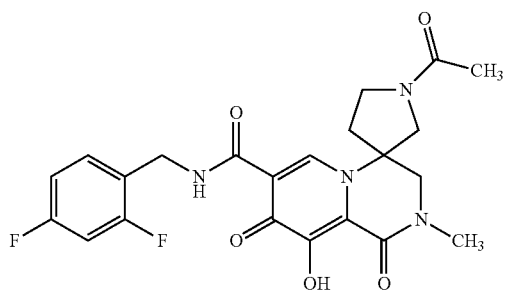 [SMILES: CC(=O)N1CCC2(CN(C)C(=O)c3c(O)c(=O)c(C(=O)NCc4ccc(F)cc4F)cn32)C1]

Compound 46 was prepared from compound 44 in a similar manner to Example 14. ¹H NMR (400 MHz, CDCl₃) δ 12.76 (brs, 1H), 10.28-10.40 (m, 1H), 8.34-8.47 (m, 1H), 7.31-7.40 (m, 1H), 6.75-6.88 (m, 2H), 4.62 (d, J=5.2 Hz, 2H), 4.07 (d, J=13.6 Hz, 1H), 3.68-3.87 (m, 5H), 3.22 (s, 3H), 2.65 (d, J=7.2 Hz, 1H), 2.32-2.40 (m, 1H), 2.06-2.15 (m, 3H). MS (+ESI) m/z: 461.2.

Example 16

Preparation of Compound 47

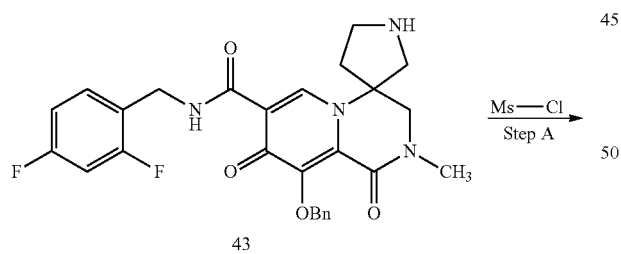

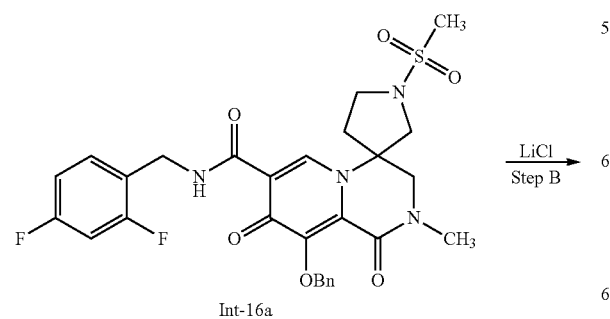

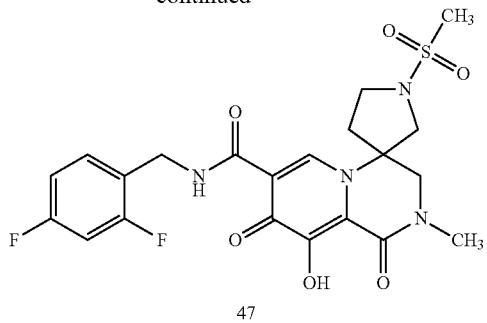
47

Step A—Synthesis of Intermediate Compound Int-16a

To a solution of compound 43 (22 mg, 0.043 mmol) in dichloromethane (4 mL) was added triethylamine (0.018 mL, 0.130 mmol) and methanesulfonyl chloride (5.06 μL, 0.065 mmol) at 0° C. The mixture was stirred at 0° C. for 1 h, quenched with water (10 mL) and extracted with dichloromethane (10 mL×3). The organic phase was dried over anhydrous Na₂SO₄, filtered and the filtrate was concentrated. The residue was purified by preparative TLC (50% ethyl acetate in dichloromethane) to afford Int-16a. ¹H NMR (400 MHz, CDCl₃) δ 10.39 (t, J=5.2 Hz, 1H), 8.51 (s, 1H), 7.59 (d, J=7.2 Hz, 2H), 7.28-7.40 (m, 4H), 6.77-6.87 (m, 2H), 5.23 (s, 2H), 4.62 (d, J=5.6 Hz, 2H), 3.73-3.82 (m, 2H), 3.49-3.63 (m, 4H), 3.46-3.47 (m, 3H), 3.12 (s, 3H), 2.44-2.52 (m, 1H), 2.20-2.29 (m, 1H). MS (+ESI) m/z: 587.2.

Step B—Synthesis of Compound 47

A solution of compound Int-16a (10 mg, 0.017 mmol) and LiCl (28.9 mg, 0.682 mmol) in N,N-dimethylformamide (1 mL) was stirred at 80° C. for 1.5 hours under nitrogen. The mixture was concentrated and the residue was purified by RP-HPLC to afford compound 47. ¹H NMR (400 5 MHz, CDCl₃) δ 10.44 (brs, 1H), 8.53 (s, 1H), 7.31-7.37 (m, 1H), 6.76-6.86 (m, 2H), 4.63 (d, J=5.2 Hz, 2H), 3.90 (d, J=12.0 Hz, 2H), 3.69-3.79 (m, 2H), 3.53 (d, J=11.2 Hz, 2H), 3.23 (s, 3H), 3.03 (s, 3H), 2.65 (s, 1H), 2.27-2.35 (m, 1H). MS (+ESI) m/z: 497.1.

Example 17

Preparation of Compound 48

Compound 48 was prepared from compound 44 in a similar manner to Example 16. ¹H NMR (400 MHz, CDCl₃) δ 10.39 (brs, 1H), 8.52 (s, 1H), 7.31-7.38 (m, 1H), 6.77-6.85 (m, 2H), 4.63 (d, J=5.2 Hz, 2H), 3.90 (d, J=12.0 Hz, 2H), 3.69-3.79 (m, 2H), 3.53 (d, J=11.6 Hz, 2H), 3.23 (s, 3H), 3.03 (s, 3H), 2.64 (s, 1H), 2.27-2.34 (m, 1H). MS (+ESI) m/z: 497.1.

Example 18

Preparation of Compound 49

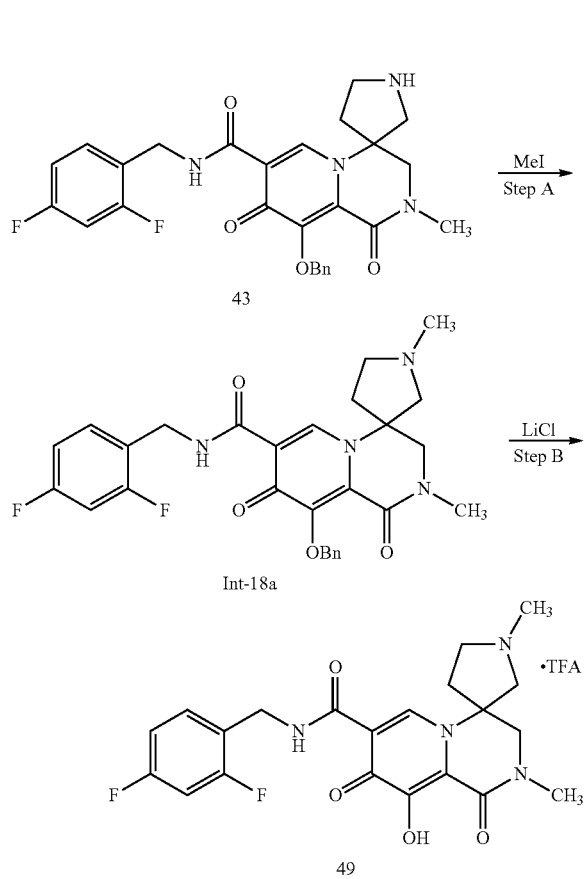

Step A—Synthesis of Intermediate compound Int-18a

To a solution of compound 43 (20 mg, 0.039 mmol) in N,N-dimethylformamide (0.5 mL) was added $K_2CO_3$ (16.31 mg, 0.118 mmol) and MeI (3.69 µL, 0.059 mmol) at 0° C. under nitrogen. The mixture was stirred at 25° C. for 1.5 h and then extracted with ethyl acetate (10 mL) and water (3×10 mL). The combined organics were washed with brine, dried over anhydrous $Na_2SO_4$, filtered and the filtrate was concentrated. The residue was purified by preparative TLC on silica gel (50% ethyl acetate in dichloromethane) to afford compound Int-18a. $^1$H NMR (400 MHz, $CDCl_3$) δ 10.54 (brs, 1H), 8.94 (brs, 1H), 7.62 (d, J=7.2 Hz, 2H), 7.27-7.43 (m, 4H), 6.76-6.87 (m, 2H), 5.22-5.35 (m, 2H), 4.64 (d, J=5.6 Hz, 2H), 3.60 (d, J=13.6 Hz, 1H), 3.37-3.49 (m, 1H), 3.04-3.22 (m, 5H), 2.52 (d, J=9.2 Hz, 2H), 2.33-2.45 (m, 3H), 2.23 (d, J=8.4 Hz, 2H). MS (+ESI) m/z: 523.2.

Step B—Synthesis of Compound 49

A solution of compound Int-18a (10 mg, 0.019 mmol) and LiCl (32.5 mg, 0.765 mmol) in N,N-dimethylformamide (1 mL) was stirred at 80° C. for 1.5 hours, cooled to rt and concentrated. The residue was purified by RP-HPLC to afford compound 49. $^1$H NMR (400 MHz, $CD_3OD$) δ 8.56 (s, 1H), 7.39-7.46 (m, 1H), 6.88-7.01 (m, 2H), 4.63 (s, 2H), 3.96 (d, J=13.6 Hz, 1H), 3.73-3.84 (m, 2H), 3.60 (q, J=6.8 Hz, 3H), 3.20 (s, 3H), 2.93 (s, 3H), 2.72 (s, 1H), 2.61 (s, 1H). MS (+ESI) m/z: 433.1.

Example 19

Preparation of Compound 50

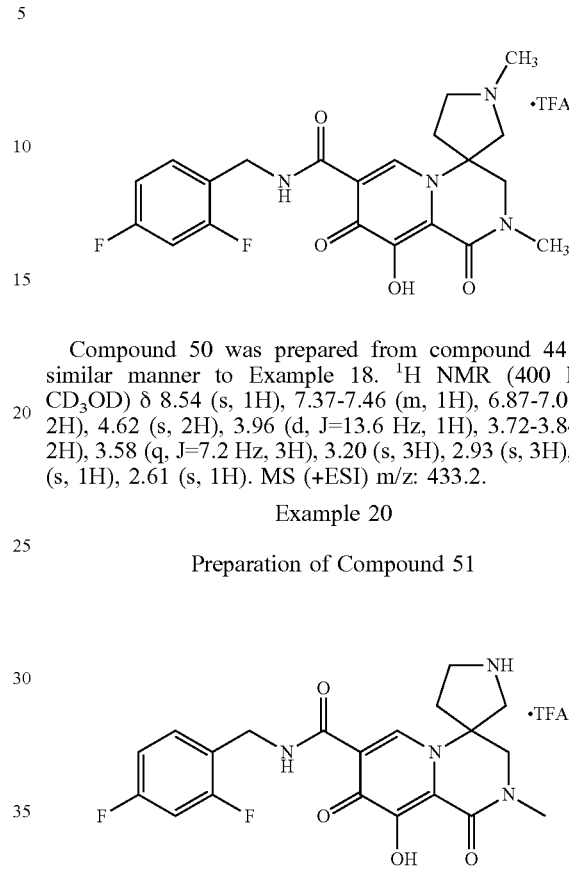

Compound 50 was prepared from compound 44 in a similar manner to Example 18. $^1$H NMR (400 MHz, $CD_3OD$) δ 8.54 (s, 1H), 7.37-7.46 (m, 1H), 6.87-7.01 (m, 2H), 4.62 (s, 2H), 3.96 (d, J=13.6 Hz, 1H), 3.72-3.84 (m, 2H), 3.58 (q, J=7.2 Hz, 3H), 3.20 (s, 3H), 2.93 (s, 3H), 2.72 (s, 1H), 2.61 (s, 1H). MS (+ESI) m/z: 433.2.

Example 20

Preparation of Compound 51

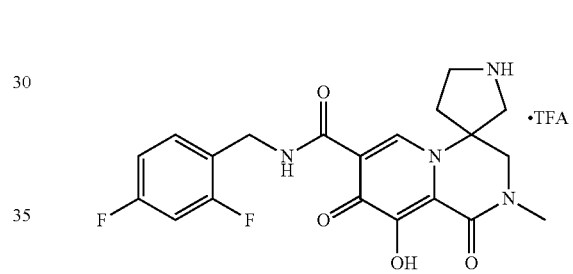

To a solution of compound 41 (25 mg, 0.041 mmol) in dichloromethane (1 mL) was added trifluoroacetic acid (0.2 mL) at 0° C. The mixture was stirred at 25° C. for 40 minutes and then concentrated. The residue was purified by RP-HPLC to afford compound 51. $^1$H NMR (400 MHz, $CD_3OD$) δ 8.41 (s, 1H), 7.37-7.47 (m, 1H), 6.87-6.99 (m, 2H), 4.55-4.67 (m, 2H), 3.67-4.02 (m, 6H), 3.19 (s, 3H), 2.77-2.86 (m, 1H), 2.51-2.61 (m, 1H). MS (+ESI) m/z: 419.1.

Example 21

Preparation of Compound 52

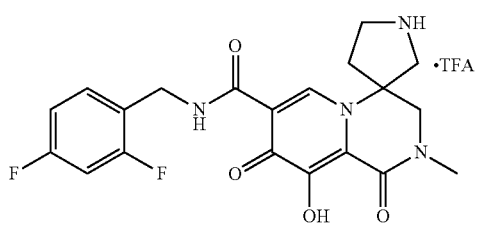 [SMILES: CN1CC2(CCNC2)n2cc(C(=O)NCc3ccc(F)cc3F)c(=O)c(O)c2C1=O]

Compound 52 was prepared from compound 42 in a similar manner to Example 20. $^1$H NMR (400 MHz, $CD_3OD$) δ 8.42 (s, 1H), 7.39-7.48 (m, 1H), 6.88-7.01 (m, 2H), 4.62 (s, 2H), 3.69-4.03 (m, 6H), 3.20 (s, 3H), 2.78-2.86 (m, 1H), 2.53-2.62 (m, 1H). MS (+ESI) m/z: 419.0.

Example 22
Preparation of Compound 53
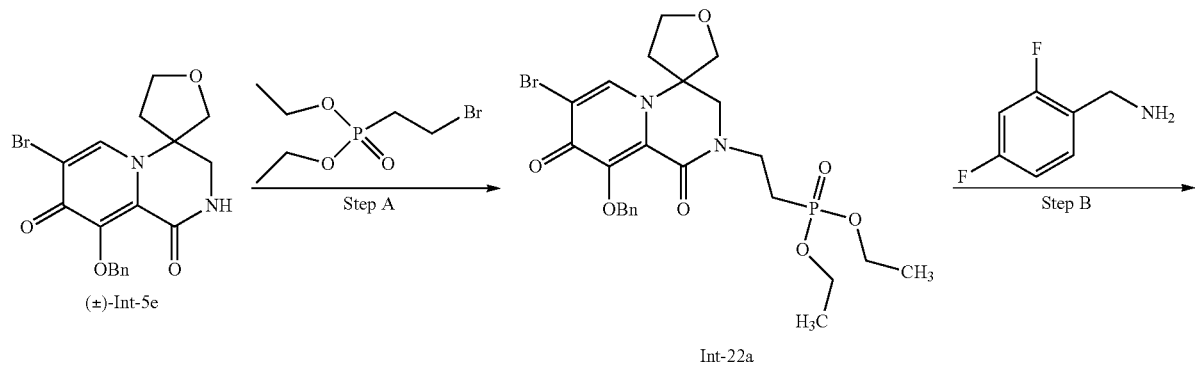
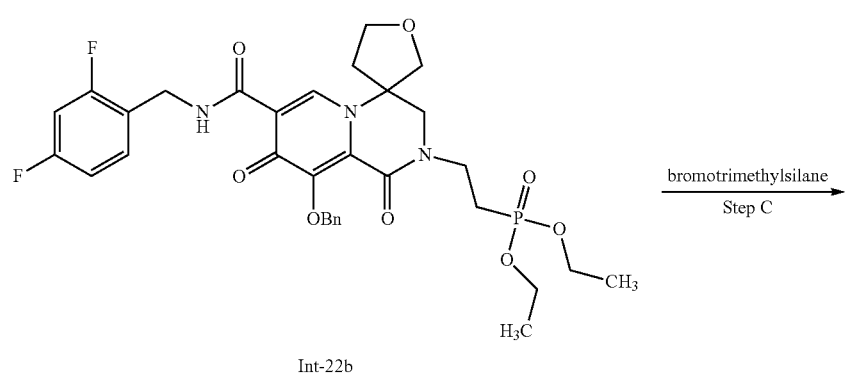
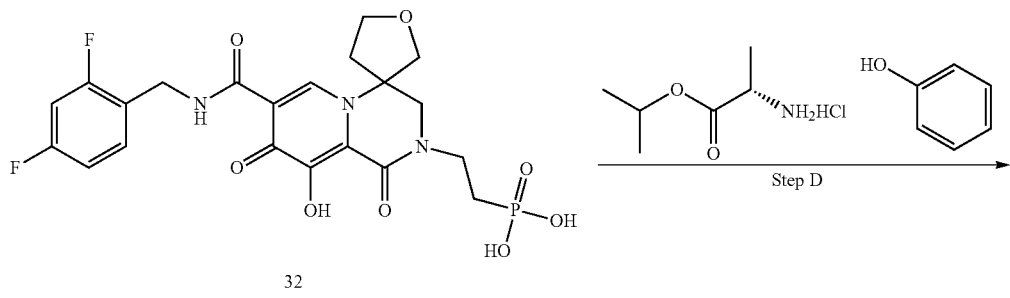
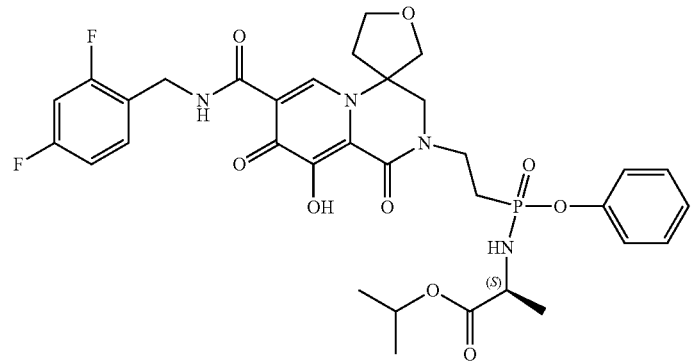

Step A—Synthesis of Intermediate Compound Int-22a

A mixture of (f)-Int-5e (210 mg, 0.518 mmol) and finely-ground potassium carbonate (286 mg, 2.073 mmol) in N,N-dimethylacetamide (10 mL) was purging with nitrogen, stirred at rt for 20 min, treated with finely-ground cesium carbonate (507 mg, 1.555 mmol) and purging with nitrogen. The mixture was stirred at rt for 20 min before diethyl 2-bromoethylphosphonate (635 mg, 2.59 mmol) was added. The mixture was then heated under microwave irradiation at 120° C. for 2 h. After cooling to rt, the solids were removed by filtration and the filtrate was concentrated. The residue was purified by column chromatography on silica gel (50 to 95% acetone in hexane) to provide compound Int-22a. MS (+ESI) m/z: 569.0, 571.0

Step B—Synthesis of Intermediate Compound Int-22b

A mixture of Int-22a (115 mg, 0.202 mmol), Pd(OAc)$_2$ (2.3 mg, 0.010 mmol), bis(2-diphenylphophinophenyl)ether (6.5 mg, 0.012 mmol) and acetonitrile (3.5 mL) in an Endeavor® reaction tube was stirred at rt for 10 min and then treated with triethylamine (0.056 mL, 0.404 mmol) and 2,4-difluorobenzylamine (0.029 mL, 0.242 mmol). The mixture was stirred at 80° C. under carbon monoxide (40 psi) for 6 hours, concentrated. The residue was purified by column chromatography on silica gel (5 to 10% methanol in dichloromethane) to provide compound Int-22b. MS (+ESI) m/z: 660.2

Step C—Synthesis of Compound 32

A solution of Int-22b (60 mg, 0.091 mmol) in dichloromethane (3 mL) was cooled to 0° C. and treated with bromotrimethylsilane (0.071 mL, 0.546 mmol). The mixture was slowly warmed to rt and stirred over 2 h, treated with additional bromotrimethylsilane (0.071 mL, 0.546 mmol), stirred at rt for 18 h and concentrated. The residue was triturated with 50% ethyl acetate in hexane (5 mL) and the solids were collected by filtration and washed with 50% ethyl acetate in hexane (2×10 mL) to provide compound 32. MS (+ESI) m/z: 514.2

Step D—Synthesis of Compound 53

A mixture of 32 (35 mg, 0.068 mmol), (S)-isopropyl 2-aminopropanoate hydrochloride (20.57 mg, 0.123 mmol) and phenol (25.7 mg, 0.273 mmol) were weighed into a flask and purged with nitrogen. Pyridine (2 mL) was added and the reaction was warmed to 60° C. with stirring. A solution of 2,2'-dipyridyl disulfide (90 mg, 0.409 mmol), triphenylphosphine (107 mg, 0.409 mmol) and triethylamine (0.114 ml, 0.818 mmol) in pyridine (4 mL) was added. The reaction was stirred at 60° C. under nitrogen for 18 h, cooled to rt, and concentrated. The residue was purified purified by column chromatography on silica gel (10 to 15% methanol in dichloromethane). Further purification by RP-HPLC (10 to 33% acetonitrile in water with 0.1% NH$_4$HCO$_3$ modifier) to provide compound 53 as a mixture of four stereoisomers. $^{31}$P NMR (500 MHz, CD$_3$CN) δ 28.02, 27.98, 27.39, 27.34. MS (+ESI) m/z: 703.2

Example 23

Preparation of Compound 54

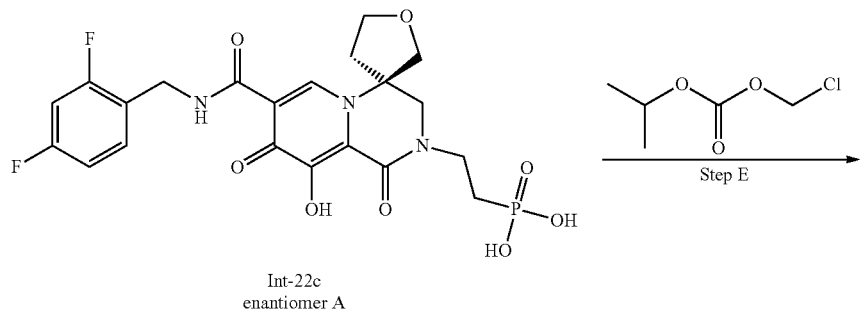

Int-22c
enantiomer A

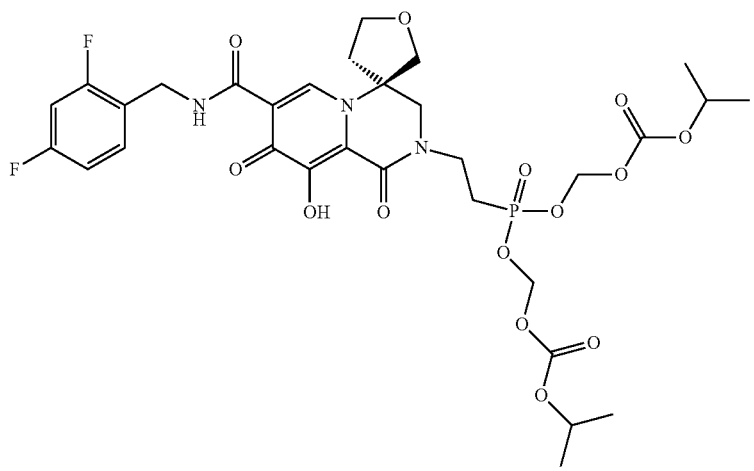

54

The single enantiomer of Int-22c (enantiomer A) was prepared from Int-5e-1 (enantiomer A) according to the procedure outlined in Example 22. To a solution of Int-22c (enantiomer A) (80 mg, 0.156 mmol) in N,N-dimethylformamide (2 mL) at rt was added triethylamine (0.174 ml, 1.247 mmol) and chloromethyl isopropyl carbonate (83 mg, 0.545 mmol). The mixture was heated at 60° C. for 18 h, cooled to rt and partitioned between dichloromethane (5 mL) and water (5 mL). The organic phase was washed with water (3×10 mL), dried with anhydrous $Na_2SO_4$ and concentrated. The residue was purified three times by column chromatography on silica gel (7% methanol in dichloromethane) to provide compound 54. $^1$H NMR (500 MHz, $CD_3CN$) δ 12.79 (s, 1H), 10.39 (t, J=5.9 Hz, 1H), 8.45 (s, 1H), 7.41 (dd, J=8.4, 15.0 Hz, 1H), 6.91-6.97 (m, 2H), 5.56-5.65 (m, 4H), 4.85-4.90 (m, 2H), 4.57 (d, J=6.0 Hz, 2H), 4.27 (d, J=11.1 Hz, 1H), 4.06 (dd, J=1.6, 3.2 Hz, 1H), 3.92-3.97 (m, 1H), 3.76-3.85 (m, 5H), 2.23-2.42 (m, 4H), 2.16 (s, 12H); $^{31}$P NMR (500 MHz, $CD_3CN$) δ 28.02. MS (+ESI) m/z: 746.2

Compounds 55 and 56 were prepared from Int-5e-1 (enantiomer A) according to the procedure outlined in Example 22.

| Compound Number | Structure | Stereochemistry | Exact Mass [M + H]$^+$ |
|---|---|---|---|
| 55 | 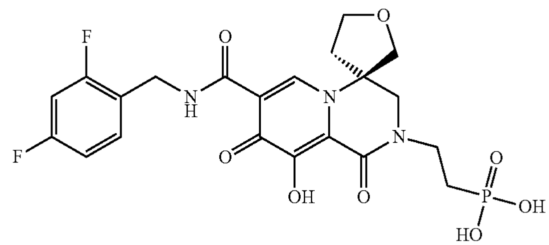 | enantiomer A | Calc'd 513.1, found 514.2 |
| 56 | 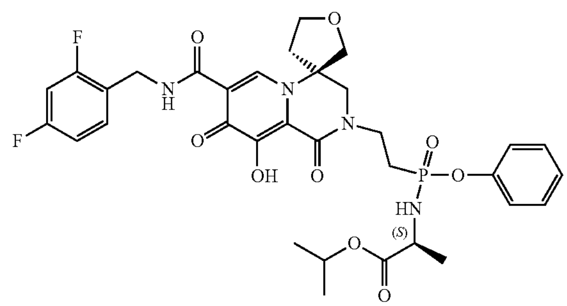 | enantiomer A epimers at P, mixture of 2 stereoisomers | Calc'd 702.2, found 703.2 |

Compounds 57 and 58 were prepared from Int-5e-2 (enantiomer B) according to the procedure outlined in Examples 22 and 23.

| Compound Number | Structure | Stereochemistry | Exact Mass [M + H]$^+$ |
|---|---|---|---|
| 57 | 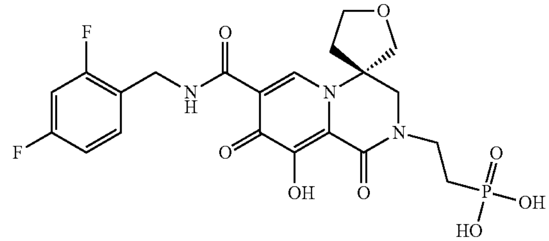 [SMILES: O=C(NCc1ccc(F)cc1F)c1cn2c(c(O)c1=O)C(=O)N(CCP(=O)(O)O)C[C@]21CCOC1] | enantiomer B | Calc'd 513.1, found 514.0 |

-continued

| Compound Number | Structure | Stereochemistry | Exact Mass [M + H]+ |
|---|---|---|---|
| 58 | 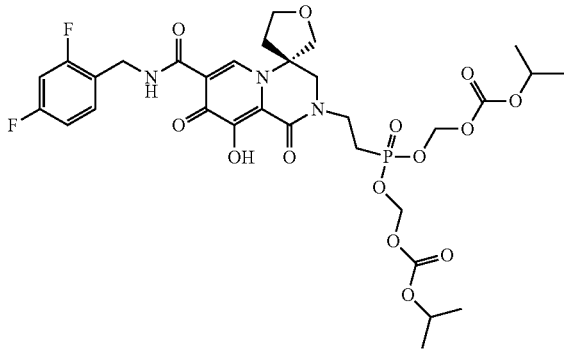 [SMILES: CC(C)OC(=O)OCOP(=O)(CCN1C[C@]2(CCOC2)n2cc(C(=O)NCc3ccc(F)cc3F)c(=O)c(O)c2C1=O)OCOC(=O)OC(C)C] | enantiomer B | Calc'd 745.2, found 746.0 |

Example 24

Assay for Inhibition of HIV Replication

MT4-GFP cells (250,000 cells/ml) were bulk-infected with HIV-1 (NL4-3 strain) at low multiplicity of infection (MOI) in RPMI+10% FBS for 24 hours. Cells were then washed once in RPMI+10% FBS and resuspended RPMI+10% or 50% normal human serum (NHS). Test compounds were serial-diluted in DMSO on ECHO. The infected MT4-GFP cells were added to a 384-well poly-D-lysine coated black plate with clear bottom in which the diluted test compounds were placed. The cells were seeded at 8,000 cells per well and the final DMSO concentration was 0.4%. The infected cells (Green GFP cells) were quantified at both 24 and 48 hours post incubation using Acumen eX3. Viral reproductive ratio ($R_0$) was determined using the number of infected cells at 48 hours divided by the number of infected cells at 24 hours. Percent viral growth inhibition was calculated by $[1-(R-R_{tripledrug})/(R_{DMSO}-R_{tripledrug})]*100$. Compound potency IP or $IC_{50}$ was determined by a 4-parameter dose response curve analysis with data for selected compounds of the present invention presented in the table below.

| Compound | VIKING $IP_{50}$ (nM) with 0% NHS | VIKING $IP_{50}$ (nM) with 100% NHS |
|---|---|---|
| 1 | 4 | 1282 |
| 2 | 19 | 1514 |
| 3 | 3 | 292 |
| 4 | 2 | 334 |
| 5 | 4 | >8400 |
| 6 | 6 | 646 |
| 7 | 6 | 113 |
| 8 | 2 | 260 |
| 9 | 2 | 814 |
| 10 | 3 | 75 |
| 11 | 3 | 442 |
| 12 | 5 | 47 |
| 13 | 2 | 36 |
| 14 | 3 | 209 |
| 15 | 4 | 108 |
| 16 | 2 | 4529 |
| 17 | 2 | >8400 |
| 18 | 3 | >8400 |
| 19 | 2 | 3422 |
| 20 | 2 | 337 |
| 21 | 3 | 129 |
| 22 | 2 | 40 |

-continued

| Compound | VIKING $IP_{50}$ (nM) with 0% NHS | VIKING $IP_{50}$ (nM) with 100% NHS |
|---|---|---|
| 23 | 1 | 27 |
| 24 | 35 | >8000 |
| 25 | 1 | 1729 |
| 26 | 1 | 1137 |
| 27 | 3 | 3661 |
| 28 | 2 | 2769 |
| 29 | 1 | 1145 |
| 30 | 1 | 417 |
| 31 | 17 | 232 |
| 32 | 293 | 873 |
| 33 | 3 | 210 |
| 34 | 5 | 4916 |
| 35 | 1 | 88 |
| 36 | 3 | 114 |
| 37 | 3 | 663 |
| 38 | 7 | 235 |
| 39 | 2 | 291 |
| 40 | 4 | 691 |
| 45 | 69 | 297 |
| 46 | 19 | 259 |
| 47 | 6 | 78 |
| 48 | 10 | 112 |
| 49 | 2 | 90 |
| 50 | 1 | 74 |
| 51 | 3 | 68 |
| 52 | 18 | 210 |
| 53 | 4 | 160 |
| 54 | 5 | 1600 |
| 58 | 7 | 530 |

What is claimed is:

1. A compound having the formula:

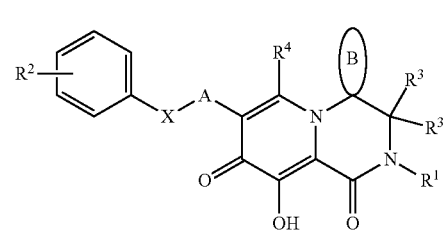

(I)

or a pharmaceutically acceptable salt thereof, wherein:
A is —NHC(O)—;
B is a 3 to 8-membered heterocycloalkyl, which can be optionally substituted with one or more groups, each independently selected from $R^5$;
X is $C_1$-$C_4$ alkylene;
$R^1$ is selected from H, $C_1$-$C_6$ alkyl, $C_3$-$C_7$ cycloalkyl, $C_1$-$C_6$ haloalkyl, $C_1$-$C_6$ hydroxyalkyl, —($C_1$-$C_4$ alkylene)-O—($C_1$-$C_6$ alkyl), —($C_1$-$C_4$ alkylene)-S—($C_1$-$C_6$ alkyl), —($C_1$-$C_4$ alkylene)-$SO_2$—($C_1$-$C_6$ alkyl), —N($C_1$-$C_6$ alkyl)$_2$, —($C_1$-$C_4$ alkylene)-N($C_1$-$C_6$ alkyl)$_2$, —($C_1$-$C_4$ alkylene)-P(O)(—O—$C_1$-$C_6$ alkyl)$_2$, —($C_1$-$C_4$ alkylene)-P(O)(OH)$_2$, phenyl, 3 to 8-membered monocyclic heterocycloalkyl and 5- or 6-membered monocyclic heteroaryl;
$R^2$ represents up to 3 optional substitutents, each independently selected from halo, $C_1$-$C_6$ alkyl, —O—($C_1$-$C_6$ alkyl) and $C_1$-$C_6$ haloalkyl;
each occurrence of $R^3$ is independently selected from H, $C_1$-$C_6$ alkyl, —OH, —O —($C_1$-$C_6$ alkyl), $C_1$-$C_6$ haloalkyl, $C_3$-$C_7$ cycloalkyl, —S—($C_1$-$C_6$ alkyl), —$NH_2$, —NH($C_1$-$C_6$ alkyl) and —N($C_1$-$C_6$ alkyl)$_2$;
$R^4$ is selected from H, $C_1$-$C_6$ alkyl, $C_3$-$C_7$ cycloalkyl, —($C_1$-$C_4$ alkylene)-O—($C_1$-$C_6$ alkyl) and $C_1$-$C_6$ haloalkyl;
each occurrence of $R^5$ is independently selected from halo, $C_1$-$C_6$ alkyl, $C_1$-$C_6$ haloalkyl, 3 to 8-membered monocyclic heterocycloalkyl, 6 to 10-membered bicyclic heterocycloalkyl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —$NH_2$, —NH($C_1$-$C_6$ alkyl), —N($C_1$-$C_6$ alkyl)$_2$, —S(O)$_2$($C_1$-$C_6$ alkyl), —NHS(O)$_2$-($C_1$-$C_6$ alkyl), —S(O)$_2$NH—($C_1$-$C_6$ alkyl), —OC(O)—($C_1$-$C_6$ haloalkyl), —($C_1$-$C_6$ alkylene)$_p$—C(O)O—($C_1$-$C_6$ alkyl), —($C_1$-$C_6$ alkylene)$_p$—C(O)—($C_1$-$C_6$ alkyl), —($C_1$-$C_6$ alkylene)$_p$—C(O)N($R^6$)$_2$, $C_1$-$C_6$ hydroxyalkyl, —P(O)(O$R^8$)$_2$, and —CN;
each occurrence of $R^6$ is independently selected from H, $C_1$-$C_6$ alkyl, $C_3$-$C_7$ cycloalkyl, $C_1$-$C_6$ haloalkyl and —($C_1$-$C_6$ alkylene)$_p$-$R^7$;
each occurrence of $R^7$ is independently selected from H, $C_1$-$C_6$ alkyl, —O—($C_1$-$C_6$ alkyl), $C_3$-$C_7$ cycloalkyl, 5- or 6-membered monocyclic heteroaryl and 3 to 8-membered monocyclic heterocycloalkyl;
each occurrence of $R^8$ is independently selected from H and $C_1$-$C_6$ alkyl; and
each occurrence of p is independently 0 or 1.

2. The compound of claim 1, wherein X is —$CH_2$—, or a pharmaceutically acceptable salt thereof.

3. The compound of claim 1, having the formula:

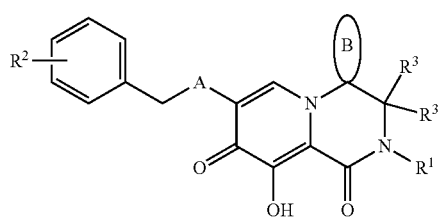

(Ia)

or a pharmaceutically acceptable salt thereof, wherein:
A is: —NHC(O)—;
B is 4 to 7-membered monocyclic heterocycloalkyl;
$R^1$ is selected from $C_1$-$C_6$ alkyl, $C_1$-$C_6$ hydroxyalkyl and —($C_1$-$C_4$ alkylene)-O—($C_1$-$C_6$ alkyl);
$R^2$ represents up to 2 optional substituents, each independently selected from halo; and
each occurrence of $R^3$ is independently H or $C_1$-$C_6$ alkoxy.

4. The compound of claim 1, wherein B is selected from:

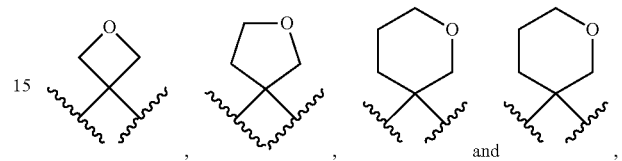

or a pharmaceutically acceptable salt thereof.

5. The compound of claim 1, wherein $R^2$ represents up to 3 substituent groups, each independently selected from F and Cl, or a pharmaceutically acceptable salt thereof.

6. The compound of claim 5, wherein $R^2$ and the phenyl group to which $R^2$ is attached is:

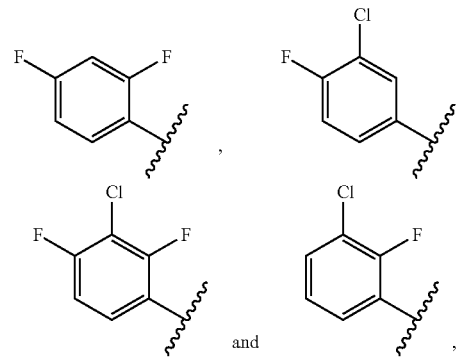

or a pharmaceutically acceptable salt thereof.

7. The compound of claim 1, wherein $^1$ is selected from methyl, ethyl, —$CH_2OCH_3$, —$CH_2CH_2OCH_3$, —$CH_2CH_2CH_2OCH_3$ and —$CH_2CH_2OCH_2CH_3$, or a pharmaceutically acceptable salt thereof.

8. The compound of claim 1, wherein one occurrence of $R^3$ is H and the other occurrence of $R^3$ is H or methoxy, or a pharmaceutically acceptable salt thereof.

9. A compound selected from

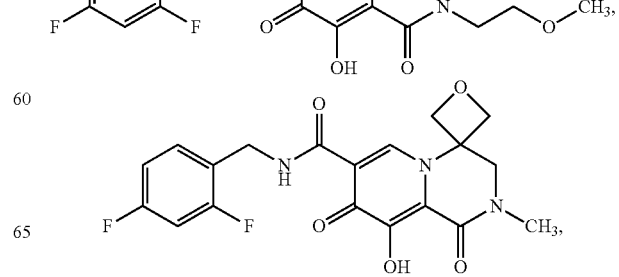

107
-continued
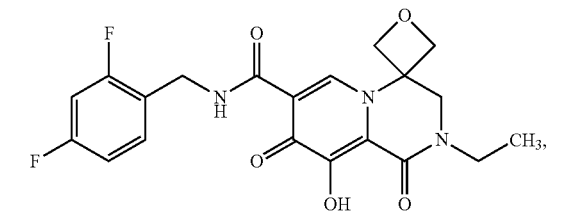
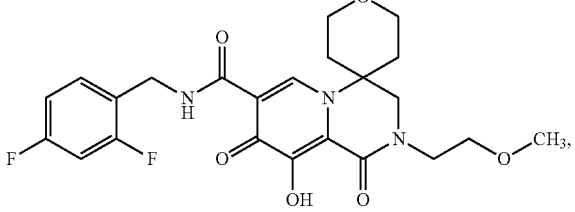
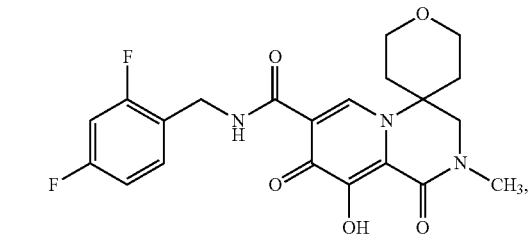
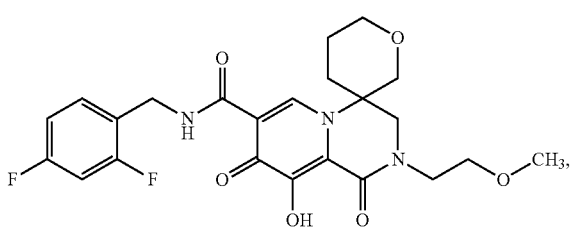
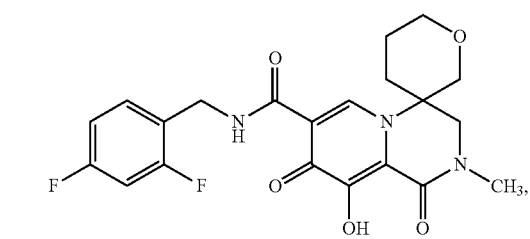
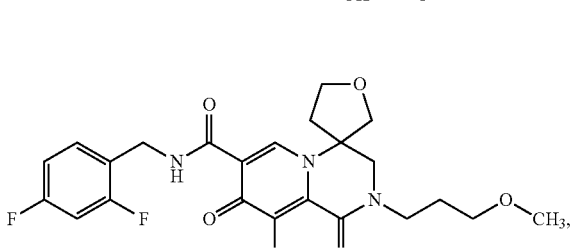
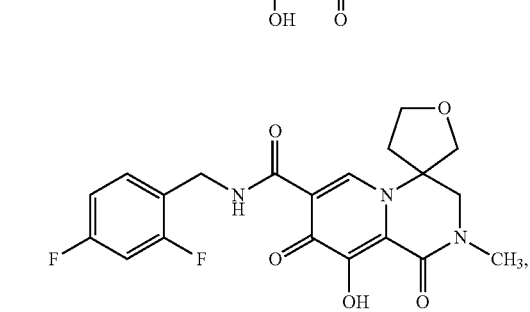
108
-continued
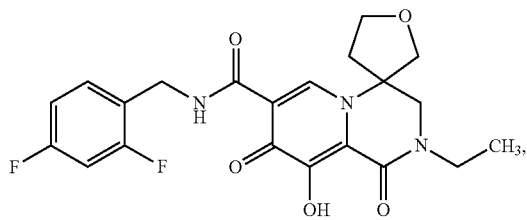
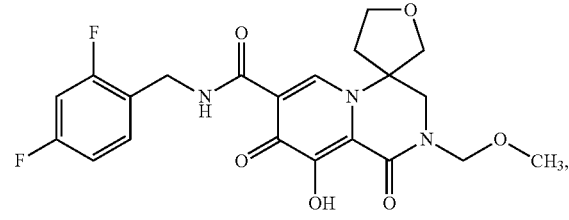
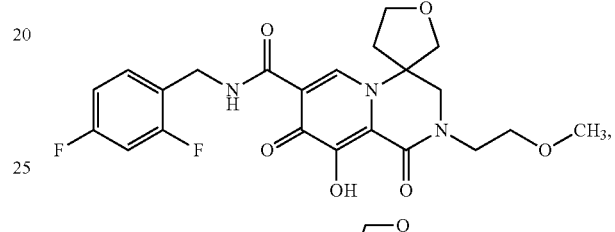
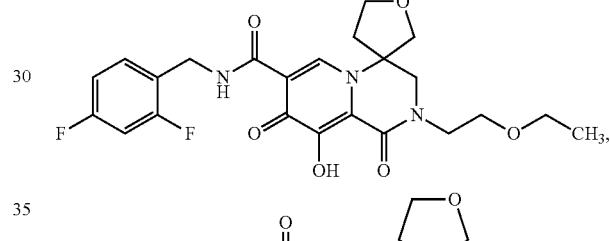
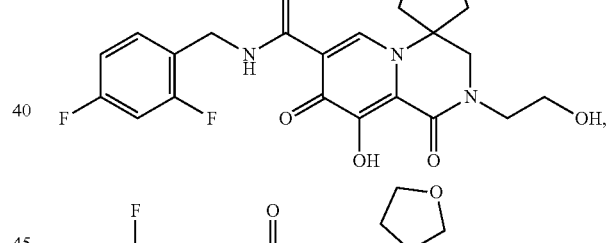
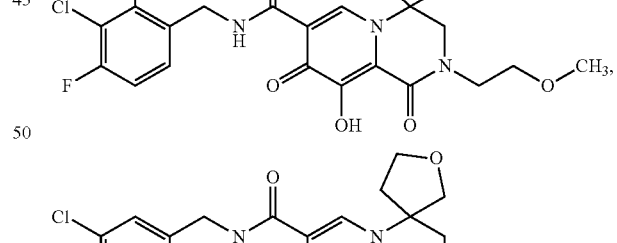
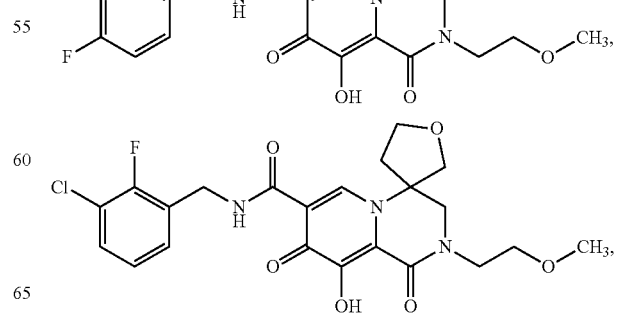

109
-continued
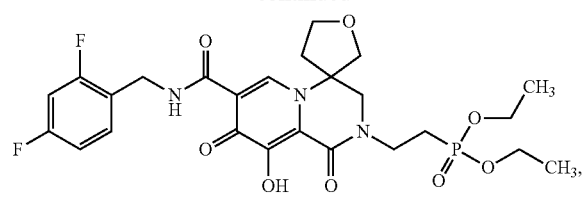
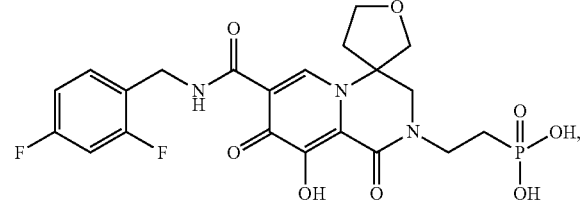
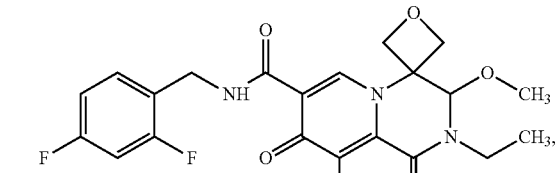
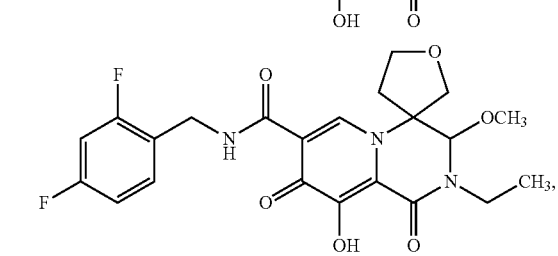
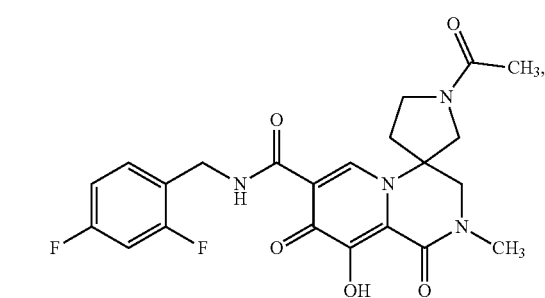
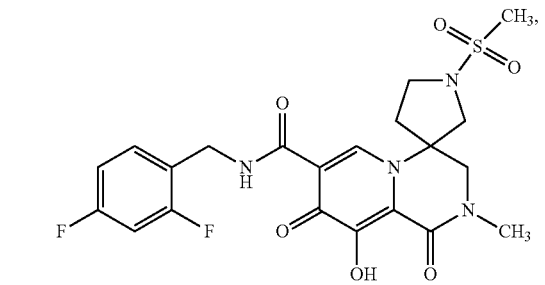
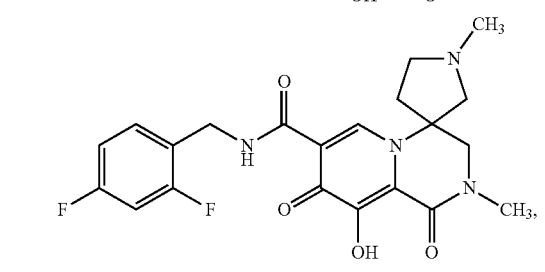
110
-continued
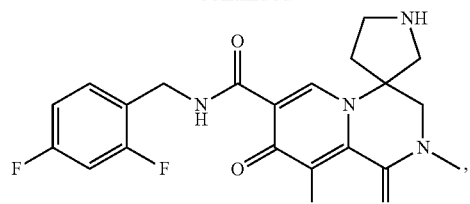
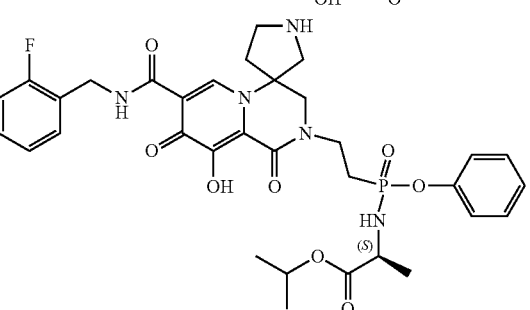
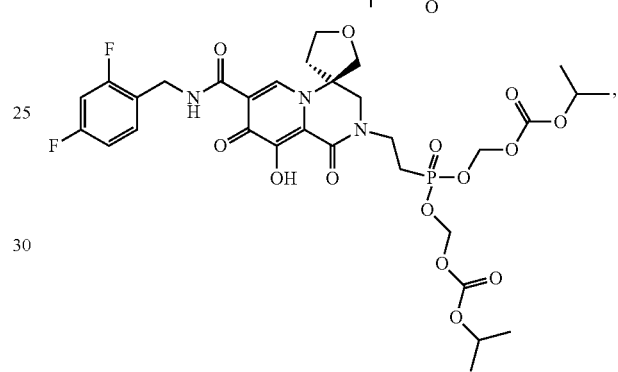
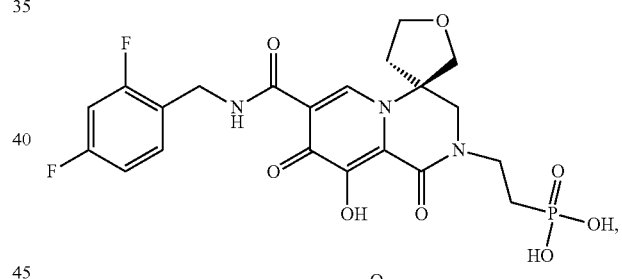
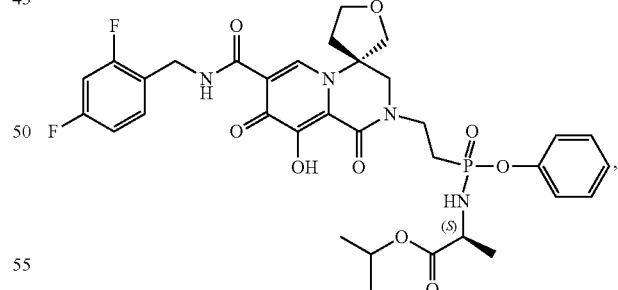
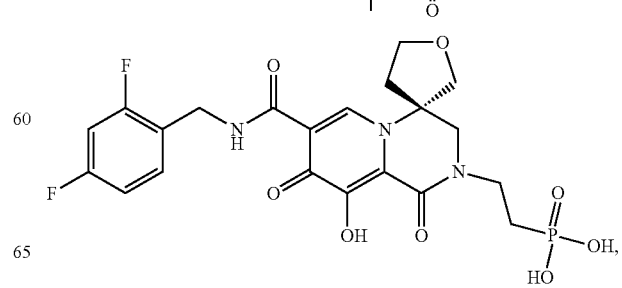

-continued

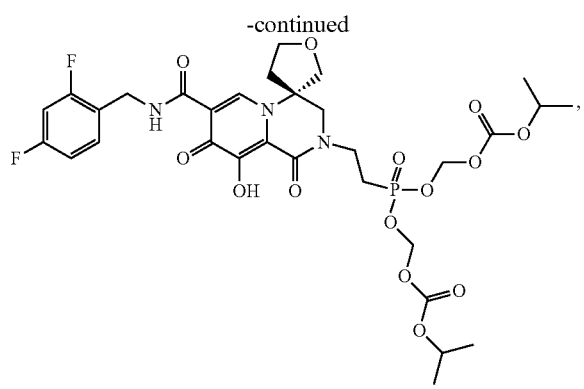

or a pharmaceutically acceptable salt thereof.

10. A pharmaceutical composition comprising an effective amount of a compound according to claim 1, or a pharmaceutically acceptable salt thereof, and a pharmaceutically acceptable carrier.

11. A method for the treatment of infection by HIV or for the treatment of AIDS in a subject in need thereof, which comprises administering to the subject an effective amount of the compound according to claim 1, or a pharmaceutically acceptable salt thereof.

12. The pharmaceutical composition of claim 10, further comprising one or more additional therapeutic agents selected from raltegravir, lamivudine, abacavir, ritonavir, dolutegravir, arunavir, atazanavir, emtricitabine, tenofovir, elvitegravir, rilpivirine and lopinavir.

13. The method of claim 11, further comprising administering to the subject one or more additional therapeutic agents selected from raltegravir, abacavir, lamivudine, ritonavir and lopinavir, wherein the amounts administered of the compound of claim 1 and the one or more additional therapeutic agents, are together effective to treat infection by HIV or to treat AIDS.

* * * * *